(12) United States Patent
Kimes et al.

(10) Patent No.: US 11,806,373 B2
(45) Date of Patent: Nov. 7, 2023

(54) THERAPEUTIC PHARMACEUTICAL COMPOSITIONS

(71) Applicant: Siolta Therapeutics, Inc., San Carlos, CA (US)

(72) Inventors: Nikole Kimes, San Francisco, CA (US); Ricardo Valladares, Brookhaven, GA (US); Neeraja Vajrala, Burlingame, CA (US)

(73) Assignee: SIOLTA THERAPEUTICS, INC., San Carlos, CA (US)

( * ) Notice: Subject to any disclaimer, the term of this patent is extended or adjusted under 35 U.S.C. 154(b) by 2 days.

(21) Appl. No.: 17/824,495

(22) Filed: May 25, 2022

(65) Prior Publication Data

US 2022/0362313 A1 Nov. 17, 2022

Related U.S. Application Data

(63) Continuation of application No. 17/475,228, filed on Sep. 14, 2021, now Pat. No. 11,406,675, which is a continuation of application No. PCT/US2020/054444, filed on Oct. 6, 2020.

(60) Provisional application No. 62/911,873, filed on Oct. 7, 2019.

(51) Int. Cl.
| | | |
|---|---|---|
| *A01N 63/00* | (2020.01) | |
| *A61K 35/747* | (2015.01) | |
| *A61K 35/741* | (2015.01) | |
| *A61K 47/02* | (2006.01) | |
| *A61K 47/10* | (2017.01) | |
| *A61K 47/20* | (2006.01) | |

(52) U.S. Cl.
CPC .......... *A61K 35/747* (2013.01); *A61K 35/741* (2013.01); *A61K 47/02* (2013.01); *A61K 47/10* (2013.01); *A61K 47/20* (2013.01)

(58) Field of Classification Search
CPC .................................................. A61K 35/747
See application file for complete search history.

(56) References Cited

U.S. PATENT DOCUMENTS

2020/0121738 A1* 4/2020 Cutcliffe .............. A61K 31/733

* cited by examiner

*Primary Examiner* — Albert M Navarro
(74) *Attorney, Agent, or Firm* — WILSON SONSINI GOODRICH & ROSATI

(57) ABSTRACT

Provided herein are pharmaceutical compositions comprising a bacterial consortium and one or more pharmaceutically acceptable excipients. Such pharmaceutical compositions can be orally administered to a subject for prevention and/or treatment of dysbiosis, dysbiosis associated conditions, inflammation, and autoimmune diseases.

20 Claims, 32 Drawing Sheets

Specification includes a Sequence Listing.

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
tatccggact cctccatctg                                              20

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tgttcgtgcg ttcttacctg                                              20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
attcctgaga aggccaggat                                              20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ctgccgacaa gcattcctat                                              20
```

```
<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
accaaggtta gccgctttt                                                   20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
cttgcccaac aaaatgacct                                                  20

<210> SEQ ID NO 7
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gtaagctctg tttcggcagc ac                                               22

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
acattgcacg ctttgccgac                                                  20

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
aattcaggtt cggctgctgt                                                  20

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 10
caggcagacg ttctgctact                                                      20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
acgcgtctct ttttgagcac                                                      20

<210> SEQ ID NO 12
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
ccaaattcaa aggacttggg ct                                                   22

<210> SEQ ID NO 13
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
cgtagtccac ttaagaaggc cg                                                   22

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
gggctttctt caaacctggc                                                      20
```

THERAPEUTIC PHARMACEUTICAL COMPOSITIONS

CROSS REFERENCE

This application is a continuation of U.S. application Ser. No. 17/475,228, filed Sep. 14, 2021, which is a continuation of International Patent Application No. PCT/US2020/054444, filed Oct. 6, 2020, which claims priority to and the benefit of U.S. Provisional Application No. 62/911,873, filed Oct. 7, 2019, the entire contents of each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Oct. 2, 2020, is named 53206-707_601_SL.txt and is 3,713 bytes in size.

BACKGROUND

Recent developments in the areas of microbiome and genome research provide evidence that the bacterial composition of the human gut fundamentally influences human health, disease onset and progression. However, much remains unknown with regards to the microbiome-host relationships, functional and metabolic changes in host due to the microbiome composition, as well as the potential development of bacterial compositions for therapeutic applications. For example, and although there is an established genetic component contributing to risk for inflammatory diseases such as allergy and asthma, environmental factors including microbial exposure and microbiome composition play key roles in the etiology of these disease. Data from clinical trials show that the gut microbiomes of infants who eventually develop allergy and asthma are distinct in bacterial species composition and immunomodulatory activity. The rising incidence of allergic diseases in general is concerning, and asthma is worrisome because it represents a rapidly growing global concern. As there is no cure for either of these allergic diseases, they represent a major public health challenge with billions of dollars spent managing their symptoms. Asthma, for example, carries a steep cost burden of over 56 billion dollars per year in the US alone, of which nearly 20 billion dollars are spent on standard of care treatments that have variable efficacy and potentially serious side effects. As a result, expansion of treatment options, such as immunomodulatory microbial compositions targeting allergic disease prevention, would address a serious unmet need, especially in disproportionately affected pediatric populations.

BRIEF SUMMARY

Provided herein are pharmaceutical compositions in solid dosage forms and comprises: a purified bacterial population comprising at least one strain of *Akkermansia* sp., *Faecalibacterium* sp., and *Lactobacillus* sp.; and a cryoprotectant. Further provided herein is a pharmaceutical composition, wherein the cryoprotectant comprises a carbohydrate and an antioxidant. Further provided herein is a pharmaceutical composition, wherein the carbohydrate comprises a saccharose, a trehalose, or a combination thereof. Further provided herein is a pharmaceutical composition, wherein the antioxidant comprises an amino acid. Further provided herein is a pharmaceutical composition, wherein the amino acid comprises a L-glutamate, a L-cysteine, or a combination thereof. Further provided herein is a pharmaceutical composition, wherein the L-cysteine is presented, by weight, in an amount from about 0.05% to about 1%. Further provided herein is a pharmaceutical composition, wherein the cryoprotectant comprises, by weight, about 60% saccharose, about 10% trehalose, about 1% L-cysteine, and about 4% L-glutamate. Further provided herein is a pharmaceutical composition, wherein the pharmaceutical composition is formulated into a suspension. Further provided herein is a pharmaceutical composition, wherein the pharmaceutical composition is formulated as an oral dosage form. Further provided herein is a pharmaceutical composition, wherein the oral dosage form is a capsule, tablet, emulsion, suspension, syrup, gel, gum, paste, herbal tea, drops, dissolving granules, powders, tablets, lyophilizate, a popsicle, or ice cream. Further provided herein is a pharmaceutical composition, wherein the bacterial population is lyophilized.

Provided herein are pharmaceutical compositions in liquid dosage forms and comprises: a purified bacterial population comprising at least one strain of *Akkermansia* sp., *Faecalibacterium* sp., and *Lactobacillus* sp.; and an antioxidant. Further provided herein is a pharmaceutical composition, further comprises a cryoprotectant. Further provided herein is a pharmaceutical composition, wherein the cryoprotectant comprises glycerol. Further provided herein is a pharmaceutical composition, wherein the glycerol is present, by volume, in an amount from about 10% to about 30%. Further provided herein is a pharmaceutical composition, wherein the antioxidant comprises an amino acid. Further provided herein is a pharmaceutical composition, wherein the amino acid comprises an L-cysteine. Further provided herein is a pharmaceutical composition, wherein the L-cysteine is present, by weight, in an amount of about 0.1%. Further provided herein is a pharmaceutical composition, further comprising a buffer. Further provided herein is a pharmaceutical composition, wherein the buffer is phosphate buffered saline (PBS) and has a pH of about 7.4. Further provided herein is a pharmaceutical composition, wherein the pharmaceutical composition has a total volume of about 1 mL. Further provided herein is a pharmaceutical composition, further comprises a container. Further provided herein is a pharmaceutical composition, wherein the container is a 2 mL polypropylene screw cap vial.

Provided herein are pharmaceutical compositions, comprising: a purified bacterial population comprising at least one strain of *Akkermansia* sp., *Lactobacillus* sp., and *Faecalibacterium* sp.; and a pharmaceutically acceptable excipient, wherein the pharmaceutical composition is encompassed in a capsule, and wherein the capsule comprises a plant-derived material. Further provided herein is a pharmaceutical composition, wherein the plant-derived material comprises a cellulose-based polymer. Further provided herein is a pharmaceutical composition, wherein the cellulose-based polymer comprises pullulan. Further provided herein is a pharmaceutical composition, wherein the capsule has an oxygen permeability less than about 0.5 $cm^3/m^2/day$, as measured by a gas composition in the capsule. Further provided herein is a pharmaceutical composition, wherein the capsule has a disintegration endpoint of about 1.6 minutes, as measured at 37° C. with de-ionized water. Further provided herein is a pharmaceutical composition, further comprises a cryoprotectant. Further provided herein is a pharmaceutical composition, wherein the cryoprotectant comprises a carbohydrate and an antioxidant. Further provided herein is a pharmaceutical composition, wherein the bacteria population is lyophilized. Further provided herein is a pharmaceutical composition, wherein the at least one strain of *Akkermansia* sp., *Faecalibacterium* sp., and *Lactobacillus* sp. is selected from the strains listed in TABLE 1. Further provided herein is a pharmaceutical composition, wherein the bacterial population comprises *A. muciniphila* (DSM 33213), *F. prausnitzii* (DSM 33185), or *L. crispatus* (DSM 33187). Further provided herein is a pharmaceutical composition, wherein the bacterial population comprises at least two of the bacterial strains *A. muciniphila* (DSM 33213), *F. prausnitzii* (DSM 33185), and *L. crispatus* (DSM 33187). Further provided herein is a pharmaceutical composition, wherein the bacterial population comprises the bacterial strains *A. muciniphila* (DSM 33213), *F. prausnitzii* (DSM 33185), and *L. crispatus* (DSM 33187). Further provided herein is a pharmaceutical composition, wherein each bacterial strain is present in an amount from about $10^3$ CFU to about $10^{12}$ CFU. Further provided herein is a pharmaceutical composition, wherein each bacterial strain is present in an amount from about $10^7$ CFU to about $10^{10}$ CFU. Further provided herein is a pharmaceutical composition, wherein each bacterial strain is present in an amount of about $5\times10^8$ CFU. Further provided herein is a pharmaceutical composition, wherein the bacterial population is present in a total amount of about $10^3$ CFU to about $10^{12}$ CFU. Further provided herein is a pharmaceutical composition, wherein the bacterial population is present in a total amount of about $10^7$ CFU to about $10^{10}$ CFU. Further provided herein is a pharmaceutical composition, wherein the bacterial population is present in a total amount of about $1.5\times10^9$ CFU.

Provided herein are method of treating a disease in a subject, the method comprising administering to the subject any pharmaceutical composition previously described. Further provided herein is a method for treating a disease in a subject, wherein the disease is an inflammatory disease. Further provided herein is a method for treating a disease in a subject, wherein the inflammatory disease is an allergy or dermatitis. Further provided herein is a method for treating a disease in a subject, wherein the allergy is allergic asthma, allergic pediatric asthma or food allergy. Further provided herein is a method for treating a disease in a subject, wherein the disease is a metabolic disease. Further provided herein is a method for treating a disease in a subject, wherein the metabolic disease is obesity, diabetes, or a metabolic syndrome.

Provided herein is methods of reducing the incidence of an allergic condition in a subject, the method comprising orally administering to the subject a pharmaceutical composition comprising a purified bacterial population comprising a strain of *Akkermansia* sp., *Faecalibacterium* sp., and *Lactobacillus* sp., wherein the pharmaceutical composition is administered to the subject at least once daily for at least 7 days. Further provided herein is a method of reducing the incidence of an allergic condition in a subject, wherein the subject is a neonate of equal to or less than about 7 days of age. Further provided herein is a method of reducing the incidence of an allergic condition in a subject, wherein the subject is an infant of from about 28 days to about 12 months of age. Further provided herein is a method of reducing the incidence of an allergic condition in a subject, wherein the pharmaceutical composition is administered to the subject for at least 28 days. Further provided herein is a method of reducing the incidence of an allergic condition in a subject, wherein the pharmaceutical composition is administered to the subject for at least 336 days. Further provided herein is a method of reducing the incidence of an allergic condition in a subject, wherein the pharmaceutical composition is administered to the subject once, two, three, four, five, or six times daily. Further provided herein is a method of reducing the incidence of an allergic condition in a subject, wherein the pharmaceutical administered to the subject once, two, three, four, five, six, seven, eight, nine, ten, eleven, or twelve times daily. Further provided herein is a method of reducing the incidence of an allergic condition in a subject, wherein the allergic condition is atopic dermatitis, food allergy, allergic rhinitis, or allergic asthma. Further provided herein is a method of reducing the incidence of an allergic condition in a subject, wherein the subject has a biological mother, father, or sibling with a history of an allergic condition is atopic dermatitis, food allergy, allergic rhinitis, or allergic asthma. Further provided herein is a method of reducing the incidence of an allergic condition in a subject, wherein the subject has a birthweight from about 2.5 kg to 4.5 kg. Further provided herein is a method of reducing the incidence of an allergic condition in a subject, wherein each bacterial strain is present in an amount from about $10^3$ CFU to about $10^{12}$ CFU. Further provided herein is a method of reducing the incidence of an allergic condition in a subject, wherein each bacterial strain is present in an amount from about $10^7$ CFU to about $10^{10}$ CFU. Further provided herein is a method of reducing the incidence of an allergic condition in a subject, wherein each bacterial strain is present in an amount of about $5\times10^8$ CFU. Further provided herein is a method of reducing the incidence of an allergic condition in a subject, wherein the bacterial population is present in a total amount of about $10^3$ CFU to about $10^{12}$ CFU. Further provided herein is a method of reducing the incidence of an allergic condition in a subject, wherein the bacterial population is present in a total amount of about $10^7$ CFU to about $10^{10}$ CFU. Further provided herein is a method of reducing the incidence of an allergic condition in a subject, wherein the bacterial population is present in a total amount of about $1.5\times10^9$ CFU. Further provided herein is a method of reducing the incidence of an allergic condition in a subject, wherein the *Akkermansia* sp., *Faecalibacterium* sp., and *Lactobacillus* sp. are administered at an equal amount. Further provided herein is a method of reducing the incidence of an allergic condition in a subject, wherein the *Akkermansia* sp., *Faecalibacterium* sp., and *Lactobacillus* sp. are administered at $5\times10^8$ CFU each. Further provided herein is a method of reducing the incidence of an allergic condition in a subject, further comprising a carbohydrate-based excipient. Further provided herein is a method of reducing the incidence of an allergic condition in a subject, wherein the pharmaceutical composition is mixed into breast milk, formula, or food. Further provided herein is a method of reducing the incidence of an allergic condition in a subject, wherein the suspension comprises a cryoprotectant. Further provided herein is a method of reducing the incidence of an allergic condition in a subject, wherein the cryoprotectant comprises glycerol. Further provided herein is a method of reducing the incidence of an allergic condition in a subject, wherein the glycerol is present, by volume, in an amount from about 10% to about 30%. Further provided herein is a method of reducing the incidence of an allergic condition in a subject, further comprises an antioxidant. Further provided herein is a method of reducing the incidence of an allergic condition in a subject, wherein the antioxidant comprises an amino acid. Further provided herein is a method of reducing the incidence of an allergic condition in a subject, wherein the amino acid comprises an L-cysteine. Further provided herein is a method of reducing the incidence of an allergic condition in a subject, wherein the L-cysteine is present, by weight, in an amount of about 0.1%. Further provided herein is a method of reducing the incidence of an allergic condition in a subject, further comprising a buffer. Further provided herein is a method of reducing the incidence of an allergic condition in a subject, wherein the buffer is phosphate buffered saline (PBS) and has a pH of about 7.4. Further provided herein is a method of reducing the incidence of an allergic condition in a subject, wherein the pharmaceutical composition has a total volume of about 1 mL. Further provided herein is a method of reducing the incidence of an allergic condition in a subject, wherein the composition is encompassed in a capsule. Further provided herein is a method of reducing the incidence of an allergic condition in a subject, wherein the capsule comprises plant-based material. Further provided herein is a method of reducing the incidence of an allergic condition in a subject, wherein the capsule comprises cryoprotectant. Further provided herein is a method of reducing the incidence of an allergic condition in a subject, wherein the cryoprotectant comprises a carbohydrate and an antioxidant. Further provided herein is a method of reducing the incidence of an allergic condition in a subject, wherein the carbohydrate comprises a saccharose, a trehalose, or a combination thereof. Further provided herein is a method of reducing the incidence of an allergic condition in a subject, wherein the antioxidant comprises an amino acid. Further provided herein is a method of reducing the incidence of an allergic condition in a subject, wherein the amino acid comprises a L-glutamate, a L-cysteine, or a combination thereof. Further provided herein is a method of reducing the incidence of an allergic condition in a subject, wherein the L-cysteine is presented, by weight, in an amount from about 0.05% to about 1%. Further provided herein is a method of reducing the incidence of an allergic condition in a subject, wherein the cryoprotectant comprises, by weight, about 60% saccharose, about 10% trehalose, about 1% L-cysteine, and about 4% L-glutamate. Further provided herein is a method of reducing the incidence of an allergic condition in a subject, wherein the bacterial population is lyophilized.

Provided herein are methods for a large-scale growth of *Akkermansia* sp. comprising performing a plurality of inoculation rounds with an increasing amount of growth media, wherein each inoculation round comprises at least about 5% of a total batch material of a preceding inoculation round. Further provided herein is a method for a large-scale growth of *Akkermansia* sp., wherein the *Akkermansia* sp. comprises *Akkermansia muciniphila* or *Akkermansia glycaniphila*. Further provided herein is a method for a large-scale growth of *Akkermansia* sp., wherein the *Akkermansia muciniphila* comprises *Akkermansia muciniphila* (DSM 33213). Further provided herein is a method for a large-scale growth of *Akkermansia* sp., wherein the growth media is from about 1 L to about 4,000 L. Further provided herein is a method for a large-scale growth of *Akkermansia* sp., further comprising an initial inoculation round of about 1 L growth media. Further provided herein is a method for a large-scale growth of *Akkermansia* sp., wherein at least one of the inoculation rounds is in a volume of at least about 3000 L growth media. Further provided herein is a method for a large-scale growth of *Akkermansia* sp., wherein the initial inoculation round comprises a frozen stock of *Akkermansia muciniphila* of about 2% of an initial inoculation round growth media. Further provided herein is a method for a large-scale growth of *Akkermansia* sp., wherein the initial inoculation round comprises growing *Akkermansia muciniphila* in anaerobic condition. Further provided herein is a method for a large-scale growth of *Akkermansia* sp., further comprising a final inoculation round, wherein the final inoculation round comprises *Akkermansia* sp. present in an amount of OD600 of at least 2.5. Further provided herein is a method for a large-scale growth of *Akkermansia* sp., further comprising a final inoculation round of, by volume, about 10% of the total batch material of the preceding inoculation round. Further provided herein is a method for a large-scale growth of *Akkermansia* sp., further comprising performing a plurality of sterilization rounds for the growth media, wherein each sterilization round comprises degassing the growth media with $N_2H_2CO_2$ (90:5:5). Further provided herein is a method for a large-scale growth of *Akkermansia* sp., further comprising lyophilizing the batch. Further provided herein is a method for a large-scale growth of *Akkermansia* sp., further comprising centrifuging the batch before the lyophilizing. Further provided herein is a method for a large-scale growth of *Akkermansia* sp., further comprising grinding the batch after the lyophilizing. Further provided herein is a method for a large-scale growth of *Akkermansia* sp., wherein during the period of growth of each inoculation round, the growth media has a pH value of less than about 7. Further provided herein is a method for a large-scale growth of *Akkermansia* sp., wherein during the period of growth of each inoculation round, the growth media has a pH value of less than about 6.5.

Provided herein are methods for a large-scale growth of *Faecalibacterium* sp. comprising performing a plurality of inoculation rounds with an increasing amount of growth media, wherein during the period of growth of each inoculation round, the growth media has a pH value of less than about 6.5. Further provided herein is a method for a large-scale growth of *Faecalibacterium* sp., wherein the *Faecalibacterium* sp. comprises *Faecalibacterium prausnitzii*. Further provided herein is a method for a large-scale growth of *Faecalibacterium* sp., wherein the *Faecalibacterium* sp. comprises *Faecalibacterium prausnitzii*. Further provided herein is a method for a large-scale growth of *Faecalibacterium* sp., wherein *Faecalibacterium prausnitzii* comprises *Faecalibacterium prausnitzii* (DSM 33185). Further provided herein is a method for a large-scale growth of *Faecalibacterium* sp., wherein the growth media is from about 1 L to about 4,000 L. Further provided herein is a method for a large-scale growth of *Faecalibacterium* sp., further comprising an initial inoculation round of about 1 L growth media. Further provided herein is a method for a large-scale growth of *Faecalibacterium* sp., wherein at least one of the inoculation rounds is at least about 3000 L growth media. Further provided herein is a method for a large-scale growth of *Faecalibacterium* sp., wherein the initial inoculation round comprises a frozen stock of *Faecalibacterium prausnitzii* of about 0.4% of an initial inoculation round growth media. Further provided herein is a method for a large-scale growth of *Faecalibacterium* sp., wherein the initial inoculation round comprises growing *Faecalibacterium prausnitzii* in anaerobic condition. Further provided herein is a method for a large-scale growth of *Faecalibacterium* sp., further comprising a final inoculation round, wherein the final inoculation round comprises *Faecalibacterium* sp present in an amount of $OD_{600}$ of at least 5. Further provided herein is a method for a large-scale growth of *Faecalibacterium* sp., further comprises performing a plurality of sterilization and degassing rounds for the growth media, wherein each sterilization round comprises autoclaving the growth media at 121° C. for 20 minutes, and wherein each degassing round comprises degassing the growth media with $N_2H_2CO_2$ (90:5:5). Further provided herein is a method for a large-scale growth of *Faecalibacterium* sp., further comprising lyophilizing the batch. Further provided herein is a method for a large-scale growth of *Faecalibacterium* sp., further comprising centrifuging the batch before the lyophilizing. Further provided herein is a method for a large-scale growth of *Faecalibacterium* sp., further comprising grinding the batch after the lyophilizing. Further provided herein is a method for a large-scale growth of *Faecalibacterium* sp., wherein during the period of growth of each inoculation round, the growth media has a pH value of less than about 6. Further provided herein is a method for a large-scale growth of *Faecalibacterium* sp., wherein during the period of growth of each inoculation round, the growth media has a pH value of less than about 5.5. Further provided herein is a method for a large-scale growth of *Faecalibacterium* sp., wherein during the period of growth of each inoculation round, the growth media has a pH value of less than about 5. Further provided herein is a method for a large-scale growth of *Faecalibacterium* sp., wherein each inoculation round comprises at least about 1% of a total batch material of a preceding inoculation round.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings ("FIGURE." or "FIGURES." herein), of which:

FIG. 17A shows flow cytometry results obtained when a gate was applied to all cells counted by Forward Scatter Area (FSC-A) and Side Scatter Area (SSC-A) to select for cell size and granularity, respectively.

FIG. 17B shows flow cytometry results obtained when cells were gated on linearity based on Forward Scatter Height (FSC-H) and Forward Scatter-Area (FSC-A) to identify single cells.

FIG. 17C shows flow cytometry results obtained when single cells were used to set gates for dead cells (PIhighSYTO9 low) as well as live cells (PI-SYTO9 high), which gave the percentages of live and dead cells in 50 µL of cell suspension.

DETAILED DESCRIPTION

Figure 1:
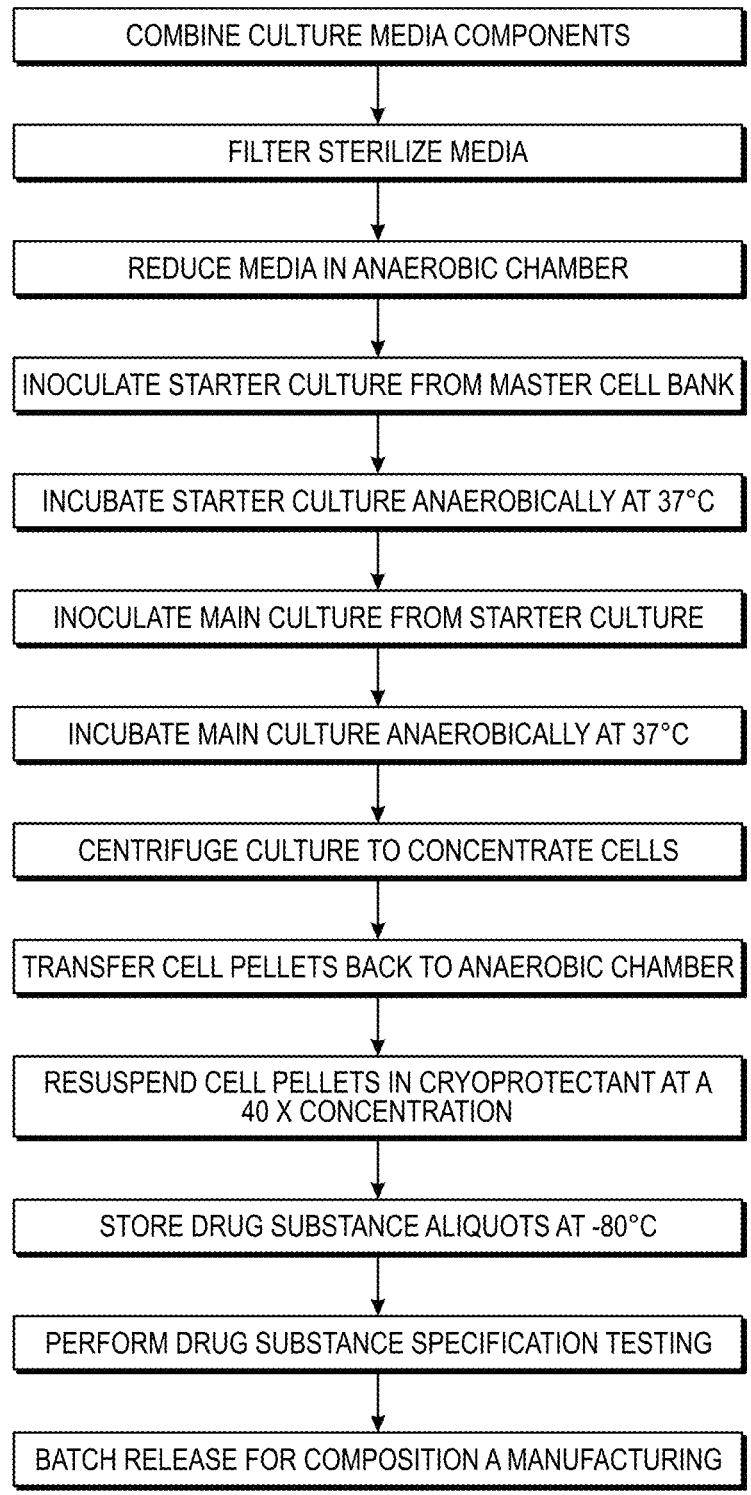
FIG. 1 shows a schematic flow chart summarizing the manufacturing steps of compositions as described herein.

Provided herein are pharmaceutical compositions comprising bacteria for treatment of an inflammatory or metabolic disease. In some instances, the pharmaceutical compositions further comprise one or more pharmaceutically acceptable excipients. Pharmaceutical compositions described may comprise one or more bacterial species, including one or more bacteria strains. In some instances, pharmaceutical compositions can comprise, consist essentially of, or consist of any one or more of *Lactobacillus* species (sp.), *Akkermansia* sp., and/or *Faecalibacterium* sp. In further instances, pharmaceutical compositions described herein comprise, consist essentially of, or consist of any one or more particular strains of the following species referenced herein: *Lactobacillus* sp., *Akkermansia* sp., and/or *Faecalibacterium* sp. For example, in some instances, pharmaceutical compositions described herein comprise, consist essentially of, or consists of the bacterial strains *Lactobacillus crispatus*(DSM 33187) (also referred to herein as "*L. crispatus* (DSM 33187)"), *Akkermansia muciniphila* with deposit ID number DSM 33213 (also referred to herein as "*A. muciniphila* (DSM 33213)"), and *Faecalibacterium prausnitzii* (DSM 33185) (also referred to herein as "*F. prausnitzii* (DSM 33185)"). In some cases, pharmaceutical compositions can comprise Composition A, as defined in Example 2.

Provided herein are pharmaceutical composition, formulations of such compositions, methods of manufacturing such compositions, administering routes for such pharmaceutical compositions, as well as indications that may be prevented and/or treated using such pharmaceutical compositions.

The present disclosure also provides methods of formulating a pharmaceutical composition described herein, as well as methods for administering such pharmaceutical compositions to a subject having or suspected of having a disease or condition. Such methods can comprise formulating a pharmaceutical composition herein that can comprise or consist of one or more bacterial species and/or strains into an oral dosage form. Such oral formulation can comprise or consist of one or more bacterial species and/or strains, a buffered glycerol solution, e.g., one that can be composed of standard phosphate buffered saline containing 137 mM NaCl, 2.7 mM KCl, 10 mM $Na_2HPO_4$, and 1.8 mM $KH_2PO_4$, 20% v/v glycerol, and an antioxidant such as 0.1% w/w L-cysteine.

Further provided herein are methods of manufacturing that allow for production of batches of bacterial strain described herein. Such methods can provide one or more advantages compared to conventional methods of manufacturing. Such advantages can include any one or more of (i) increased total yields, (ii) increased growth rates, and/or (iii) higher numbers of viable bacterial cells per number of total cells. In some instances, such methods can include use of non-animal derived media components. Such non-animal media can include vegetal media. Such vegetal media can comprise various components such as vegetal peptone, vegetal extracts, yeast extract, and other non-animal components. In some instances, such non-animal media can include N-acetyl glucosamine-threonine (NAGT) media and Boullion MRS vegetal media, Yeast fatty acid Phytone (YFAP) media, as well as modified versions thereof. Such modified media can have one or more media components removed, added, and/or substituted by other components. In other instances, the amount of a media component is increased or decreased compared to an unmodified media. In an example, a modified NAGT media may not comprise any one or more of magnesium, calcium, or glucose.

Such oral formulations of the present disclosure can be used in a method of preventing and/or treating a disease or condition in a subject, the method comprising administering the oral formulation to a subject (e.g., a human) having or suspected of having the disease or condition. Such disease or condition can be an inflammatory disease (e.g., an allergy or asthma) or an autoimmune disease.

Definitions

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The term "about," as used herein in the context of a numerical value or range, generally refers to ±10%, 9%, 8%, 7%, 6%, 5%, 4%, 3%, 2%, or 1% of the numerical value or range recited or claimed, unless otherwise specified.

Pharmaceutical Compositions

The present disclosure provides pharmaceutical compositions that can comprise, consist essentially of, or consist of a bacterial consortium and one or more pharmaceutical excipients. Such pharmaceutical excipients can include a cryoprotectant, an antioxidant, and an aqueous buffer solution.

Provided herein are pharmaceutical composition that can comprise a bacterial consortium. Such bacterial consortium can comprise one or more different bacterial species and/or strains. Such bacterial species and/or strains can belong to one or more different bacterial phyla. Such bacterial phyla can include Verrucomicrobia, Firmicutes, Proteobacteria, Actinobacteria, and/or Bacteroidetes, or a combination thereof.

In some instances, a bacterial consortium described herein can comprise one or more *Lactobacillus* sp. The one or more *Lactobacillus* sp. can include *Lactobacillus johnsonii*, *Lactobacillus rhamnosus*, *Lactobacillus zeae*, *Lactobacillus acidipiscis*, *Lactobacillus acidophilus*, *Lactobacillus agilis*, *Lactobacillus aviarius*, *Lactobacillus brevis*, *Lactobacillus coleohominis*, *Lactobacillus crispatus*, *Lactobacillus crustorum*, *Lactobacillus curvatus*, *Lactobacillus diolivorans*, *Lactobacillus farraginis*, *Lactobacillus fermentum*, *Lactobacillus fuchuensis*, *Lactobacillus harbinensis*, *Lactobacillus helveticus*, *Lactobacillus hilgardii*, *Lactobacillus intestinalis*, *Lactobacillus jensenii*, *Lactobacillus kefiranofaciens*, *Lactobacillus kefiri*, *Lactobacillus lindneri*, *Lactobacillus mali*, *Lactobacillus manihotivorans*, *Lactobacillus mucosae*, *Lactobacillus oeni*, *Lactobacillus oligofermentans*, *Lactobacillus panis*, *Lactobacillus pantheris*, *Lactobacillus parabrevis*, *Lactobacillus paracollinoides*, *Lactobacillus parakefiri*, *Lactobacillus paraplantarum*, *Lactobacillus pentosus*, *Lactobacillus pontis*, *Lactobacillus reuteri*, *Lactobacillus rossiae*, *Lactobacillus salivarius*, *Lactobacillus siliginis*, *Lactobacillus sucicola*, *Lactobacillus vaccinostercus*, *Lactobacillus vaginalis*, *Lactobacillus vini*, *Lactococcus garvieae*, or *Lactococcus lactis*, or a combination thereof. In some embodiments, the *Lactobacillus* sp. is *Lactobacillus johnsonii* or *Lactobacillus crispatus*. In such instances, a bacterial consortium herein can comprise one or more *Lactobacillus johnsonii* or *Lactobacillus crispatus* strains. Such one or more *Lactobacillus crispatus* strain(s) can include *Lactobacillus crispatus*(DSM 33187) (i.e., *L. crispatus* (DSM 33187)). In various instances, a bacterial consortium herein comprises *Lactobacillus crispatus*(DSM 33187).

In some instances, a bacterial consortium herein can comprise one or more *Akkermansia* sp. Such one or more *Akkermansia* sp. can include *Akkermansia muciniphila*, *Akkermansia glycaniphila*, or a combination thereof. In some instances, the one or more *Akkermansia* sp. is *Akkermansia muciniphila*. In such instances, a bacterial consortium herein can comprise one or more *Akkermansia muciniphila* strains. Such one or more *Akkermansia muciniphila* strains can include *Akkermansia muciniphila* (DSM 33213). In various instances, a bacterial consortium herein comprises *Akkermansia muciniphila* (DSM 33213).

In some instances, a bacterial consortium herein can comprise one or more *Faecalibacterium* sp. The one or more *Faecalibacterium* sp. can include *Faecalibacterium prausnitzii*. In such instances, a bacterial consortium herein can comprise one or more *Faecalibacterium prausnitzii* strains. Such one or more *Faecalibacterium prausnitzii* strains can include *Faecalibacterium prausnitzii* (DSM 33185), *Faecalibacterium prausnitzii* (DSM 33191), *Faecalibacterium prausnitzii* (DSM 33186), or *Faecalibacterium prausnitzii* (DSM 33190), or a combination thereof. In various instances, a bacterial consortium herein comprises *Faecalibacterium prausnitzii* (DSM 33185).

Further provided herein are bacterial consortia that can comprise one or more strains of any one or more of *Bacteroides* sp., *Blautia* sp., *Bifidobacterium* sp., *Coprococcus* sp., or *Dorea* sp. In such instances, a bacterial consortium herein can comprise any one or more of *Bacteroides faecis* (DSM 33177), *Bacteroides thetaiotaomicron* (DSM 33178), *Blautia producta* (DSM 33180), *Bifidobacterium longum* (DSM 33179), *Coprococcus comes* (DSM 33176), or *Dorea longicatena* (DSM 33188). Exemplary strains for inclusion in a bacterial consortium described herein are listed in TABLE 1.

TABLE 1

Exemplary Bacterial Strains.

| Bacterial Strain | Deposit ID # | Bacterial Strain | Deposit ID # |
| --- | --- | --- | --- |
| A. muciniphila | DSM 33213 | F. prausnitzii | DSM 33191 |
| B. longum | DSM 33179 | F. prausnitzii | DSM 33186 |
| B. producta | DSM 33180 | F. prausnitzi | DSM 33190 |
| B. thetaiotaomicron | DSM 33178 | L. crispatus | DSM 33187 |
| C. comes | DSM 33176 | B. faecis | DSM 33177 |
| F. prausnitzii | DSM 33185 | Dorea lonpicatena | DSM 33188 |

Provided herein are bacterial consortia that can comprise, consist essentially of, or consist of 20, 19, 18, 17, 16, 15, 14, 13, 12, 11, 10, 9, 8, 7, 6, 5, 4, 3, 2 or 1 bacterial species and/or strain(s). In some instances, such bacterial consortia can comprise at least one bacterial strain selected from TABLE 1. In some embodiments, a bacterial consortium can consist of up to 3 different bacterial strains. In some embodiments, a bacterial consortium described herein comprises at least one, at least two, or all three bacterial strains listed in TABLE 2. In some instances, a bacterial consortium comprises or consists of the bacterial strains *L. crispatus* (DSM 33187), *A. muciniphila* (DSM 33213), and *F. prausnitzii* (DSM 33185).

TABLE 2

A Subset of Bacterial Strains.

| Bacterial strain | Deposit ID # |
| --- | --- |
| *Lactobacillus crispatus* | DSM 33187 |
| *Akkermansia muciniphila* | DSM 33213 |
| *Faecalibacterium prausnitzii* | DSM 33185 |

The present disclosure provides bacterial consortia that can comprise a varying number of colony-forming units (CFU) of each of the bacterial species and/or strain it contains. In some instance, such bacterial consortium can comprise from about $10^3$ CFU to about $10^{12}$ CFU, from about $10^4$ CFU to about $10^{12}$ CFU, from about $10^7$ CFU to about $10^{11}$ CFU, from about $10^8$ CFU to about $10^{10}$ CFU, or from about $10^9$ CFU to about $10^{10}$ CFU of a bacterial species or strain. In some embodiments, such bacterial consortium can also comprise from about $10^7$ CFU to about $10^{10}$ CFU of a bacterial species or strain. In some instances, a bacterial consortium can comprise at least about $10^3$ CFU, $5\times10^3$ CFU, $10^4$ CFU, $5\times10^4$ CFU, $10^5$ CFU, $5\times10^5$ CFU, $10^6$ CFU, $5\times10^6$ CFU, $10^7$ CFU, $5\times10^7$ CFU, $10^8$ CFU, $5\times10^8$ CFU, $10^9$ CFU, $5\times10^9$ CFU, $10^{10}$ CFU, $5\times10^{10}$, CFU, $10^{11}$ CFU, $5\times10^{11}$ CFU, or $10^{12}$ CFU, but no more than about $5\times10^{12}$ CFU of a bacterial species or strain. The bacterial consortia can also comprise from about $10^6$ to about $10^{11}$ CFU per bacterial species or strain. In some cases, the bacterial consortia can comprise from about $10^3$ to about $10^{12}$ CFU per bacterial species or strain. In some instances, the bacterial consortia can comprise from about $10^8$ to about $5\times10^{10}$ CFU per bacterial species or strain. In some instances, the bacterial consortia can comprise from about $10^7$ to about $5\times10^{10}$ CFU per bacterial species or strain. In various embodiments, a bacterial consortium can comprise about $5\times10^8$ CFU per bacterial species or strain. In instances where a pharmaceutical composition is formulated into a unit dose for administration, such CFU values can be per mass unit (e.g., $5\times10^8$ CFU/g) or volume unit (e.g., $5\times10^8$ CFU/mL) of such dosage form.

In some embodiments, the present disclosure provides bacterial consortia that can comprise varying amounts of colony-forming units (CFU) of bacterial cells. Such bacterial consortia can comprise from about $10^3$ CFU to about $10^{12}$ CFU, from about $10^4$ CFU to about $10^{12}$ CFU, from about $10^7$ CFU to about $10^{11}$ CFU, from about $10^8$ CFU to about $10^{10}$ CFU, or from about $10^9$ CFU to about $10^{11}$ CFU of bacterial cells. Such bacterial consortium can also comprise from about $10^3$ CFU to about $10^{12}$ CFU of bacterial cells. In some embodiments, such bacterial consortium can also comprise from about $10^7$ CFU to about $10^{10}$ CFU of bacterial cells. In some instances, a bacterial consortium can comprise at least about $10^3$ CFU, $5\times10^3$ CFU, $10^4$ CFU, $5\times10^4$ CFU, $10^5$ CFU, $5\times10^5$ CFU, $10^6$ CFU, $5\times10^6$ CFU, $10^7$ CFU, $5\times10^7$ CFU, $10^8$ CFU, $5\times10^8$ CFU, $10^9$ CFU, $5\times10^9$ CFU, $10^{10}$ CFU, $5\times10^{10}$, CFU, $10^{11}$ CFU, $5\times10^{11}$ CFU, or $10^{12}$ CFU, but no more than about $5\times10^{12}$ CFU of bacterial cells.

In some embodiments, the present disclosure provides a bacterial population can be present in a total amount of about $10^3$ CFU to about $10^{12}$ CFU of bacterial cells. In some embodiments, a bacterial population can be present in a total amount of at least about $10^3$ CFU, $5\times10^3$ CFU, $10^4$ CFU, $5\times10^4$ CFU, $10^5$ CFU, $5\times10^5$ CFU, $10^6$ CFU, $5\times10^6$ CFU, $10^7$ CFU, $5\times10^7$ CFU, $10^8$ CFU, $5\times10^8$ CFU, $10^9$ CFU, $5\times10^9$ CFU, $10^{10}$ CFU, $5\times10^{10}$, CFU, $10^{11}$ CFU, $5\times10^{11}$ CFU, or $10^{12}$ CFU, but no more than about $5\times10^{12}$ CFU of bacterial cells. In other cases, a bacterial population can be present in a total amount of about $10^7$ CFU to about $10^{10}$ CFU of bacterial cells. In some instances, a bacterial population can be present in a total amount of about $1.5\times10^9$ CFU of bacterial cells.

In some instances, the number of CFU of a bacterial species or strain in a pharmaceutical composition described herein can be a certain fraction of the number of CFU of that bacterial species or strain present in a microbiota of a subject. The microbiota can be a gut or a vaginal microbiota. Such subject can be a human subject. Thus, in some instances, the ratio of CFU of the bacterium in a pharmaceutical composition to the number of CFU of such bacterium in a microbiota can be from about $1:10^4$ to about $1:10$, from about $1:10^3$ to about $1:10$, from about $1:10^2$ to about $1:10$, or from about $1:10$ to about $5:1$. In certain embodiments of this disclosure, such ratio can be at least about 0.0001, 0.0002, 0.0005, 0.001, 0.002, 0.005, 0.01, 0.02, 0.03, 0.04, 0.05, 0.1, 1, 2, 3, 3.5, 4, or 5, but no more than 10.

In some embodiments herein, a bacterial consortium for use in a pharmaceutical composition of this disclosure can comprise or consist of about $5\times10^8$ CFU/mL of any of the bacterial strains *L. crispatus* (DSM 33187), *A. muciniphila* (DSM 33213), and/or *F. prausnitzii* (DSM 33185). In such instances, the bacterial consortium can consist of about $5\times10^8$ CFU/mL of the bacterial strains *L. crispatus* (DSM 33187), *A. muciniphila* (DSM 33213), and *F. prausnitzii* (DSM 33185).

Provided herein are pharmaceutical compositions that can comprise one or more cryoprotectant. Such cryoprotectant can be used to maintain viability of the bacterial cells in a pharmaceutical composition when such composition is frozen or lyophilized, for example, during transport and/or storage prior to use. In some instances, the one or more cryoprotectant can be glycerol, dimethylsulfoxide (DMSO), ethylene glycol, propylene glycol, 2-methyl-2,4-pentanediol, trehalose, sucrose, diethyl glycol, triethylene glycol, polyvinylpyrrolidone (PVP), polyethylene glycol (PEG), saccharose, formamide, glycerol 3-phosphate, proline, methyl alcohol, glucose, bovine serum albumin, polyvinyl alcohol, hydroxyethyl starch, sorbitol, or a combination thereof. Cryoprotectant can comprise an ice blocker. An ice blocker can comprise polyglycerol, polyvinyl alcohol, X-1000 and Z-1000. Such cryoprotectant can be used in a pharmaceutical composition in an amount of about 5, 10, 15, 20, 25, or 30 volume percent (% v/v) or weight percent (% w/w), e.g., depending on whether the pharmaceutical composition is a solid dosage from (e.g., a capsule or tablet) or a liquid dosage from (e.g., a suspension or a gel). Cryoprotectant can also comprise a carbohydrate or an antioxidant. A carbohydrate can comprise trehalose, sucrose, sorbitol, glucose, fructose, saccharose, or a combination thereof.

In some embodiments, pharmaceutical compositions described herein further comprise an antioxidant. In some embodiments, the antioxidant is L-cysteine. In some embodiments, the L-cysteine is present, by weight, in an amount of about 0.001%, 0.005%, 0.01%, 0.05%, 0.1%, 0.5%, 1%, 1.5%, 2%, 5%, 10%, 0.001% to 0.005%, 0.0051% to 0.01%, 0.011% to 0.05%, 0.05% to 0.1%, 0.051% to 0.1%, 0.11% to 0.5%, 0.51% to 1%, 1.1% to 1.5%, 1.5% to 2%, 2.1% to 5%, or 5.1% to 10%. Saccharose can be present, by weight, in an amount of about 0.1%, 0.5%, 1%, 5%, 10%, 15%, 20%, 25%, 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 0.1% to 1%, 1% to 5%, 5% to 10%, 10 to 15%, 15 to 20%, 20 to 25%, 25 to 30%, 30 to 35%, 35 to 40%, 40 to 45%, 45 to 50%, 50 to 55%, 55 to 60%, 60 to 65%, 65 to 70%, 70 to 75%, 75 to 80%, 51 to 61%, 52 to 62%, 53 to 63%, 54 to 64%, 55 to 65%, 56 to 66%, 57 to 67%, 58 to 68%, or 59 to 69%. Trehalose can be present, by weight, in an amount of about 0.01%, 0.05%, 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25%, 0.01% to 15%, 0.1% to 20%, 0.01% to 0.1%, 0.11% to 1%, 1 to 11%, 2 to 12%, 3 to 13%, 4 to 14%, 5 to 15%, 6 to 16%, 7 to 17%, 8 to 18%, 9 to 19%, 10 to 20%, 11 to 21%, 12 to 22%, 13 to 23%, 14 to 24%, or 15 to 25%. Glycerol can be present, by volume, in an amount of about 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 1 to 21%, 2 to 22%, 3 to 23%, 4 to 24%, 5 to 25%, 6 to 26%, 7 to 27%, 8 to 28%, 9 to 29%, 10 to 30%, 11 to 31%, 12 to 32%, 13 to 33%, 14 to 34%, 15 to 35%, 16 to 36%, 17 to 37%, 18 to 38%, 19 to 39%, or 20 to 40%.

In some embodiments herein, the cryoprotectant of a pharmaceutical composition herein is glycerol. Such glycerol can be used in an amount of about 20% v/v in a pharmaceutical composition that can comprise a bacterial consortium of one or more, two or more, or three or more bacterial strains selected from TABLE 1. In some embodiments, the bacteria populations can be lyophilized. A lyophilization process can comprise a low temperature dehydration of the bacterial population. In some embodiments, the lyophilization process can comprise subjecting the bacterial population at low temperature and low pressure.

Provided herein are pharmaceutical compositions that can comprise one or more antioxidant. In some instances, such antioxidant can be used to protect anaerobic bacterial species and/or strain(s) that may be present in the pharmaceutical composition. In such instances, the one or more antioxidant can be used to provide anaerobic conditions during storage and/or transport, and/or to protect the bacterial cells from reactive oxygen species. In some embodiments herein, the antioxidant can be ascorbic acid, dithiothreitol, glutathione, phenolic acids (e.g., gallic, protocatechuic, caffeic, and rosmarinic acids), phenolic diterpenes (e.g., carnosol and carnosic acid), flavonoids (e.g., quercetin and catechin), volatile oils (e.g., eugenol, carvacrol, thymol, and menthol), α-Tocopherol (e.g., vitamin E), Trolox, ascorbic acid, vitamin A, vitamin C, coenzyme Q10, manganese, iodide, melatonin, alpha-carotene, astaxanthin, beta-carotene, canthaxanthin, cryptoxanthin, lutein, lycopene, zeaxanthin, flavonoids (e.g., flavones such as apigenin), luteolin, tangeithin, flavonols, isorhamnetin, kaemferol, myricetin, proanthocyanidins, quercetin, eriodictyol, hesperetin, naringenin, catechin, gallocatechin, epicatechin, epigallocatechin, theaflavine, thearubigins, isoflavone phytoestrogens, daidzein, genistein, glycitein, stilbenoids such as resveratrol, pterostilbene, anthocyanins, cyanidin, delphinidin, malvidin, pelargonidin, peonidin, petunidin, chicoric acid, chlorogenic acid, cinnamic acid, ellagic acid, ellagitannins, gallic acid, gallotannins, rosmarinic acid, curcumin, xanthones, capsaicin, bilirubin, citric acid, oxalic acid, phytic acid, N-acetylcysteine, L-cysteine, L-glutamate, L-proline, R-α-lipoic acid, anthocyanins, copper, cryptoxanthins, flavonoids, indoles, isoflavonoids, lignans, selenium, zinc, or a combination thereof. Such one or more antioxidant(s) can be present in a pharmaceutical composition in an amount of about 0.05%, 0.1%, 0.2%, 0.3%, 0.4%, or 0.5% w/w. L-glutamate can be present, by weight, in an amount of about 0.01%, 0.05%, 0.1%, 0.5%, 1%, 1.5%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, 5%, 5.1%, 5.2%, 5.3%, 5.4%, 5.5%, 5.6%, 5.7%, 5.8%, 5.9%, 6%, 6.1%, 6.2%, 6.3%, 6.4%, 6.5%, 6.6%, 6.7%, 6.8%, 6.9%, 7%, 8%, 9%, 10%, 1 to 5%, 1.1 to 5.1%, 1.2 to 5.2%, 1.3 to 5.3%, 1.4 to 5.4%, 1.5 to 5.5%, 1.6 to 5.6%, 1.7 to 5.7%, 1.8 to 5.8%, 1.9 to 5.9%, 2 to 6%, 2.1 to 6.1%, 2.2 to 6.2%, 2.3 to 6.3%, 2.4 to 6.4%, 2.5 to 6.5%, 2.6 to 6.6%, 2.7 to 6.7%, 2.8 to 6.8%, 2.9 to 6.9%, 3 to 7%, 3.1 to 7.1%, 3.2 to 7.2%, 3.3 to 7.3%, 3.4 to 7.4%, 3.5 to 7.5%, 3.6 to 7.6%, 3.7 to 7.7%, 3.8 to 7.8%, 3.9 to 7.9%, or 4 to 8%. In some case, the cryoprotectant can comprise, by weight, about 60% saccharose, about 10% trehalose, about 1% L-cysteine, and about 4% L-glutamate.

Provided herein are pharmaceutical compositions that can comprise an aqueous buffer solution. Such aqueous medium can be used as the main storage and transport medium for the bacterial cells. As such, the buffer can contain any one or more of bacterial consortium, cryoprotectant, and antioxidant, either dissolved or suspended, to form a pharmaceutical composition as described herein. In some instances, the aqueous buffer solution can be phosphate buffered saline (PBS), HEPES, or Tris buffer, any other suitable buffer, or any combination thereof. In some embodiments, the buffer is PBS and comprises 137 mM NaCl, 2.7 mM KCl, 10 mM $Na_2HPO_4$, and 1.8 mM $KH_2PO_4$. In other cases, the buffer can be PBS and can have a pH of about 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, or 9.

Thus, in some embodiments herein, a pharmaceutical composition comprises a bacterial consortium consisting of about $5 \times 10^8$ CFU of each of the bacterial strains *A. muciniphila* (DSM 33213), *F. prausnitzii* (DSM 33185), and *L. crispatus* (DSM 33187), about 20% v/v glycerol as cryoprotectant, 0.1% w/w L-cysteine as antioxidant, and PBS buffer containing 137 mM NaCl, 2.7 mM KCl, 10 mM $Na_2HPO_4$, and 1.8 mM $KH_2PO_4$. Such pharmaceutical composition can be manufactured and formulated into an orally administrable dosage form using the methods and compositions described herein.

Provided herein are pharmaceutical compositions that can be formulated for administration to a subject. The subject can be a human subject. Administration can include parenteral administration and oral administration. Parenteral administration can include administering a pharmaceutical composition in various non-oral routes, e.g., in the form of a suppository. In various other instances, a pharmaceutical composition described herein can be formulated into an oral dosage from. Such oral dosage form can include a capsule, tablet, emulsion, suspension, syrup, gel, gum, paste, herbal tea, drops, dissolving granules, powders, tablets, lyophilizate, and any other suitable oral dosage forms. A capsule can comprise a plant-derived material. The plant-derived material can comprise a cellulose-based polymer. A capsule can also comprise gelatin; hydroxypropyl methylcellulose (HPMC); starch; hydrolyzed collagen (acid, alkaline, enzymatic, or thermal hydrolysis) from animal origin or cellulose-based; pullulan; tapioca; or any combination thereof. A cellulose-based polymer can comprise pullulan. A capsule can be enteric-coated. An enteric-coated capsule can comprise fatty acids, waxes, shellac, plastics, plant fibers, or any combination thereof. A capsule can have a size of 000, 00, 0, 1, 2, 3, 4, or 5 Empty Pill Capsule Size. A capsule can be starch-free, gluten-free, and preservative-free. >90% of a capsule dissolves in water, pH=1.2 solution, sodium acetate buffer USP (pH=4.5), or sodium phosphate buffer (pH=7.2) within 60 minutes, when measured by the dissolution of acetaminophen when the capsule is filled with unformulated acetaminophen. A capsule can have a disintegration endpoint of about 1.6 minutes, as measured at 37° C. with de-ionized water. A capsule can have a disintegration endpoint of about 0.1, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 3.4, 2.5, 2.6, 2.7, 2.8, 2.9, 3, 3.1, 3.2, 3.3, 3.4, 3.5, 3.6, 3.7, 3.8, 3.9, or 4 minutes, as measured at 37° C. with de-ionized water. A capsule can have a disintegration endpoint of 0.1 to 0.5 minutes, 0.51 to 0.6 minutes, 0.61 to 0.7 minutes, 0.71 to 0.8 minutes, 0.81 to 0.9 minutes, 0.91 to 1 minutes, 1.01 to 1.1 minutes, 1.11 to 1.2 minutes, 1.21 to 1.3 minutes, 1.31 to 1.4 minutes, 1.41 to 1.5 minutes, 1.51 to 1.6 minutes, 1.61 to 1.7 minutes, 1.71 to 1.8 minutes, 1.81 to 1.9 minutes, 1.91 to 2 minutes, 2.01 to 2.1 minutes, 2.11 to 2.2 minutes, 2.21 to 2.3 minutes, 2.31 to 2.4 minutes, 2.41 to 2.5 minutes, 2.51 to 2.6 minutes, 2.61 to 2.7 minutes, 2.71 to 2.8 minutes, 2.81 to 2.9 minutes, 2.91 to 3 minutes, 3.01 to 3.1 minutes, 3.11 to 3.2 minutes, 3.21 to 3.3 minutes, 3.31 to 3.4 minutes, 3.41 to 3.5 minutes, 3.51 to 3.6 minutes, 3.61 to 3.7 minutes, 3.71 to 3.8 minutes, 3.81 to 3.9 minutes, or 3.91 to 4 minutes, as measured at 37° C. with de-ionized water. A capsule can have an oxygen permeability ($cm^3/m^2$/day) of ≤0.5, as measured by a gas composition in the capsule. A capsule can have an oxygen permeability ($cm^3/m^2$/day) of ≤0.0001, ≤0.0005, ≤0.001, ≤0.005, ≤0.01, ≤0.05, ≤0.1, ≤0.5, ≤1, ≤1.5, ≤2, ≤5, or ≤10, as measured by a gas composition in the capsule.

Further provided herein are oral formulations of the pharmaceutical compositions that can be frozen. Such frozen formulations can be administered in a frozen state to a subject, such as a human subject. In some instances, such frozen formulation can be a popsicle, an ice cream, or other frozen formulations.

In various embodiments herein, a pharmaceutical composition of this disclosure can be in a liquid suspension for oral administration to a subject. Such liquid suspension can be aliquoted into certain volumes to provide a unit dose of such oral dosage form. Such unit dose can have a volume of about 0.25, 0.5, 1, 2, 3, 5, or 10 mL. In some instances, the unit dose of a pharmaceutical composition herein has a volume of about 1 mL. Such pharmaceutical composition can comprise a bacterial consortium, a cryoprotectant, an antioxidant, an aqueous buffer solution that can from a liquid cell suspension. Such cell suspension can be tested for quality control to ensure it contains a certain number of metabolically active cells per bacterial strain as described herein.

In some embodiments, provided herein are pharmaceutical compositions formulated into a unit dose for oral administration to a subject. Such oral formulation can comprise or consist of about 5×10^8 CFU of each of the bacterial strains *A. muciniphila* (DSM 33213), *F. prausnitzii* (DSM 33185), and *L. crispatus* (DSM 33187), about 20% v/v glycerol, about 0.1% w/w L-cysteine, and PBS buffer containing 137 mM NaCl, 2.7 mM KCl, 10 mM $Na_2HPO_4$, and 1.8 mM $KH_2PO_4$. Such oral formulation can have a total volume of about 1 mL.

Provided herein are methods for manufacturing the pharmaceutical compositions described herein. In some instances, such pharmaceutical compositions comprise a bacterial consortium comprising one or more bacterial species and/or strains. In some instances, such one or more bacterial strains can include any one or more of *L. crispatus* (DSM 33187), *A. muciniphila* (DSM 33213), and/or *F. prausnitzii* (DSM 33185). Manufacturing of such pharmaceutical compositions can comprise several steps. Such steps can include growth media preparation, inoculation and culture, harvest of the bacterial cells, and assembly of a bacterial consortium by combining the prepared bacterial strain batches for use in a pharmaceutical composition. In some instances, such manufacturing methods can be used for preparation of a pharmaceutical composition for clinical use in human subjects.

Methods of this disclosure for manufacturing bacterial consortia can include media preparation, which can involve dissolving various dry media components such as salts, vitamins, antioxidants, etc., in USP grade water for injection. After complete dissolution, the pH of the media can be adjusted to ensure optimal growth of the respective bacterial cells. The pH adjusted media can then be transferred to a biosafety cabinet and sterilized. In various instances, a microbial consortium herein can comprise one or more anaerobic bacterial strains. In such instances, media can be transferred to an anaerobic chamber containing an atmosphere of about $N_2H_2CO_2$ (90:5:5) to reduce prior to inoculation of anaerobic bacteria.

The manufacturing methods herein can comprise generating a starter culture of the bacterial strains/species. Such methods can include generating a starter culture for the bacterial strains to be included in a pharmaceutical composition by using a certain volume from each flask containing filtered media and transfer such volume to a sterile, pre-reduced screw cap tube, followed by a transfer of thawed bacterial cells using a stock solution from a cell bank that contains the respective bacterial cells. In instances where anaerobic bacterial cells are used, the starter cultures can be grown at about 37° C. for about 12-16 hours under anaerobic conditions. After a certain incubation time period, the starter cultures can be visibly inspected for growth (turbidity) and, upon confirmation of bacterial growth, transferred into additional, larger culture flasks for cell expansion. After incubation for about 12, 18, 24, 30 hours, the cell density and absorbance of the cell culture medium can be measured. Such measurements can be performed by measuring the absorbance at of the cell suspension at 600 nanometers to ensure the absorbance falls within a specified $OD_{600}$ range. Such $OD_{600}$ value or range can be specific a bacterial strain. For example, each bacterial strain shown in TABLE 1 can have a specific $OD_{600}$ value or range. Such $OD_{600}$ range can be from about 0.5 to about 1.5, from about 0.7 to about 1.3, or from about 0.9 to about 1.1. Subsequent to $OD_{600}$ measurements, the bacterial cells can be harvested using various techniques such as centrifugation.

In some instances, for cell harvest, appropriate centrifugation parameters can be selected. For example, in some instances, any of the bacterial strains listed in TABLE 1 can be harvested using parameters that include rotation at about 5,000-10,000×g for about 20-60 mins at about 4° C. to ensure the cells can be separated from a supernatant. Following centrifugation, the resulting cell pellets can be transferred back into an anaerobic environment (e.g., an anaerobic chamber) and the clarified culture supernatant can be completely removed from such pellets using, e.g., a sterile serological pipette. The cell pellets can then be combined by resuspension in a concentrated and pre-reduced cryoprotectant solution. In some instances, such suspension can be about 20-40 times as concentrated as the cell suspension during growth and the pre-reduced cryoprotectant solution can comprise about 20% v/v glycerol or another cryoprotectant. The concentrated cell suspensions can then be dispensed into aliquots, e.g., into pre-reduced, pre-labeled 2 mL screw cap cryovials and transferred to pre-labeled storage boxes at about −70° C. or lower. In instances where such bacterial cells may be used in a pharmaceutical composition, specification testing can be conducted about three days after manufacturing and initial storage at about −70° C. or lower.

Provided herein are methods for manufacturing cell populations or cell batches of one or more species and/or strain(s) for their use in a pharmaceutical composition. In various instances, any of the bacterial strains shown in TABLE 1 can be used in the manufacturing methods described herein. In certain instances, one or more of the strains $L.$ $crispatus$ (DSM 33187), $A.$ $muciniphila$ (DSM 33213), and/or $F.$ $prausnitzii$ (DSM 33185) (TABLE 2) can be used to manufacture cell batches for use in a pharmaceutical composition. In such instances, the present disclosure provided methods for manufacturing such cell batches.

Provided herein are methods for manufacturing $L.$ $crispatus$ (DSM 33187) cell batches that can be used in a pharmaceutical composition described herein. Such methods can comprise preparing a $L.$ $crispatus$ (DSM 33187) cell culture medium. Such culture medium can be a vMRS medium or Boullion vMRS broth. In some instances, such culture medium is not HiMedia vMRS broth. Such culture medium can be specific for a $L.$ $crispatus$ (DSM 33187) strain and can comprise vMRS powder and dipotassium phosphate ($K_2HPO_4$). In some instances, a medium for growing and culturing $L.$ $crispatus$ (DSM 33187) cells can comprise about 250-300 g of vMRS powder and dipotassium phosphate ($K_2HPO_4$). In certain instances, such medium can comprise about 273 g vMRS powder and about 12.5 g dipotassium phosphate ($K_2HPO_4$) and about 4.9 L of water. The pH of such vMRS media can be adjusted to about 6.5±0.1 using, e.g., 5 M hydrochloride solution or glacial acetic acid. The media can then be filtered, reduced to an anaerobic state, and transferred to, e.g., a starter culture tube containing stock $L.$ $crispatus$ (DSM 33187) solution, and incubated at 37° C. for about 16-20 hours. Following incubation and expansion, the absorbance of the cell culture at 600 nm can be determined and repeated in triplicates to ensure absorbance of the cell suspension falls within the range from about 0.8 to about 1.6, preferably of about 1.0-1.4. The contents of the culture flasks can be centrifuged, the residual cell pellets re-suspended in 25 mL of sterile PBS containing an antioxidant and cryoprotectant such as 20% v/v glycerol, and then combined to yield a homogenous cell suspension. The $L.$ $crispatus$ (DSM 33187) cell suspension can be aliquoted, e.g., into cryovials, to achieve a final cell concentration. Such final $L.$ $crispatus$ (DSM 33187) cell concentration can be from about $5×10^8$ to about $10^{10}$ live $L.$ $crispatus$ (DSM 33187) cells per unit dose. Such unit dose can have a volume of about 1 mL. In such instances, the unit dose can comprise about $5×10^8$ live $L.$ $crispatus$ (DSM 33187) cells.

Further provided herein are methods for manufacturing $A.$ $muciniphila$ (DSM 33213) cell batches that can be used in a pharmaceutical composition described herein. Such methods can comprise preparing an $A.$ $muciniphila$ (DSM 33213) cell culture medium. In some instances, such $A.$ $muciniphila$ (DSM 33213) culture medium can be a modified NAGT medium. Such modified NAGT medium can contain soytone or N-acetyl glucosamine (NAG), or both soytone and NAG. In some cases, such modified NAGT medium may not contain magnesium, calcium, glucose, or a combination thereof. In some instances, a modified NAGT medium can provide improved cell growth. Such improved cell growth can be about 30%, 35%, 40%, 45%, or 50% higher compared to cell growth in unmodified NAGT medium.

Thus, in some instance, such NAGT culture medium can be specific for a $A.$ $muciniphila$ strain (DSM 33213) and can comprise any one or more of the ingredients: soytone, pea peptone, yeast extract, sodium bicarbonate ($NaHCO_3$), dibasic potassium phosphate ($K_2HPO_4$), sodium chloride (NaCl), magnesium sulfate (e.g., $MgSO_4×7\ H_2O$), calcium chloride ($CaCl_2$), glucose, N-acetylglucosamine, L-threonine, and/or L-cysteine. In such instances, a volume of about 5 L of a modified NAGT medium for growing and culturing $A.$ $muciniphila$ (DSM 33213) cells can comprise from about 75 g to 100 g of SOLABIA Pea Peptone, from about 75 g to about 85 g of Difco™ Select Soytone, from about 10 g to about 15 g of Bacto™ Yeast Extract, from about 2 g to about 8 g of sodium bicarbonate ($NaHCO_3$), from about 10 g to about 15 g of dibasic potassium phosphate ($K_2HPO_4$), from about 0.5 g to about 5 g of sodium chloride (NaCl), from about 0.5 g to about 5 g of magnesium sulfate heptahydrate ($MgSO_4×7\ H_2O$), from about 0.5 g to about 5 g of calcium chloride ($CaCl_2$), from about 20 g to about 25 g of glucose (dextrose), from about 25 g to about 30 g of N-acetylglucosamine, from about 15 g to about 25 g of L-threonine, and/or from about 2 g to about 8 g of L-cysteine. In one example, a volume of about 5 L of a modified NAGT medium for growing and culturing $A.$ $muciniphila$ (DSM 33213) cells can comprise about 82.5 g SOLABIA Pea Peptone, 82.5 g of Difco™ Select Soytone, about 12.5 g of Bacto™ Yeast Extract, about 5 g of sodium bicarbonate ($NaHCO_3$), about 12.5 g of dibasic potassium phosphate ($K_2HPO_4$), about 1.5 g of sodium chloride (NaCl), about 0.5 g of magnesium sulfate heptahydrate ($MgSO_4×7\ H_2O$), about 0.5 g of calcium chloride ($CaCl_2$), about 22.6 g of glucose (dextrose), about 27.7 g of N-acetylglucosamine, about 20 g of L-threonine, and/or about 5 g of L-cysteine.

The pH of such NAGT media can be adjusted, e.g., to about 6.5±0.1 using, e.g., 5 M hydrochloride solution. The pH of such NAGT media can also be adjusted to about 7. $A.$ $muciniphila$ (DSM 33213) bacterial cells can be added into prepared vials containing such NAGT growth medium. Following incubation for a time period that can be specific for the $A.$ $muciniphila$ (DSM 33213) strain, the absorbance of the cell culture at 600 nm can be measured and recorded to achieve an absorbance value of about 0.5 to about 1.2, preferably about 0.7-1.1. The contents of the culture flasks can then be centrifuged, the supernatants removed, and the residual cell pellets re-suspended in sterile PBS containing an antioxidant and cryoprotectant such as 20% v/v glycerol. The $A.$ $muciniphila$ (DSM 33213) cell suspension can be aliquoted into cryovials to achieve a final $A.$ $muciniphila$ (DSM 33213) cell concentration from about $5×10^8$ to about $10^{10}$ live *A. muciniphila* (DSM 33213) cells per unit dose. Such unit dose can have a volume of about 1 mL. In such instances, the unit dose can comprise about $5 \times 10^8$ live *A. muciniphila* (DSM 33213) cells.

Further provided herein are methods for manufacturing *F. prausnitzii* (DSM 33185) cell batches that can be used in a bacterial consortium of a pharmaceutical composition described herein. Such methods can comprise preparing a complete vitamin mix solution (e.g., YFAP vitamin mix) and a *F. prausnitzii* (DSM 33185) cell culture medium. The YFAP vitamin mix can be specific for the *F. prausnitzii* (DSM 33185) strain and can comprise any one or more of biotin, cobalamin, p-aminobenzoic acid, folic acid, pyridoxamine, thiamine, and/or riboflavin. In such instances, a 1 L volume of the YFAP vitamin mix can comprise about 10 mg of biotin, about 10 mg of cobalamin, about 30 mg of p-aminobenzoic acid, about 50 mg of folic acid, about 150 mg of pyridoxamine, about 50 mg of thiamine, and about 50 mg of riboflavin. All media components can be dissolved, resulting in a solution that is clear and free of solids and precipitates. The YFAP Vitamin mix medium can be filtered and sterilized for use in a *F. prausnitzii* (DSM 33185) culture medium as described below.

Such *F. prausnitzii* (DSM 33185) culture medium can be prepared to comprise any one or more of BBL™ Phytone Peptone, SOLABIA Pea Peptone, Difco™ Select Soytone, Bacto™ Yeast Extract, sodium bicarbonate ($NaHCO_3$), dibasic potassium phosphate ($K_2HPO_4$), sodium chloride (NaCl), magnesium sulfate heptahydrate ($MgSO_4 \times 7\ H_2O$), sodium acetate (NaOAc), glucose (dextrose), sodium propionate, L-cysteine, and/or YFAP Vitamin Mix solution, e.g., prepared as described above. In such instances, a volume of about 5 L of the *F. prausnitzii* (DSM 33185) culture medium can comprise from about 75 g to 100 g of SOLABIA Pea Peptone, from about 45 g to about 55 g of BBL™ Phytone Peptone, from about 45 g to about 55 g of Difco™ Select Soytone, from about 20 g to about 30 g of Bacto™ Yeast Extract, from about 2 g to about 8 g of sodium bicarbonate ($NaHCO_3$), from about 10 g to about 15 g of dibasic potassium phosphate ($K_2HPO_4$), from about 2 g to about 8 g of sodium chloride, from about 0.5 g to about 2 g of magnesium sulfate heptahydrate ($MgSO_4 \times 7\ H_2O$), from about 20 g to about 30 g of sodium acetate (NaOAc), from about 40 g to about 60 g of glucose (dextrose), from about 2 g to about 8 g of sodium propionate, from about 2 g to about 8 g of L-cysteine, and about 0.5 to about 3 mL of YFAP Vitamin Mix solution, e.g., prepared as described above. Thus, in an example, a volume of about 5 L of the *F. prausnitzii* (DSM 33185) culture medium can comprise about 100 g SOLABIA Pea Peptone, 50 g of BBL™ Phytone Peptone, about 50 g of Difco™ Select Soytone, about 25 g of Bacto™ Yeast Extract, about 5 g of sodium bicarbonate ($NaHCO_3$), about 12.5 g of dibasic potassium phosphate ($K_2HPO_4$), about 5 g of sodium chloride, about 1 g of magnesium sulfate heptahydrate ($MgSO_4 \times 7\ H_2O$), about 25 g of sodium acetate (NaOAc), about 50 g of glucose (dextrose), about 5 g of sodium propionate, about 5 g of L-cysteine, and about 1 mL of YFAP Vitamin Mix solution, e.g., prepared as described above.

A *F. prausnitzii* (DSM 33185) culture medium, YFAP-NU, can also be prepared to comprise any one or more of Pea Peptone, NuCel® 783 Yeast Extract, sodium bicarbonate ($NaHCO_3$), dibasic potassium phosphate ($K_2HPO_4$), sodium chloride (NaCl), magnesium sulfate heptahydrate ($MgSO_4 \times 7\ H_2O$), sodium acetate (NaOAc), glucose (dextrose), L-cysteine, and/or cobalamin. In such instances, a volume of about 5 L of the *F. prausnitzii* (DSM 33185) culture medium can comprise from about 75 g to 100 g pea Pea peptone, about 50 g NuCel® 783 Yeast Extract, 5 g sodium bicarbonate ($NaHCO_3$), about 12.5 g dibasic potassium phosphate ($K_2HPO_4$), about 5 g sodium chloride (NaCl), about 1 g magnesium sulfate heptahydrate ($MgSO_4 \times 7\ H_2O$), about 25 g sodium acetate (NaOAc), about 50 g glucose (dextrose), about 5 g L-cysteine, and about 5 g cobalamin.

The pH of such cell media can be adjusted to about 6.5±0.1, e.g., using glacial acetic acid. Such pH may vary from about 6.2 to about 6.8, depending on the bacterial strain used. In some cases, the pH of the cell media may not be regulated. Such pH may vary from about 4.5 to about 7.5. In some embodiment, the pH of such media can be about 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, or 7.5. After reduction to an anaerobic state, starter cultures for *F. prausnitzii* (DSM 33185) can be prepared by adding a certain volume of stock *F. prausnitzii* (DSM 33185) solution, e.g., approximately 500 μL of a cell bank stock solution, to starter culture tubes containing reduced culture medium, followed by incubation at 37° C. for about 12-16 hours. After expansion of the starter culture (e.g., after about 12-24 additional hours of incubation), the absorbance of the cell culture at 600 nm can be determined and repeated in triplicates to ensure absorbance is in a specific range. Such absorbance range can be from about 1.2 to about 2.0, preferably from about 1.4 to about 1.8. The culture flasks can then be centrifuged, the supernatants removed, and the residual cell pellets re-suspended in sterile PBS to yield a homogenous solution. In some instances, the *F. prausnitzii* (DSM 33185) cell suspension can be aliquoted into cryovials (e.g., 2 mL cryovials) to achieve a final *F. prausnitzii* (DSM 33185) cell concentration from about $5 \times 10^8$ to about $10^{10}$ live *F. prausnitzii* (DSM 33185) cells per unit dose. Such unit dose can have a volume of about 1 mL. In such instances, such unit dose can comprise about $5 \times 10^8$ live *F. prausnitzii* (DSM 33185) cells.

The present disclosure also provides methods comprising assembling one or more cell batches of strains to be included in a bacterial consortium for used in a pharmaceutical composition. For example, in some instances, such methods comprise assembling cell populations of one or more bacterial strains of TABLE 1. In such instances, cell batches manufactured for any one or more of the strains *L. crispatus* (DSM 33187), *A. muciniphila* (DSM 33213), and *F. prausnitzii* (DSM 33185) can be combined to form a bacterial consortium for use in a pharmaceutical composition.

Such methods can comprise determining the amount of metabolically active cells in each cell population of a bacterial strain. In instances where the bacterial consortium of a pharmaceutical composition comprises or consists of the three bacterial strains *L. crispatus* (DSM 33187), *A. muciniphila* (DSM 33213), and *F. prausnitzii* (DSM 33185), the number of metabolically active bacterial cells in each of the prepared cell batches can be determined. Such measurements can be performed using any suitable method, e.g., those described herein. The information obtained from such measurements can be used to determine the amount unit doses that can be prepared from a given batch of a bacterial strain (e.g., *L. crispatus* (DSM 33187), *A. muciniphila* (DSM 33213), and/or *F. prausnitzii* (DSM 33185)). For example, the amount of unit doses that can be prepared from a *L. crispatus* (DSM 33187) batch can be determined as follows: number of potential doses from *L. crispatus* (DSM 33187) batch=((*L. crispatus* (DSM 33187) Average Potency in CFU/mL)×(*L. crispatus* (DSM 33187) Batch Volume in mL))/(4×10^8 CFU/dose).

Thus, in some embodiments, a bacterial consortium of a pharmaceutical composition herein can comprise about 5×10^8 CFU per bacterial species or strain. Once the number of potential unit doses that can be generated from each strain has been calculated, the respective vials containing the cells of the respective strain can be removed from the freezer and allowed to pre-reduce in an antechamber prior to proceeding. Subsequent to reduction and thawing, the calculated amounts of cell suspension volumes for each strain can be transferred to a 1 L glass bottle and the volume increased using a buffer such as PBS to arrive at the calculated concentration of cells per milliliter. In some cases, such calculated concentration can be about 5×10^8 CFU/bacterial species/mL of pharmaceutical composition. The resulting homogenous suspension can be aliquoted into unit doses using cryovials and can be stored at −80° C. until further use such as administration to a subject.

The manufacturing methods of a bacterial consortium provided herein can further comprise performing a quality control to ensure the cells of the bacterial strains in the respective composition are viable and correspond to the correct strain(s). In such quality control methods, various parameters, test methods and specifications can be evaluated for each strain batch. Such evaluation can be performed prior to administration of the pharmaceutical composition to a subject. Exemplary quality control parameters can include (i) the concentration of the bacterial strain(s), and (ii) the morphology by visual inspection of colony growth. For example, the morphology of *F. prausnitzii* (DSM 33185) cell colonies can include a circular, entire margin, flat, small-moderate size, cream-tan color; the morphology of *A. muciniphila* (DSM 33213) cell colonies can include a circular, entire margin, raised, punctiform size, opaque-translucent for *A. muciniphila* (DSM 33213) cells; and the morphology of *L. crispatus* (DSM 33187) cell colonies can include a circular, entire margin, raised, small-moderate, white-cream color.

Provided herein are pharmaceutical compositions that can be designed and manufactured to allow storage and/or transport of the pharmaceutical compositions. In some instances, a pharmaceutical composition herein comprising a bacterial consortium can be designed such that the viability of the bacterial cells in the pharmaceutical composition is not or only minimally affected by storage and/or transport. In such instances, the viability of at least about 80%, 85%, 90%, 95%, 97%, or 99% of bacterial cells in the pharmaceutical composition is maintained during storage and/or transport.

In some instances, a pharmaceutical composition herein comprises a cryoprotectant to allow storage at low temperatures at about −70° C. or −80° C. to preserve viability of the bacterial cells. In such instances, the pharmaceutical composition can comprise about 20% v/v glycerol as a cryoprotectant. A pharmaceutical composition herein can further comprise an antioxidant that can preserve an anaerobic environment in the storage or transport vial and can protect the bacterial cells from reactive oxygen species.

In one example, in a pharmaceutical composition herein, live, vegetative bacteria can be preserved frozen in phosphate buffered saline (PBS) with 20% v/v glycerol and 0.1% w/w cysteine to preserve their viability. In such instances, the live bacteria can belong to any one or more of the strains shown in TABLE 1.

The present disclosure provides containers and kits that can be used in combination with the herein described pharmaceutical compositions. The present disclosure further provides instructions that can direct a user (e.g., a human user) to use such containers and kits that comprise the pharmaceutical composition.

In some embodiments, pharmaceutical compositions described herein are present in a container. The container can be used to grow, store, transport, aliquot, and/or administer a pharmaceutical composition of this disclosure. For example, such container can be used to administer a pharmaceutical composition to a subject. In an example, the container is a cryovial and can be used to administer pharmaceutical composition to a human subject. A container described herein can also provide conditions suitable for growth, transport, and/or storage (e.g., cooled or frozen storage) of bacterial populations, e.g., those populations that comprise one or more anaerobic bacterial cells. Such anaerobic bacterial cells can include any one or more of *A. muciniphila* (DSM 33213), *F. prausnitzii* (DSM 33185), and/or *L. crispatus* (DSM 33187) cells. In such cases, a container may be used to provide a certain oxygen content or concentration during growth, transport, and/or storage of a pharmaceutical composition in order to preserve the viability of the bacterial cells. In some instances, a container herein can preserve the viability of at least about 80%, 85%, 90%, 95%, 97%, or 99% of bacterial cells in a pharmaceutical composition. In some instances, a container can preserve the viability of about 95% of bacterial cells for at least about 1 week, 2 weeks, 4 weeks, 8 weeks, or 12 weeks. Containers can further be used to provide suitable volumes, amounts, and dosing schedules for administration of such pharmaceutical composition to a subject. In such instances, a container or kit comprising such container can be designed for self-administration by a human subject. Instructions for such self-administration can be provided as user instructions and can be part of a kit described herein. In various instances, such instructions can be written instructions or oral instructions, or a combination thereof.

In some embodiments, pharmaceutical compositions described herein are present in a container. The container can comprise a 2 mL polypropylene screw cap vial. A vial can be a single dose vial or a multi-dose vial. In some cases, a container can also comprise cyclic olefin copolymer (COC), cyclic olefin polymer (COP), polypropylene, polyethylene (HDPE), ethylene-vinyl alcohol (EVOH)-based material, glass, plastic tubes, jars, aluminum tubes, dispenser tubes, or any combinations thereof. The volume of a vial can be 1/50, 1/10, 1/5, 1/3, 1/2, 5/8, 1, 2, 3, 4, 8, 11, 13, 16, 20, 30, 40, 50 DRAM. The volume of a vial can also be 0.01 ml, 0.05 ml, 0.1 ml, 0.2 ml, 0.3 ml, 0.4 ml, 0.5 ml, 0.6 ml, 0.7 ml, 0.8 ml, 0.9 ml, 1 ml, 1.1 ml, 1.2 ml, 1.3 ml, 1.4 ml, 1.5 ml, 1.6 ml, 1.7 ml, 1.8 ml, 1.9 ml, 2 ml, 2.1 ml, 2.2 ml, 2.3 ml, 2.4 ml, 2.5 ml, 2.6 ml, 2.7 ml, 2.8 rat, 2.9 ml, 3 ml, 3.1 ml, 3.2 ml, 3.3 ml, 3.4 ml, 3.5 ml, 3.6 ml, 3.7 ml, 3.8 ml, 3.9 ml, 4 ml, 4.1 ml, 4.2 ml, 4.3 ml, 4.4 ml, 4.5 ml, 4.6 ml, 4.7 ml, 4.8 ml, 4.9 ml, 5 ml, 5.1 ml, 5.2 ml, 5.3 ml, 5.4 ml, 5.5 ml, 5.6 ml, 5.7 ml, 5.8 ml, 5.9 ml, 6 ml, 6.1 ml, 6.2 ml, 6.3 ml, 6.4 ml, 6.5 ml, 6.6 ml, 6.7 ml, 6.8 ml, 6.9 ml, 7 ml, 7.1 ml, 7.2 ml, 7.3 ml, 7.4 ml, 7.5 ml, 7.6 ml, 7.7 ml, 7.8 ml, 7.9 ml, 8 ml, 8.1 ml, 8.2 ml, 8.3 ml, 8.4 ml, 8.5 ml, 8.6 ml, 8.7 ml, 8.8 ml, 8.9 ml, 9 ml, 9.1 ml, 9.2 ml, 9.3 ml, 9.4 ml, 9.5 ml, 9.6 ml, 9.7 ml, 9.8 ml, 9.9 ml, or 10 ml. The volume of a vial can also be 0.01 to 0.1 ml, 0.11 to 1 ml, 1.1 to 1.11, 1.11 to 1.2, 1.21 to 1.3, 1.31 to 1.4, 1.41 to 1.5, 1.51 to 1.6, 1.61 to 1.7, 1.71 to 1.8, 1.81 to 1.9, 1.91 to 2, 2.01 to 2.1, 2.11 to 2.2, 2.21 to 2.3, 2.31 to 2.4, 2.41 to 2.5, 2.51 to 2.6, 2.61 to 2.7, 2.71 to 2.8, 2.81 to 2.9, 2.91 to 3, 3.01 to 3.1, 3.11 to 3.2, 3.21 to 3.3, 3.31 to 3.4, 3.41 to 3.5, 3.51 to 3.6, 3.61 to 3.7, 3.71 to 3.8, 3.81 to 3.9, 3.91 to 4, 4.01 to 4.1, 4.11 to 4.2, 4.21 to 4.3, 4.31 to 4.4, 4.41 to 4.5, 4.51 to 4.6, 4.61 to 4.7, 4.71 to 4.8, 4.81 to 4.9, 4.91 to 5, 5.01 to 5.1, 5.11 to 5.2, 5.21 to 5.3, 5.31 to 5.4, 5.41 to 5.5, 5.51 to 5.6, 5.61 to 5.7, 5.71 to 5.8, 5.81 to 5.9, 5.91 to 6, 6.01 to 6.1, 6.11 to 6.2 ml, 6.21 to 6.3 ml, 6.31 to 6.4 ml, 6.41 to 6.5 ml, 6.51 to 6.6 ml, 6.61 to 6.7 ml, 6.71 to 6.8 ml, 6.81 to 6.9 ml, 6.91 to 7 ml, 7.01 to 7.1 ml, 7.11 to 7.2 ml, 7.21 to 7.3 ml, 7.31 to 7.4 ml, 7.41 to 7.5 ml, 7.51 to 7.6 ml, 7.61 to 7.7 ml, 7.71 to 7.8 ml, 7.81 to 7.9 ml, 7.91 to 8 ml, 8.01 to 8.1 ml, 8.11 to 8.2 ml, 8.21 to 8.3 ml, 8.31 to 8.4 ml, 8.41 to 8.5 ml, 8.51 to 8.6 ml, 8.61 to 8.7 ml, 8.71 to 8.8 ml, 8.81 to 8.9 ml, 8.91 to 9 ml, 9.01 to 9.1 ml, 9.11 to 9.2 ml, 9.21 to 9.3 ml, 9.31 to 9.4 ml, 9.41 to 9.5 ml, 9.51 to 9.6 ml, 9.61 to 9.7 ml, 9.71 to 9.8 ml, 9.81 to 9.9 ml, or 9.91 to 10 ml.

In some embodiments, pharmaceutical compositions described herein are lyophilized or frozen. Bacterial cells in the lyophilized or frozen pharmaceutical compositions can be stored at −70° C. In some embodiments, the bacterial cells can be stored at 10° C., 4° C., 0° C., −5° C., −10° C., −15° C., −20° C., −25° C., −30° C., −35° C., −40° C., −45° C., −50° C., −55° C., −60° C., −65° C., −70° C., −75° C., or −80° C. In other cases, the bacterial cells can also be stored from −80° C. to −70° C., from −70° C. to −60° C., from −60° C. to −50° C., from −50° C. to −40° C., from −40° C. to −30° C., from −30° C. to −20° C., from −20° C. to −10° C., from −10° C. to 0° C., or from 0° C. to 10° C. In some embodiments, at least 70% of the stored lyophilized or frozen bacterial cells can remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months. In some cases, at least 75% of the stored lyophilized or frozen bacterial cells can remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months. In other cases, at least 80% of the stored lyophilized or frozen bacterial cells can remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months. In some embodiments, at least 85% of the stored lyophilized or frozen bacterial cells can remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months. In other embodiments, at least 90% of the stored lyophilized or frozen bacterial cells can remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months. At least 95% of the stored lyophilized or frozen bacterial cells can also remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months. In some embodiments, at least 99% of the stored lyophilized or frozen bacterial cells can remain viable after 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, or 36 months.

A kit of the present disclosure can provide various components for using a pharmaceutical composition as described herein. Such components can include container(s), test sample(s), and/or equipment for analyzing a pharmaceutical composition, e.g., its viability, pH of the storage medium, etc. Thus, kits of this disclosure can allow for user-friendly, accurate and reliable use of a pharmaceutical composition, including, but not limited to dosing, administration, storage, transport. In some embodiments, the pharmaceutical composition comprises a microbial consortium comprising any one or of the bacterial strain shown in TABLE 2. In such instances, the kit can comprise a pharmaceutical composition comprising at least one, at least two, or all the strains of TABLE 1.

Methods of Treatment

The present disclosure provides methods for using a pharmaceutical composition described herein for the prevention and/or treatment of a disease. Such diseases can include inflammatory diseases, metabolic diseases, or autoimmune diseases. Such diseases can be a result of a dysbiosis or dysbiosis associated conditions in the subject, or allergic Type I hypersensitivity. Such diseases can also include allergic Type II hypersensitivity, allergic Type III hypersensitivity, or allergic Type IV hypersensitivity. Such dysbiosis can be dysbiosis of a gut microbiota of the subject. In some instances, the inflammatory disease is an allergy. In other cases, the inflammatory disease is dermatitis. Such allergy can be allergic asthma, including allergic pediatric asthma, and food allergy. Such metabolic diseases can include obesity, diabetes, or a metabolic syndrome.

Thus, in some instances, a pharmaceutical composition described herein can be formulated for administration to a subject, wherein such subject can have or is suspected of having an allergy. Such subject can be multi-sensitized, e.g., to two or more allergens. Such subject can be a mammal. In some instances, the subject is a human. Such pharmaceutical composition, when administered to a subject such as a rodent or a human, can have anti-inflammatory effect(s) useful in the prevention and/or treatment of inflammatory disease. In some instances, such anti-inflammatory effect(s) can be elicited when the pharmaceutical composition is orally administered.

In some instances, a subject that is treated using a pharmaceutical composition herein that is a human. The human subject can be a neonate, an infant, a toddler, a child, a teenager, or an adult. In some instances, the neonate can be less than about 3 days old, less than about 1 week old, less than about 2 weeks old, less than about 3 weeks old, less than about 4 weeks old, less than about 8 weeks old. In some instances, the infant can be at least about 2 months old, at least 6 about months old, be at least about 12 about months old. In some instances, a pharmaceutical composition can be used to treat a subject that can be between about 2 and about 18 years old, be at least about 18 years old. The subject can be between 2 and 18 years old, or is at least 18 years old. The subject can be between about 2 and about 18 years old, or is at least about 18 (e.g., 19, 20, 25, 30, 40, 50, 60, 70, 80, 90) years old. In some instances, the subject can be between about 2 and about 18 years old, or about 19 years old. The subject can be between about 2 and about 18 years old, or about 19 years old. The subject can be between about 2 and about 18 years old, or about 20 years old. The subject can be between about 2 and about 18 years old, or about 20 years old. The subject can be between about 2 and about 18 years old, or about 25 years old. The subject can be between about 2 and about 18 years old, or about 25 years old. The subject can be between about 2 and about 18 years old, or about 30 years old, or older. The subject can be between about 2 and about 18 years old, or about 30 years old. In some embodiments, the subject is from about 18 years to about 40 years of age, from about 12 years to about 17 years of age, and/or from about 2 years to about 11 years of age. A pharmaceutical composition herein can be mixed with milk breast milk, formula (for nursing an infant), or food for administration.

A pharmaceutical composition herein can be administered for various periods of time according to different administration schedules. A treatment period may vary between subjects and individuals and can depend on various factors as described herein, e.g., disease state, age, etc. In some instances, a subject can be treated for one day to at least about one week, for about a week to about one month, or for about one month to about one year. In such instances, the subject can be treated for about one month, two months, or three months. In some cases, treatment can be performed on consecutive days, consecutive weeks, and/or consecutive months. In some embodiments, a pharmaceutical composition is administered for about 28, 29, or 30 consecutive days.

Methods of treatment herein can include administering a pharmaceutical composition of this disclosure once, two, three, four, five, six, seven, eight, nine, ten, eleven, or twelve times daily. In various instances, a pharmaceutical composition of this disclosure is administered twice daily. Such twice daily administration can be performed in the morning and in the evening. In such cases, there can be a period of about 8, 12, or 16 hours between the first and the second administration of a given day.

In various embodiments herein, the pharmaceutical composition that is administered to a human subject for prevention and/or treatment of an inflammatory disease such as an allergy comprises at least one of the bacterial strains *A. muciniphila* (DSM 33213), *F. prausnitzii* (DSM 33185), and/or *L. crispatus* (DSM 33187) listed in TABLE 1. Such pharmaceutical composition can be administered to a group subjects (e.g., about 10, 20 or 40 subject) of 2-11, 12-17, and 18-40 years of age twice daily for about 28 consecutive days. In such instances, such pharmaceutical composition can be administered in a 1 mL unit dose as a liquid suspension. Such unit dose can be added to cold or room temperature food and drinks for administration.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

EXAMPLES

These examples are provided for illustrative purposes only and not to limit the scope of the claims provided herein.

Example 1: Growth, Isolation, and Characterization of Bacterial Strains

Provided herein are methods for the growth, isolation, and characterization of bacterial strains isolated from a human sample. Such strains may be used as part of a bacterial consortium described herein.

1. Growth of Bacteria

Generally, the procedures for growing bacteria as described herein can be used for culturing obligatory and facultative anaerobic bacterial strains. The bacterial strains in this example were derived from a human fecal sample and were grown on selective media. Upon subculturing, the colonies were transferred to a liquid medium and subsequently prepared for PCR and sequencing. Colonies were also preserved as glycerol stocks.

First, human fecal samples were collected in anaerobic transport media (Anaerobic Systems As-915) or in fecal collection vials sealed within a plastic bag containing an anaerobic atmosphere generating system (e.g., AnaeroPouch Thermo Fisher R686001). All samples were immediately transferred into an anaerobic chamber to minimize transit time and potential oxygen exposure to ensure viability of the anaerobic strains.

Serial dilution tubes were prepared by aliquoting 0.9 mL of PBS+Cys (1×PBS+0.1% w/w L-cysteine) into 13 tubes (with a volume of 1.5 mL). Using a disposable spatula or loop, 20-30 mg of sample was transferred into a first 1.5 mL tube containing 0.9 mL of PBS+Cys. The resulting mixture was vortexed for approximately 30 seconds and 0.1 mL of the resulting, homogenous solution was transferred into the second 1.5 mL tube containing 0.9 mL of PBS+Cys. This step was then repeated until all 13 tubes contained serial dilutions (e.g., $1\text{-}10^{-12}$ dilutions in vials 1-13) of the sample.

Using a disposable hockey stick spreader, ~0.1 mL from the sample tubes containing the dilutions $10^{-5}$ to $10^{-12}$ (vials 6-13) were added to separate agar plates containing the selective agar growth media. The agar plates were then sealed with parafilm to prevent evaporation and placed into an incubator for 72 hours at 37° C. Colonies that fit a colony's (e.g., *L. crispatus* (DSM 33187), *A. muciniphila* (DSM 33213), *F. prausnitzii* (DSM 33185), etc.) specific morphology were identified, and placed on a new, pre-reduced agar plate for isolation. The agar plates were sealed with parafilm and placed into an anaerobic incubator for another 72 hours at 37° C.

The isolated colonies were transferred into liquid media by picking specifically isolated colonies from culture plates and resuspending the colonies in 1 mL of pre-reduced liquid broth. Positive and negative controls of selected organisms are inoculated in parallel to compare for growth and monitor for contamination, respectively. All liquid colony samples are then incubated for 72 hours at 37° C.

Using the positive and negative controls, positive match broth cultures were identified. Glycerol stocks of positive match broth cultures were prepared by transferring 0.75 mL of the broth culture solution into a 2 mL cryotube containing 0.75 mL of 50% v/v glycerol in PBS. Sealed cryotube samples were then removed from the anaerobic chamber and stored at −80° C. The remaining broth culture samples were used for isolate identification using 16S-based PCR as described below.

2. 16S-Based PCR for Isolate Identification

Broth culture samples were centrifuged to form cell pellets and the resulting supernatant is carefully removed to leave the formed cell pellet intact. The cell pellet was then resuspended in 0.5-1 mL ultrapure water.

The PCR Mastermix for a final reaction volume of 50 µL was prepared using the following PCR components (NEB E5000S) and volumes: 10× Buffer (5 µL), 10 mM dNTPs (1 µL), 10 µM 27F Forward Primer (1 µL), 10 µM 1492R Reverse Primer (1 µL), Tag Polymerase (0.25 µL), and sterile water (40.25 µL). The PCR Mastermix (48.5 µL) and 1.5 µL of resuspended bacterial cells were placed into a 0.2 mL PCR strip tube and vortexed before the PCR reaction samples were exposed to the following thermocycler protocol (TABLE 3):

TABLE 3

PCR Thermocycler Protocol.

| Step | Temp | Time |
|---|---|---|
| 1 | 95° C. | 2 min |
| 2 | 95° C. | 30 sec |
| 3 | 50° C. | 30 sec |
| 4 | 68° C. | 1 min 30 sec (30 repeats of steps 2-4) |
| 5 | 72° C. | 5 min |
| 6 | 4° C. | HOLD |

Upon completion of the PCR reactions, samples were submitted for Sanger sequencing using GENEWIZ or a comparable vendor.

3. Characterization of Isolated Bacterial Strains

TABLE 4 below shows short chain fatty acid production, antibiotic resistance, and whole genome sequencing analysis of the strains (also shown in TABLE 2) *Akkermansia muciniphila* (DSM 33213), *Faecalibacterium prausnitzii* (DSM 33185), and *Lactobacillus crispatus* (DSM 33187) that, in various embodiments of this disclosure, can form a bacterial consortium for use in a pharmaceutical composition.

Example 2: Manufacturing of a Bacterial Composition A

Manufacturing conditions were generated to increase yield and growth rate of bacterial strains described herein. In particular, manufacturing conditions for increased yield and growth rate were obtained for the bacterial strains *Akkermansia muciniphila* (DSM 33213), *Faecalibacterium prausnitzii* (DSM 33185), and *Lactobacillus crispatus* (DSM 33187). FIG. 1 herein provides a schematic flow chart summarizing the manufacturing steps for preparing Composition A using these strains.

1. Media Preparation

Animal-free culture media was used in the manufacturing steps of this example. To produce bacterial batches, 5 L of broth media was first prepared for each of the strains. After completely dissolving media components by vigorous stirring for 15 mins in USP grade water, the pH of the media was adjusted with hydrochloric acid. The pH adjusted media was then transferred to a biosafety cabinet and filter sterilized using 0.2 µm vacuum filter units (e.g., using 5 times 1-liter portions). Filter sterilized growth media was immediately transferred to an anaerobic chamber containing an atmosphere of $N_2H_2CO_2$ (90:5:5) and stored with a vented cap for 12-18 hours to reduce prior to inoculation.

2. Inoculum and Culture

After reduction of the media under anaerobic conditions for 12-18 hours, 10 mL from each 1 L filter flask was transferred to a sterile pre-reduced 15 mL screw cap tube and labeled "Sterility Control # of 5". An additional 40 mL of sterile media was transferred to two separate 50 mL Falcon tubes labeled "Starter Culture X of 2". One 2 mL master cell bank (MCB) cryovial was removed from −70° C. storage and the exterior of the vial was cleaned with 70% EtOH and wiped dry with a lint-free wipe. The MCB aliquot was then transferred into the anaerobic chamber and placed in a tube rack to thaw for 5-10 mins. Once completely thawed, a sterile 1 mL filtered pipette tip was used to transfer 500 µL of the thawed 1 mL MCB aliquot into each of the two 40 mL starter cultures. The caps on the inoculated starter culture tubes and sterility control were securely tightened and the controls and starter cultures are grown at about 37° C. for 12-16 hours under anaerobic conditions.

After 12-16 hours, the starter cultures and sterility control were removed from the incubator and visibly inspected for growth (e.g., turbidity). Additionally, lack of visible growth or turbidity was confirmed in the sterility controls prior to

TABLE 4

Isolate Characterization.

| Genus | Species | Strain Designation | Short Chain Fatty Acid Production Analysis | Antibiotic Resistance Analysis | Whole Genome Seq. |
|---|---|---|---|---|---|
| Akkermansia | muciniphila | A. muciniphila (DSM 33213) | Yes | Yes | Yes |
| Faecalibacterium | prausnitzii | F. prausnitzii (DSM 33185) | Yes | Yes | Yes |
| Lactobacillus | crispatus | L. crispatus (DSM 33187) | Yes | Yes | Yes | proceeding. Once confirmed, a sterile 10 mL serological pipette tip was used to carefully transfer 10 mL of the starter culture to each of the five pre-warmed 1 L flasks containing pre-reduced, filter sterilized culture media. The cultures were then incubated for 12-16 hours at 37° C. under anaerobic conditions. After incubation, the turbidity of the cultures was quantified using absorbance spectrometry (Epoch 2 Plate Reader, Biotek) to confirm growth within set parameters. Once the culture absorbance was confirmed to fall within the target $OD_{600}$ range, the cells were harvested by centrifugation.

3. Harvest

Twelve to 18 hours prior to cell harvest, five sterile 1 L centrifuge bottles (Beckman Coulter) with screw cap seals were placed in the anaerobic chamber to allow the bottles to reduce prior to use. After culture growth and validation that cultures fall within target $OD_{600}$ range, the cultures were transferred into sterile 1 L centrifuge bottles. The caps on the centrifuge bottles were tightly sealed to prevent gas exchange and the bottles were transferred to a pre-cooled floor centrifuge containing a 6×1 L rotor. Cells were pelleted at 8,000×g for 30 mins at 4° C. After centrifugation, the cell pellets were transferred back into the anaerobic chamber and the clarified culture supernatant was completely removed from the pellets using a sterile serological pipette. The cell pellets were then combined by resuspension in a 40× concentration in a pre-reduced cryoprotectant solution. The concentrated cell suspensions were then dispensed into 1 mL aliquots in pre-reduced, pre-labeled 2 mL screw cap cryovials and immediately transferred to pre-labeled storage boxes at −70° C. Drug substance strains underwent specification testing three days after manufacturing and initial storage at −70° C.

Described below are production procedures for *A. muciniphila* (DSM 33213), *F. prausnitzii* (DSM 33185), and *L. crispatus* (DSM 33187) cells used in a pharmaceutical composition.

A. Generation of *A. muciniphila* (DSM 33213) Cells for Use in a Pharmaceutical Composition For preparation of the culture medium, in a 5 L beaker, 4.9 L water (for injection) was added before the addition, under mixing, of Difco™ Select Soytone (82.5±0.82 g), Bacto™ Yeast Extract (12.5±0.12 g), Sodium Bicarbonate (NaHCO$_3$) (5±0.05 g), Dibasic Potassium Phosphate (K$_2$HPO$_4$) (12.5±0.12 g), Sodium Chloride (NaCl) (1.5±0.015 g), Magnesium Sulfate Heptahydrate (MgSO$_4$×7 H$_2$O) (0.5±0.05 g), Calcium Chloride (CaCl$_2$) (0.5±0.05 g), Glucose (Dextrose) (22.6±0.22 g), N-acetylglucosamine (27.7±0.27 g), L-Threonine (20±0.2 g), and L-Cysteine (5±0.05 g). The mixture was stirred until all components are fully dissolved, clear and free of solids and precipitates.

The pH of the NAGT media was adjusted to 6.5±0.1. The medium was then vacuum filtered and divided into 5 1 L batches. After the culture media are completely reduced (after approximately 12-16 hours), starter cultures of *A. muciniphila* (DSM 33213) bacterial cells were prepared with a 45 mL volume of medium. *A. muciniphila* (DSM 33213) bacterial cells (approximately 500 μL of stock solution) were removed from the cell bank and added into the prepared vials containing growth medium. The cell suspensions are then allowed to warm and incubated for 24-60 hours in a 37° C. incubator unit, resulting in a turbid/cloudy suspension. Subsequently, the absorbance at 600 nm is measured and recorded in triplicates to achieve a value of about 0.7-1.1.

The culture flasks were then centrifuged using a JLA8.1000 centrifuge at 8000 rpm, for 30 min at 4° C. After the supernatants were removed, the residual cell pellets were re-suspended in 25 mL of sterile PBS-GC (40× concentration of the original culture volume), and then combined to yield a homogenous solution. The *A. muciniphila* (DSM 33213) cell suspension was aliquoted into 2 mL cryovials to achieve a final *A. muciniphila* (DSM 33213) cell concentration of >1×10^9 live *A. muciniphila* (DSM 33213) cells per vial and was stored at −80° C. until further use.

B. Generation of *F. prausnitzii* (DSM 33185) Cells for Use in a Pharmaceutical Composition For preparation of the YFAP Vitamin Mix Solution, a 1 L bottle is filled with water (for injection) followed by the addition, under mixing, of biotin (10±1 mg), cobalamin (10±1 mg), p-aminobenzoic acid (30±1 mg), folic acid (50±1 mg), pyridoxamine (150±1 mg), thiamine (50±1 mg), and riboflavin (50±1 mg). The mixture was stirred until all components were fully dissolved, clear and free of solids and precipitates. Subsequently, the YFAP Vitamin mix medium was filtered and sterilized.

For preparation of the culture medium, in a 5 L beaker, 4.9 L water (for injection) was added before the addition, under mixing, of BBL™ Phytone Peptone (50±0.5 g), Difco™ Select Soytone (50±0.5 g), Bacto™ Yeast Extract (25±0.25 g), sodium bicarbonate (NaHCO$_3$) (5±0.05 g), dibasic potassium phosphate (K$_2$HPO$_4$) (12.5±0.12 g), sodium chloride (NaCl) (5±0.05 g), magnesium sulfate heptahydrate (MgSO$_4$×7 H$_2$O) (1±0.01 g), sodium acetate (NaOAc) (25±0.25 g), glucose (dextrose) (50±0.25 g), sodium propionate (5±0.05 g), L-cysteine (5±0.05 g), and YFAP Vitamin Mix Solution (1 mL, prepared as described above). The mixture was stirred until all components were fully dissolved, clear and free of solids and precipitates.

The pH of the YFAP medium was then adjusted to 6.5 using 5 M hydrochloride solution. The medium was then filtered and allow to stand in the dark for about 12-18 hours for full reduction to an anaerobic state. After a certain volume of medium was transferred to the starter culture tube, approximately 500 μL of the stock *F. prausnitzii* (DSM 33185) solution was transferred into the starter culture tube and incubated at 37° C. for about 12-16 hours. The starter culture tube was evaluated for turbidity and divided into 5 aliquots and added to pre-warmed 1 L flask containing sterile culture media, followed by incubation for 12-16 hours at 37° C.

After incubation, the absorbance at 600 nm was determined and repeated in triplicates to ensure absorbance falls within the range of 1.4-1.8 absorbance. The culture flasks were centrifuged using a JLA8.1000 centrifuge at 8000 rpm, for 30 min at 4° C. After the supernatants were removed, the residual cell pellets were re-suspended in 25 mL of sterile PBS-GC (40× concentration of the original culture volume), and then combined to yield a homogenous solution. The *F. prausnitzii* (DSM 33185) cell suspension was aliquoted into 2 mL cryovials to achieve a final *F. prausnitzii* (DSM 33185) cell concentration of >1×10^9 live *F. prausnitzii* (DSM 33185) cells per vial and was stored at −80° C. until further use.

C. Generation of *L. crispatus* (DSM 33187) Cells for Use in a Pharmaceutical Composition For preparation of the vMRS media, in a 5 L beaker, 4.9 L water (for injection) was added before the addition, under mixing, of 273 g of vMRS powder and dipotassium phosphate ($K_2HPO_4$) (12.5±0.1 g). The mixture was stirred until all components were fully dissolved, clear and free of solids and precipitates.

The pH of the vMRS media was then adjusted to 6.5 with $NH_4OH$ or acetic acid. The medium was then filtered using 0.2 μm vacuum filter units and allow to stand in the dark for about 12-18 hours for full reduction to an anaerobic state. After a certain volume (e.g., 45 mL) of medium was transferred to the starter culture tube, approximately 500 μl of the stock *L. crispatus* (DSM 33187) solution was transferred into the starter culture tube and incubated at 37° C. for about 16-20 hours. The starter culture tube was evaluated for turbidity, divided into 5 aliquots and added to the pre-warmed 1 L flask containing sterile culture media, followed by incubation for 16-20 hours at 37° C.

After incubation, the absorbance at 600 nm was determined and repeated in triplicates to ensure absorbance falls within the range of 1.0-1.4 absorbance. The culture flasks were centrifuged using a JLA8.1000 centrifuge at 8000 rpm, for 20 min at 4° C. After the supernatants were removed, the residual cell pellets were re-suspended in 25 mL of sterile PBS-GC (40× concentration of the original culture volume), and then combined to yield a homogenous solution. The *L. crispatus* (DSM 33187) cell suspension is aliquoted into 1 mL cryovials to achieve a final *L. crispatus* (DSM 33187) cell concentration of >1×10^9 live *L. crispatus* (DSM 33187) cells per vial and was stored at −80° C. until further use.

D. Assembly of Composition A

In order to prepare Composition A that may be used as a bacterial consortium in a pharmaceutical composition described herein, and that includes the three bacterial strains *A. muciniphila* (DSM 33213), *F. prausnitzii* (DSM 33185), and *L. crispatus* (DSM 33187), the number of metabolically active bacterial cells in the finalized cell suspensions stored at −80° C. in cryovials was determined for each strain. The maximum number of potential oral doses that can be produced from the three strain batches can be calculated as follows (TABLE 5):

TABLE 5

Calculation of Potential Doses from Prepared Strain Batches.

| Bacterial strain | Formula |
| --- | --- |
| *A. muciniphila* (DSM 33213) | Number of Potential Doses from *A. muciniphila* (DSM 33213) batch = ((*A. muciniphila* (DSM 33213) Average Potency in CFU/mL) X (*F. prausnitzii* (DSM 33185) Batch Volume in mL))/(1 × 10^9 CFU/dose) |
| *F. prausnitzii* (DSM 33185) | Number of Potential Doses from *F. prausnitzii* (DSM 33185) batch = ((*F. prausnitzii* (DSM 33185) Average Potency in CFU/mL) X (*F. prausnitzii* (DSM 33185) Batch Volume in mL))/(4 × 10^8 CFU/dose) |
| *L. crispatus* (DSM 33187) | Number of Potential Doses from *L. crispatus* (DSM 33187) batch = ((*L. crispatus* (DSM 33187) Average Potency in CFU/mL) X (*L. crispatus* (DSM 33187) Batch Volume in mL))/(4 × 10^8 CFU/dose) |

A full ingredient list for Composition A is provided in TABLE 6:

TABLE 6

Components of Composition A.

| Component | Type | Absolute or relative amount |
| --- | --- | --- |
| Bacterial strain | *A. muciniphila* (DSM 33213) | 5 × 10^8 CFU |
| Bacterial strain | *F. prausnitzii* (DSM 33185) | 5 × 10^8 CFU |
| Bacterial strain | *L. crispatus* (DSM 33187) | 5 × 10^8 CFU |
| Cryoprotectant | Glycerol | 20% (v/v) |
| Antioxidant | L-cysteine | 0.1% (w/w) |
| Buffer | PBS | 0.5-1 mL |

Once the stock vials containing the strain listed in TABLE 6 had been thawed (about 15-20 minutes after removal from freezer), the calculated amounts of cell suspension volumes for each strain were transferred to a 1 L glass bottle and the volume increased using PBS-GC to arrive at the calculated concentration of cells per mL (e.g., 5×10^8 CFU/bacterial species/mL in this example). The resulting homogenous suspension of mixed species drug product was aliquoted into 1 mL volumes into cryovials and stored at −80° C. until further use.

E. Quality Control of Composition A

The following parameters, test methods and specifications were evaluated for each batch of Composition A for quality control purposes as described in TABLE 7.

TABLE 7

Exemplary Quality Control Parameters for Composition A.

| Parameter tested | Assay method used | Result |
| --- | --- | --- |
| Concentration of Viable F. prausnitzii (DSM 33185) | Dilution plating on yBHI Agar for F. prausnitzii | $1 \times 10^8$-$5 \times 10^{10}$ CFU/mL |
| Colony Morphology of F. prausnitzii (DSM 33185) | Visual inspection of colonies growing on yBHI Agar | Circular, entire margin, flat, small-moderate size, cream-tan color. |
| Concentration of Viable A. muciniphila (DSM 33213) | Dilution plating on Mucin Agar for A. muciniphila | $1 \times 10^8$-$5 \times 10^{10}$ CFU/mL |
| Colony Morphology of A. muciniphila (DSM 33213) | Visual Inspection of colonies growing on Mucin Agar | Circular, entire margin, raised, punctiform size, opaque-translucent. |
| Concentration of Viable L. crispatus (DSM 33187) | Dilution plating on MRS Agar for L. crispatus growth | $1 \times 10^8$-$5 \times 10^{10}$ CFU/mL |
| Colony Morphology of L. crispatus (DSM 33187) | Visual Inspection of colonies growing on MRS Agar | Circular, entire margin, raised, small-moderate, white-cream color. |
| Specified Microorganisms (E.coli, C. albicans, Salmonella, S. aureus, P. | Test for objectionable microorganisms according to USP <62> | Absent |
| Bioburden (TAMC/TYMC) | Enumeration of microorganisms according to USP <61> | TAMC < 200, TYMC < 20 |

The test for objectionable microorganisms was performed according to USP<62> using standard protocol. Briefly, the sample was first enriched by inoculating in Soybean Casein Digest Broth (SCDA), or other appropriate neutralizing media, and then streaked onto selective agars for determination of the presence of specified/objectionable microorganisms.

The total number of microorganisms present in a sample was performed according to USP<61> using standard protocol. Such enumeration of microorganisms was carried out using either membrane filtration, pour plating, or the spread plate method.

Example 3: Growth Media Optimization

Provided in this example is an optimization of growth media composition for culturing bacterial strains described herein. In particular, such strains include *Akkermansia muciniphila* (DSM 33213), *Faecalibacterium prausnitzii* (DSM 33185), and *Lactobacillus crispatus* (DSM 33187) for use in a bacterial consortium.

1. *Akkermansia muciniphila* (DSM 33213)

Figure 2:
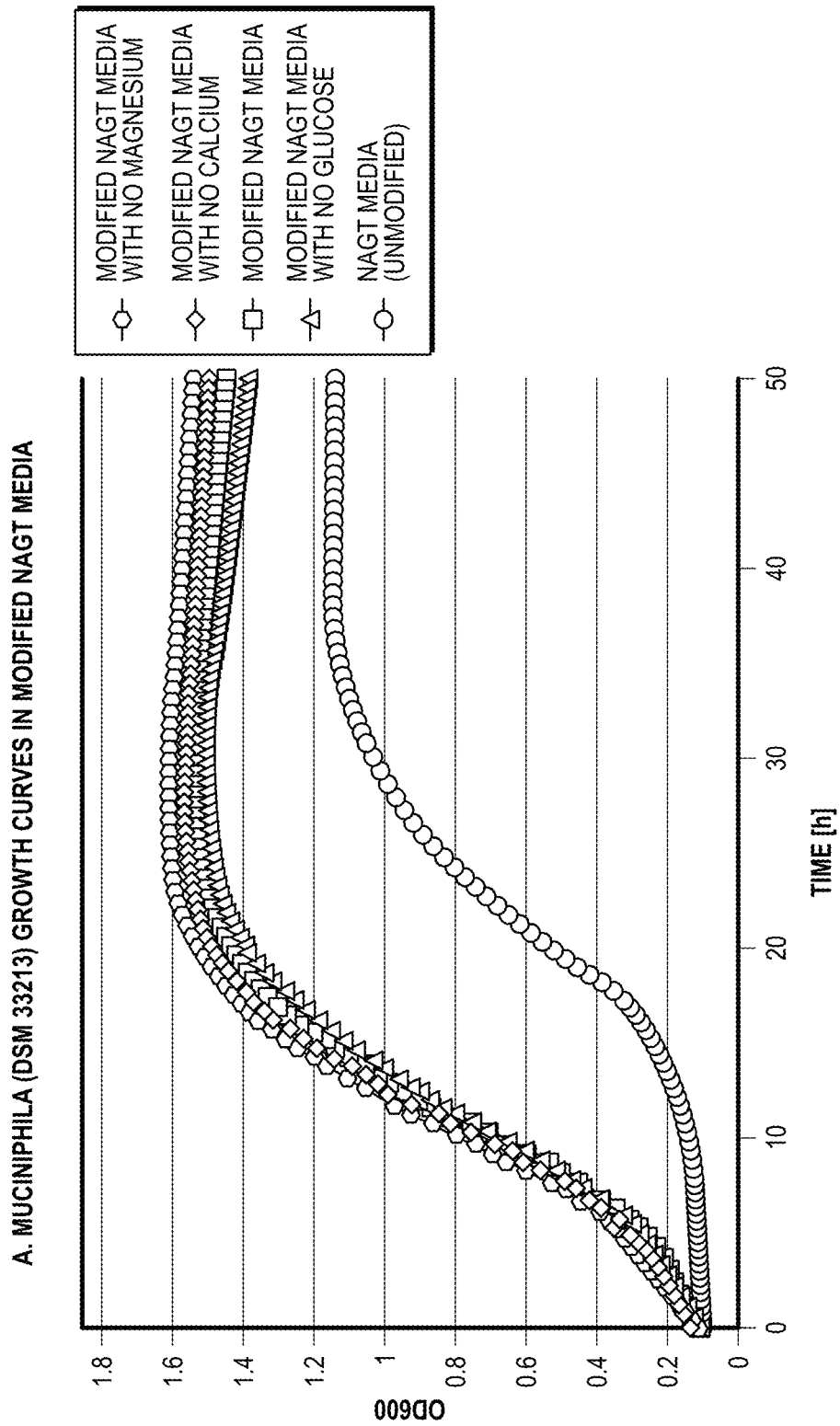
FIG. 2 shows a chart of light absorption at 600 nanometer (also referred to herein as "$OD_{600}$") wavelength versus time for measurement of growth over time for *A. muciniphila* in modified NAGT media. The data is from variation in media that includes: unmodified NAGT media, modified NAGT media, modified NAGT media with no glucose, modified NAGT media with no calcium and modified NAGT media with no magnesium.

Growth of *A. muciniphila* (DSM 33213) cells in N-acetyl-glucosamine threonine (NAGT) media was evaluated at different pH values, along with removing one media component at a time to evaluate the effect of such media components on the growth of *A. muciniphila* (DSM 33213) cells. General NAGT media had a pH of 6.5 and contained 11.9 mM sodium bicarbonate. A ~40% increase in growth (as measured by $OD_{600}$, curve #2, FIG. 2) was observed when *A. muciniphila* (DSM 33213) cells were grown in modified NAGT media with a pH of 7.5 containing 47.6 mM sodium bicarbonate. The increase in biomass was also confirmed by using the plating method. Eliminating glucose (curve #3, FIG. 2), magnesium sulfate (curve #4, FIG. 2) or calcium chloride (curve #5, FIG. 2) from the modified NAGT media showed little to no effect in the growth of *A. muciniphila* (DSM 33213) cells.

Figure 3:
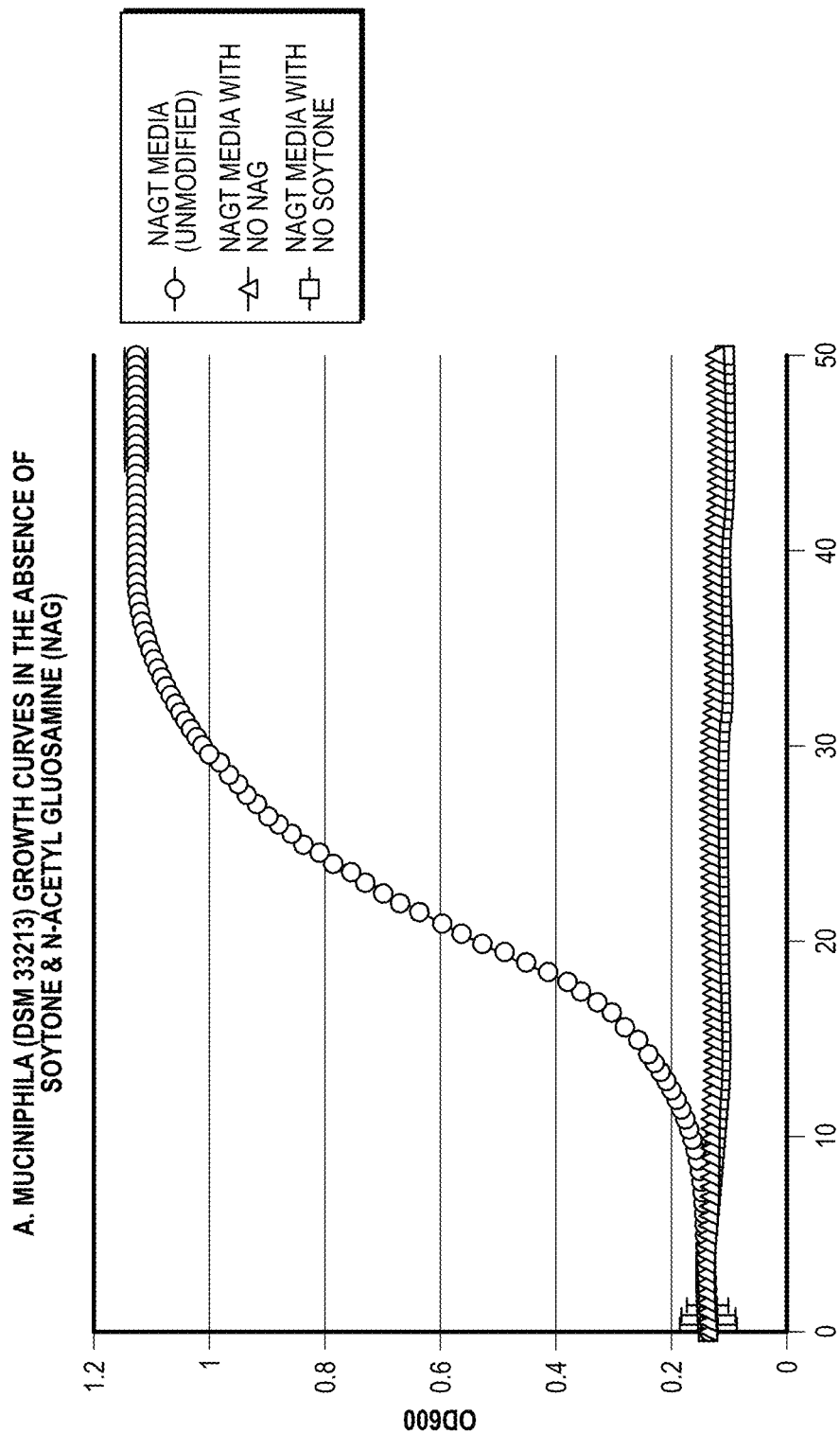
FIG. 3 shows a chart of light absorption at 600 nanometer wavelength versus time for measurement of growth over time for *A. muciniphila* in different NAGT media. The data is from variation in media that includes: unmodified NAGT media, NAGT with no NAG, and NAGT with no soytone.

FIG. 3 shows that soytone and N-acetyl glucosamine (NAG) appear to be necessary for growth of *A. muciniphila* (DSM 33213) cells, as shown by growth curves #2 and #3, respectively, that demonstrate no bacterial growth in media lacking soytone or NAG. Growth curve #1 shows strong growth of *A. muciniphila* (DSM 33213) cells in NAGT media containing both soytone and NAG.

2. *Faecalibacterium prausnitzii* (DSM 33185)

Figure 4:
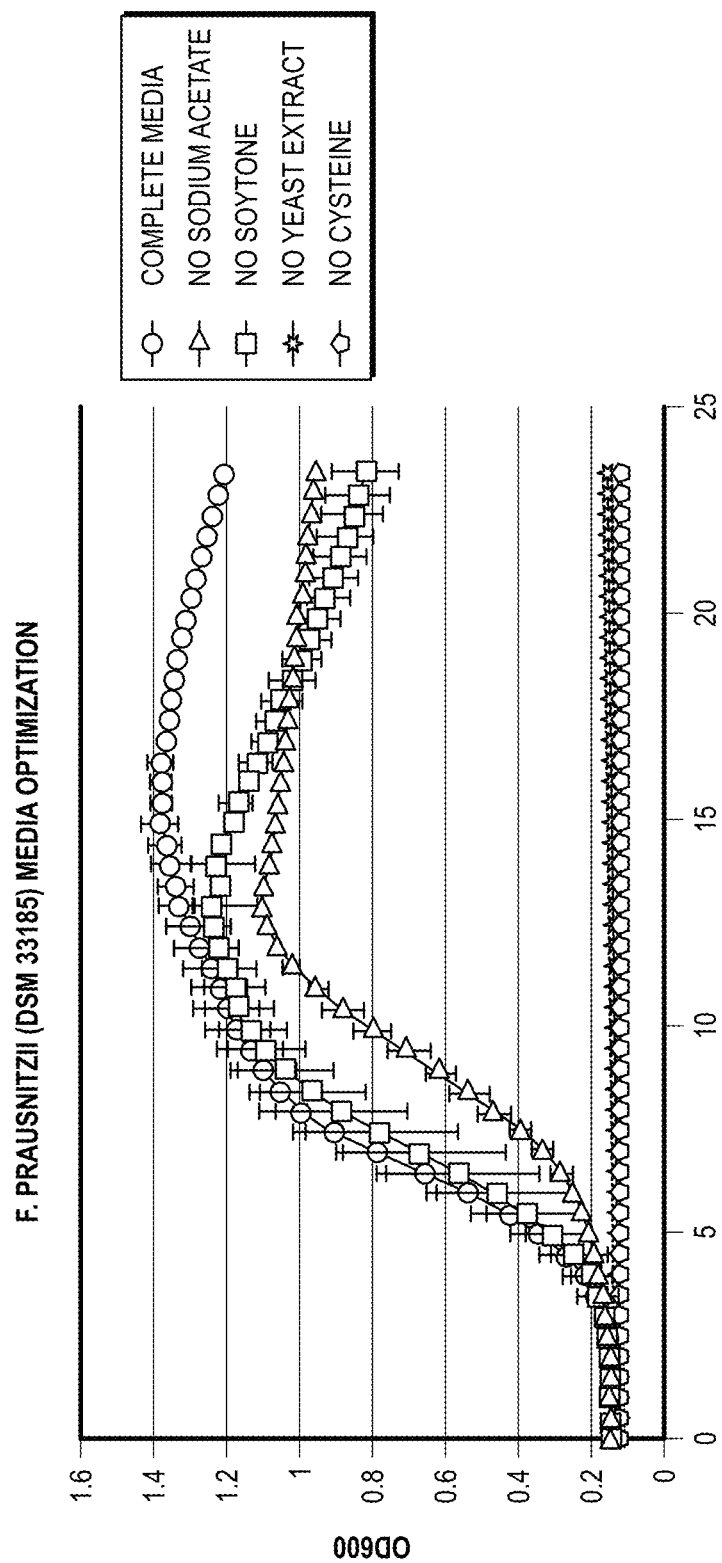
FIG. 4 shows a chart of light absorption at 600 nanometer wavelength versus time for measurement of growth over time for *F. prausnitzii* in different growth media. The data is from variation in media that includes: complete media, media with no sodium acetate, media with no soytone, media with no yeast extract, and media with no cysteine.

The effect of certain components in YFAP medium on the growth of *F. prausnitzii* (DSM 33185) cells was evaluated by removing one media component at a time. For example, FIG. 4 shows that yeast extract (e.g., curve #3 shows FP (DSM 33185) growth in media lacking yeast extract) and cysteine (e.g., curve #4 shows FP (DSM 33185) growth in media lacking yeast extract) appear to be necessary for growth of *F. prausnitzii* (DSM 33185) cells when compared to growth of *F. prausnitzii* (DSM 33185) cells in the complete medium (curve #1). Absence of sodium acetate (curve #5) appears to reduce bit not prevent the growth of *F. prausnitzii* (DSM 33185) cells, whereas absence of soytone (curve #2) appears to lead to cell death during late log and stationary phases.

Figure 5:
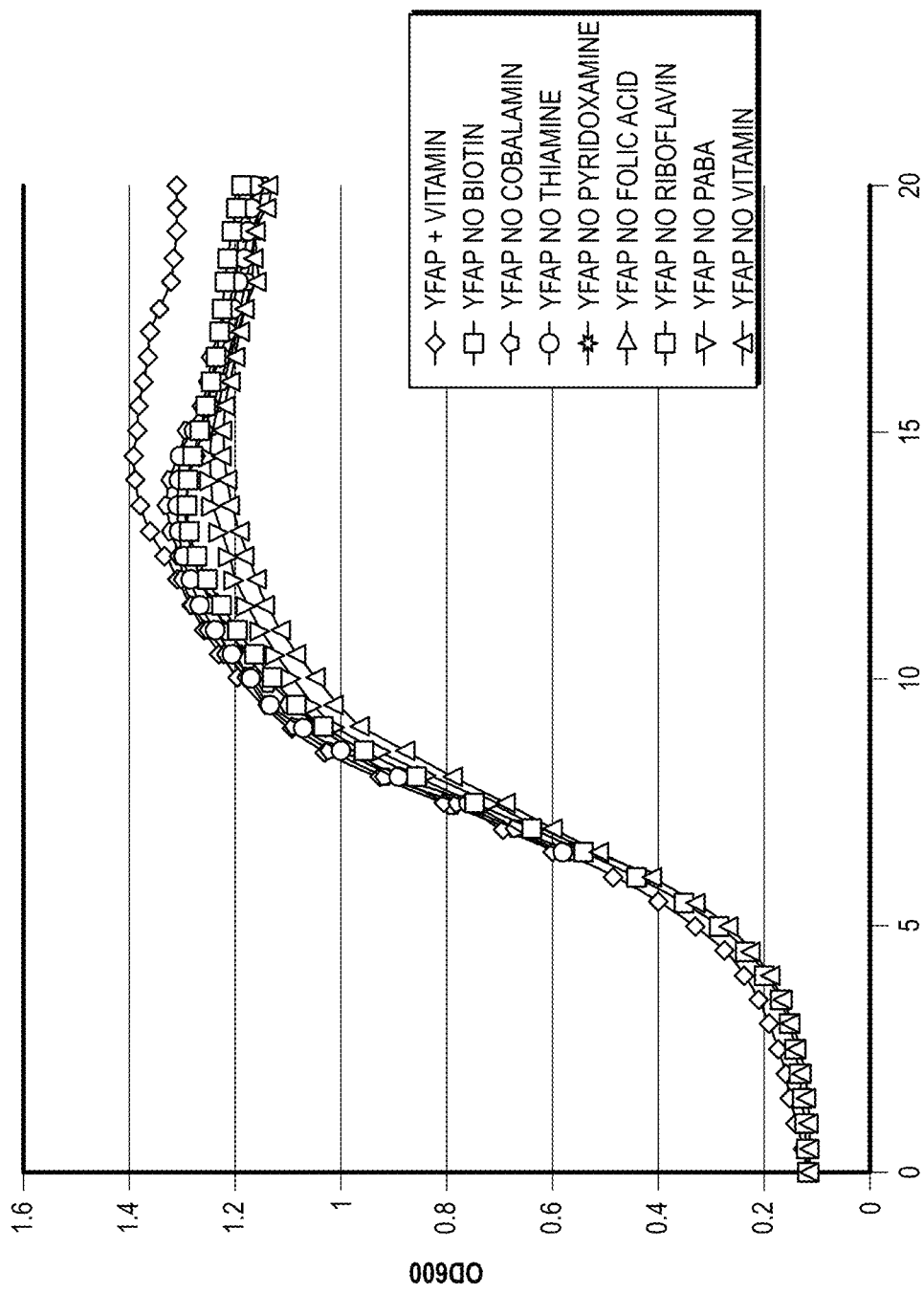
FIG. 5 shows a chart of light absorption at 600 nanometer wavelength versus time for the growth of *F. prausnitzii* (DSM 33185) in YFAP media with different supplements. *F. prausnitzii* was sub-cultured 3 times in YFAP without vitamin before growing in YFAP media with different supplements. The data is from variation in media that includes YFAP media with complete vitamin mix (Vitamin Mix Solution) (YFAP+vitamin), YFAP media without biotin (YFAP No biotin), YFAP media without cobalamin (YFAP No cobalamin), YFAP media without PABA (YFAP No PABA), YFAP media without folic acid (YFAP No folic acid), YFAP media without pyridoxamine (YFAP No pyridoxamine), YFAP media without thiamine (YFAP No thiamine), YFAP media without riboflavin (YFAP No riboflavin), and YFAP media without complete vitamin mix (YFAP No vitamin). Addition of vitamin increased the growth of *F. prausnitzii* by about 10%.

The impact for types of vitamin supplement for the growth *F. prausnitzii* (DSM 33185) cells was also examined. For example, FIG. 5 shows that the addition of vitamins increased the yield of *F. prausnitzii* (DSM 33185) cells sub-cultured three times in YFAP media without vitamins. The final $OD_{600}$ of *F. prausnitzii* (DSM 33185) growing in YFAP with vitamins (YFAP+vitamin) was about 10% higher than those growing in YFAP media lacking thiamine (YFAP No thiamine), pyroxamine (YFAP No pyroxamine), folic acid (YFAP No folic acid), cobalamin (YFAP No cobalamin), PABA (YFAP No PABA), riboflavin (YFAP No riboflavin), vitamins (YFAP No vitamins), or biotin (YFAP No biotin). The YFAP+vitamin media comprises the YFAP media added with a complete vitamin mix solution (e.g., YFAP vitamin mix). The YFAP vitamin comprises about 10 mg/L of biotin, about 10 mg/L of cobalamin, about 30 mg/L of p-aminobenzoic acid, about 50 mg/L of folic acid, about 150 mg/L of pyridoxamine, about 50 mg/L of thiamine, and about 50 mg/L of riboflavin.

Figure 6:
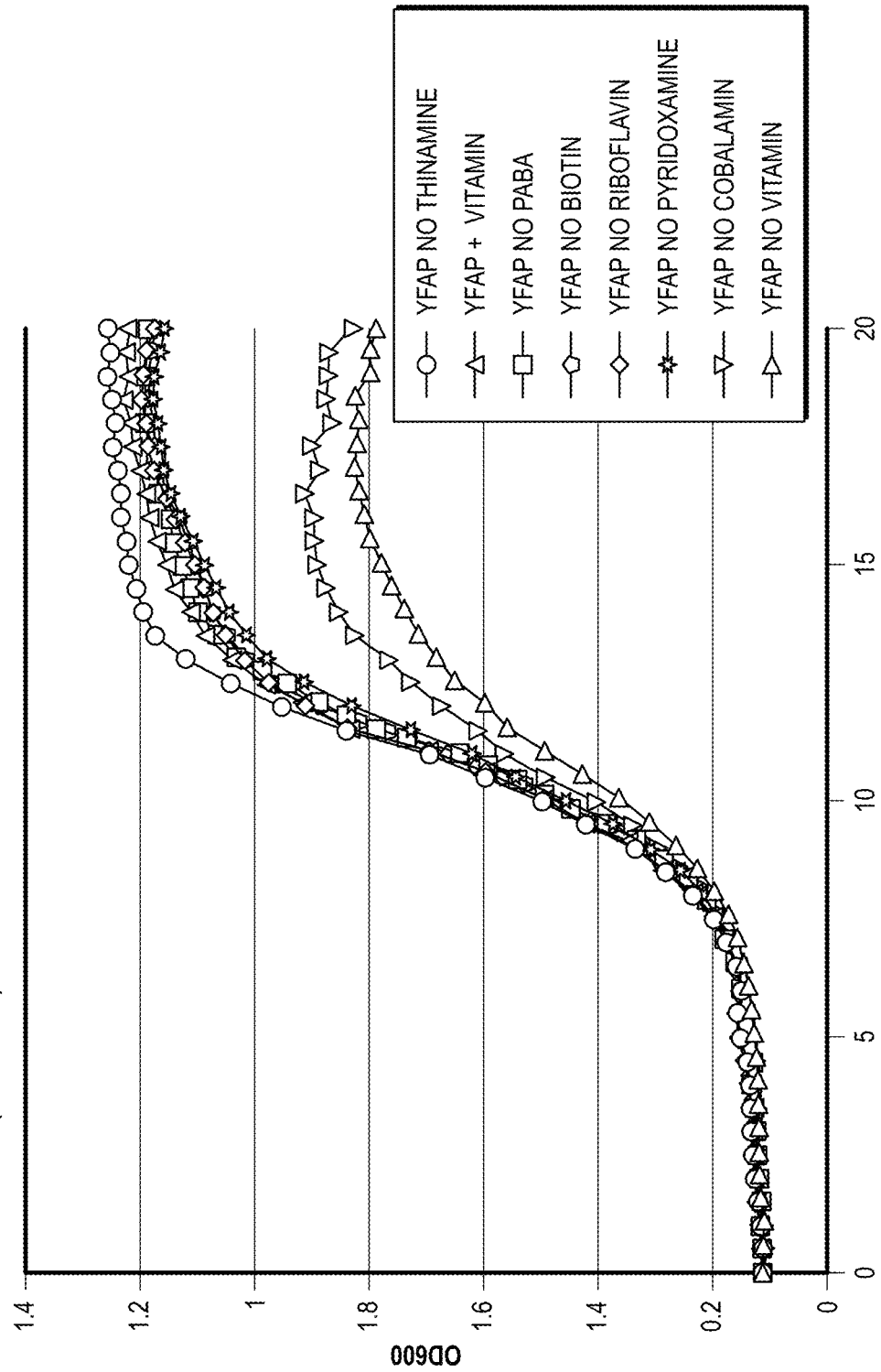
FIG. 6 shows a chart of light absorption at 600 nanometer wavelength versus time for the growth of *F. prausnitzii* (DSM 33185) in YFAP media with different supplements. *F. prausnitzii* was sub-cultured 1 time without vitamin. The data is from variation in media that includes: YFAP media with complete vitamin mix (Vitamin Mix Solution) (YFAP+vitamin), YFAP media without biotin (YFAP No biotin), YFAP media without cobalamin (YFAP No cobalamin), YFAP media without PABA (YFAP No PABA), YFAP media without folic acid (YFAP No folic acid), YFAP media without pyridoxamine (YFAP No pyridoxamine), YFAP media without thiamine (YFAP No thiamine), YFAP media without riboflavin (YFAP No riboflavin), and YFAP media without complete vitamin mix (YFAP No vitamin). The lack of either complete vitamin mix or cobalamin decreased the growth of *F. prausnitzii* by about 30%.

In another example, FIG. 6 shows that cobalamin was a notable factor for the optimal growth of *F. prausnitzii* (DSM 33185) cells sub-cultured one time in YFAP media without vitamins. The final $OD_{600}$ of *F. prausnitzii* (DSM 33185) growing in YFAP lacking cobalamin (YFAP No cobalamin)

was about 30% lower than those growing in YFAP media lacking thiamine (YFAP No thiamine), pyroxamine (YFAP No pyroxamine), folic acid (YFAP No folic acid), PABA (YFAP No PABA), riboflavin (YFAP No riboflavin), biotin (YFAP No biotin) or YFAP media with the addition of vitamins (YFAP+vitamins). The growth disadvantage of YFAP lacking cobalamin was similar to that of YFAP lacking vitamins (YFAP No vitamins).

Figure 7:
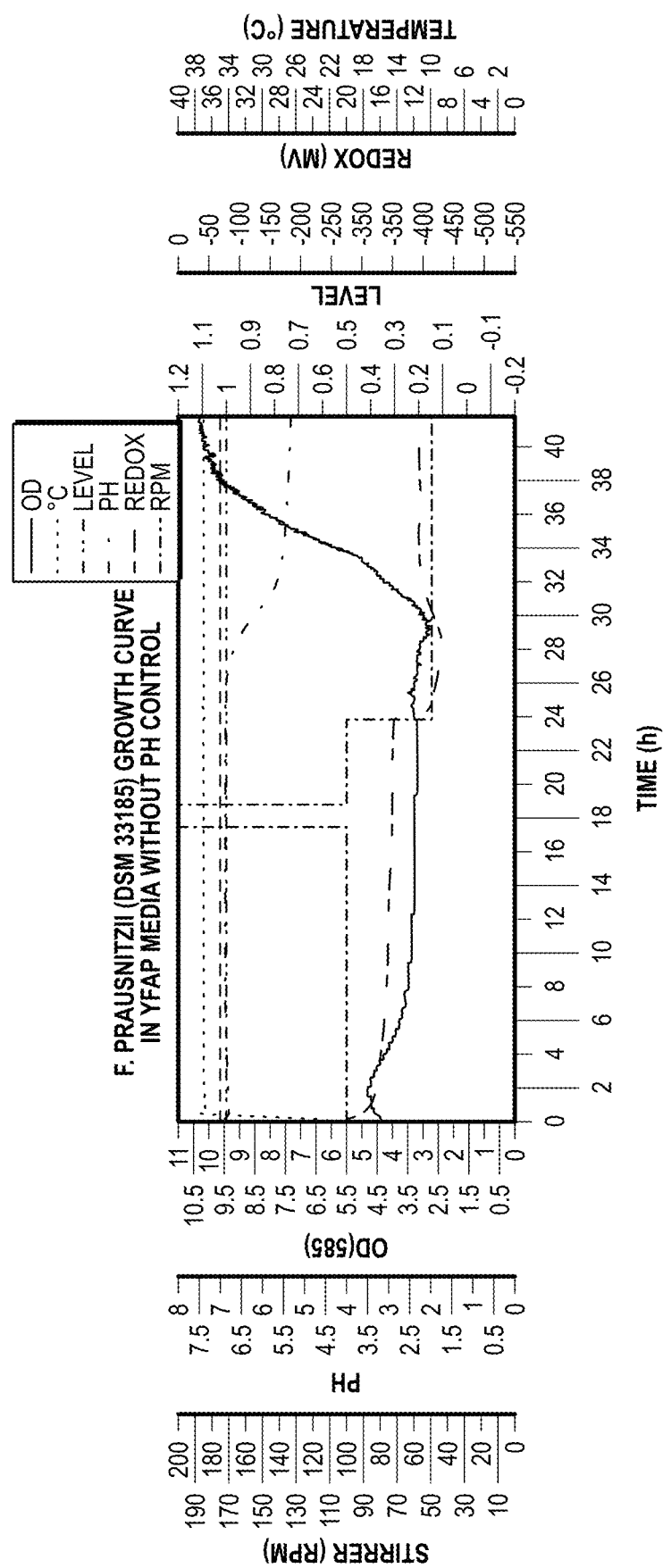
FIG. 7 shows a chart of light absorption at 600 nanometer wavelength versus time for the growth of *F. prausnitzii* (DSM 33185) in YFAP media without pH control. The culture was inoculated at $24^{th}$ hour, stirred at 100 rpm, and incubated at 37° C. When pH was not fixed, it dropped to about 5.5. The redox maintained at −400 mV, and the bacterial growth reached $OD_{600}$=1.1. Any reading before $24^{th}$ hour represents the baseline value for each measurement.
Figure 8:
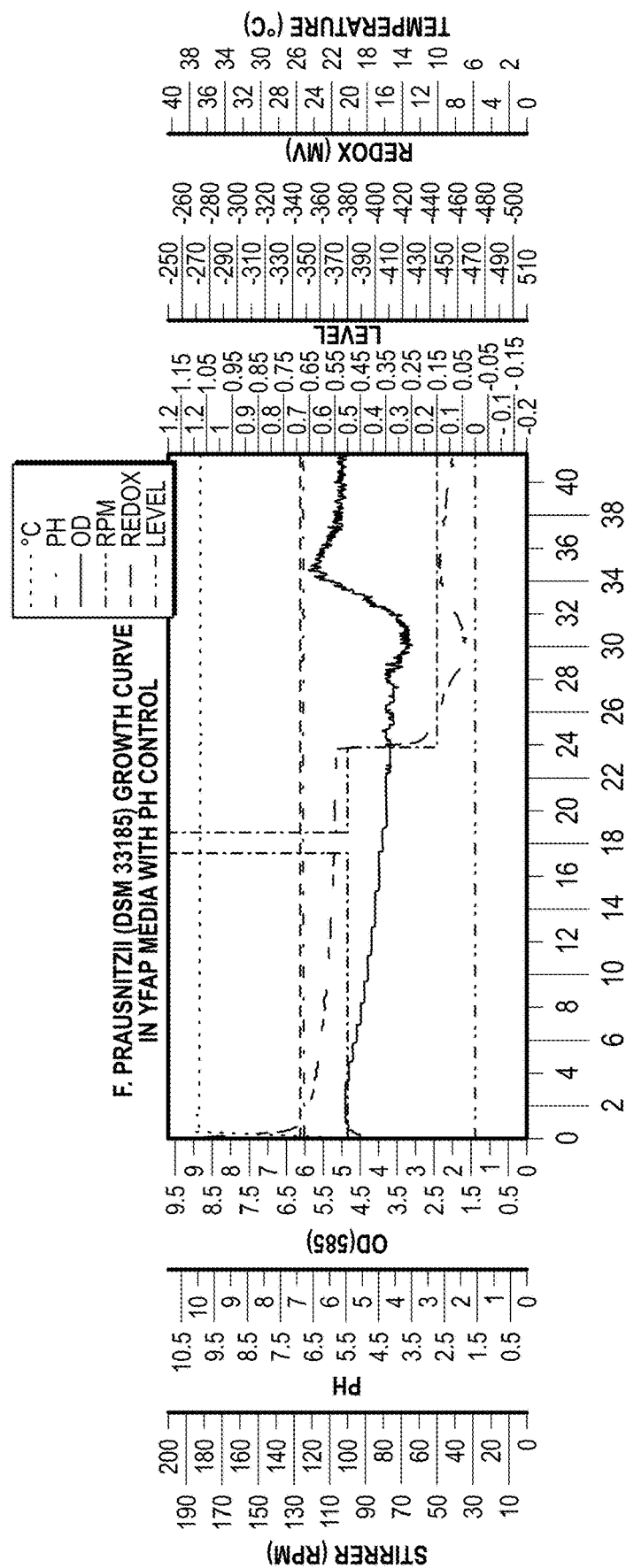
FIG. 8 shows a chart of light absorption at 600 nanometer wavelength versus time for the growth of *F. prausnitzii* (DSM 33185) in YFAP media with pH control. The culture was inoculated at $24^{th}$ hour, stirred at 100 rpm, and incubated at 37° C. When pH was fixed by the addition of ammonium hydroxide ($NH_4OH$) at 6.75, the redox dropped to −460 mV while the bacterial growth plateaued at around $OD_{600}$=0.5. Any reading before $24^{th}$ hour represents the baseline value for each measurement.

The pH of the culture media was also shown to be a notable factor for the growth of F. prausnitzii (DSM 33185) cells. FIG. 7 shows the growth of F. prausnitzii (DSM 33185) cells without pH control while FIG. 8 shows the growth of F. prausnitzii (DSM 33185) cells with pH control. When pH was controlled at 6 with ammonium hydroxide ($NH_4OH$), the redox dropped to −460 mV while the bacterial growth plateaued at around $OD_{600}$=0.5. When pH was not controlled, the redox maintained at −400 mV, and the bacterial growth reached $OD_{600}$=1.1. Therefore, the culture without pH control yielded >50% more bacteria than that with pH control.

3. *Lactobacillus crispatus* (DSM 33187)

Figure 9:
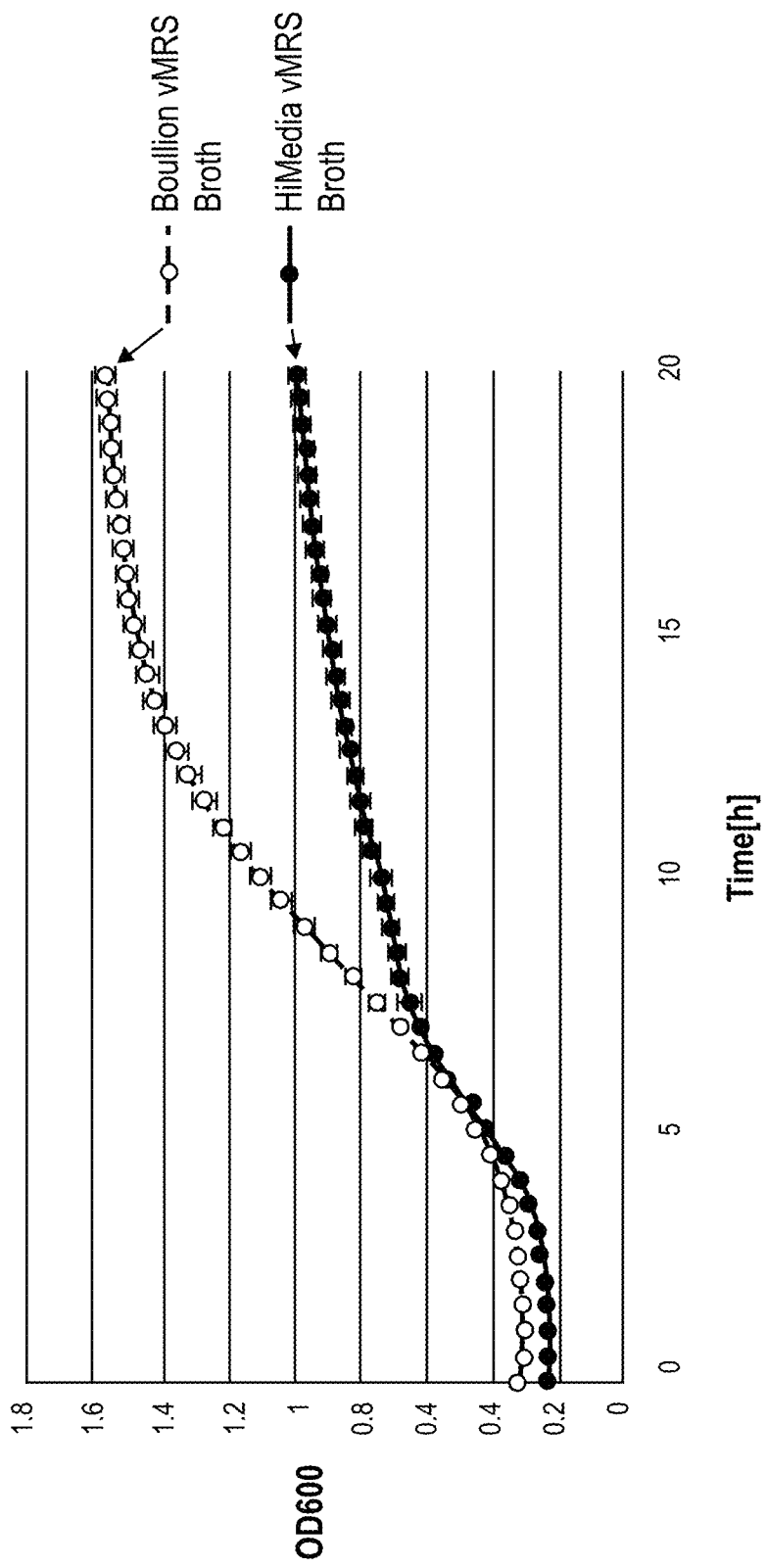
FIG. 9 shows a chart of light absorption at 600 nanometer wavelength versus time of the growth of *L. crispatus* over time in different growth media. The chart compares the growth of *L. crispatus* in Boullion vMRS broth and HiMedia vMRS broth.

*L. crispatus* (DSM 33187) was generally grown in vMRS broth obtained from HiMedia Laboratories. However, FIG. 9 shows that growth of *L. crispatus* (DSM 33187) cells was increased about 55% when media was made with Boullion MRS Vegetal (curve #2) obtained from Biokar diagnostics (Ref: BK176HA) compared to use of HiMedia vMRS broth (curve #1). Without being bound by any theory it is assumed that the observed improvement in cell growth is due to a higher amount (about twice the amount with 20 g/L) of vegetable peptone of the Boullion MRS Vegetal compared to HiMedia vMRS broth.

Example 4: Large-Scale Growth of Bacteria (20 L)

Manufacturing conditions for growing bacteria in 20 L volume of culture were generated to increase yield and growth rate of bacterial strains described herein. In particular, manufacturing conditions for increased yield and growth rate were obtained for the bacterial strains *Akkermansia muciniphila* (DSM 33213), *Faecalibacterium prausnitzii* (DSM 33185), and *Lactobacillus crispatus* (DSM 33187).

Large-Scale Growth of *Akkermansia muciniphila* (DSM 33213)

To prepare the NAGT medium for 1 L inoculum culture and 20 L primary culture, medium components are weighted as followings: pea peptone (16.5 g/L), yeast extract (2.5 g/L), dextrose (4.52 g/L), dibasic potassium phosphate ($K_2HPO_4$) (2.5 g/L), sodium chloride (NaCl) (0.3 g/L), magnesium sulfate heptahydrate ($MgSO_4 \times 7\ H_2O$) (0.1 g/L), sodium bicarbonate ($NaHCO_3$) (1 g/L), calcium chloride (0.1 g/L), N-acetylglucosamine (5.54 g/L), L-threonine (4 g/L), L-cysteine (1 g/L). The mixture was stirred until all components are fully dissolved, clear and free of solids and precipitates.

The pH of the NAGT medium was adjusted to 6.5±0.1 with $NH_4OH$ and acetic acid. The medium was then sterilized by autoclaving at 121° C. for 20 minutes. Glucose and N-acetylglucosamine feed was filter-sterilized separately. The media components were then mixed together.

Inoculum flask containing NAGT was moved to the anaerobic chamber and degassed with $N_2H_2CO_2$ (90:5:5) by incubation under anaerobic atmosphere for 48 hours. Inoculum culture was inoculated from the RCB or MCB (0.4% for *A. muciniphila* (DSM 33213) and incubated under anaerobic atmosphere at 37° C. with no agitation. Culture glucose consumption and optical density were monitored every 2 hours. The culture was stopped if a) a phase of deceleration is observed or b) the culture has been growing for 24 hours.

Figure 10:
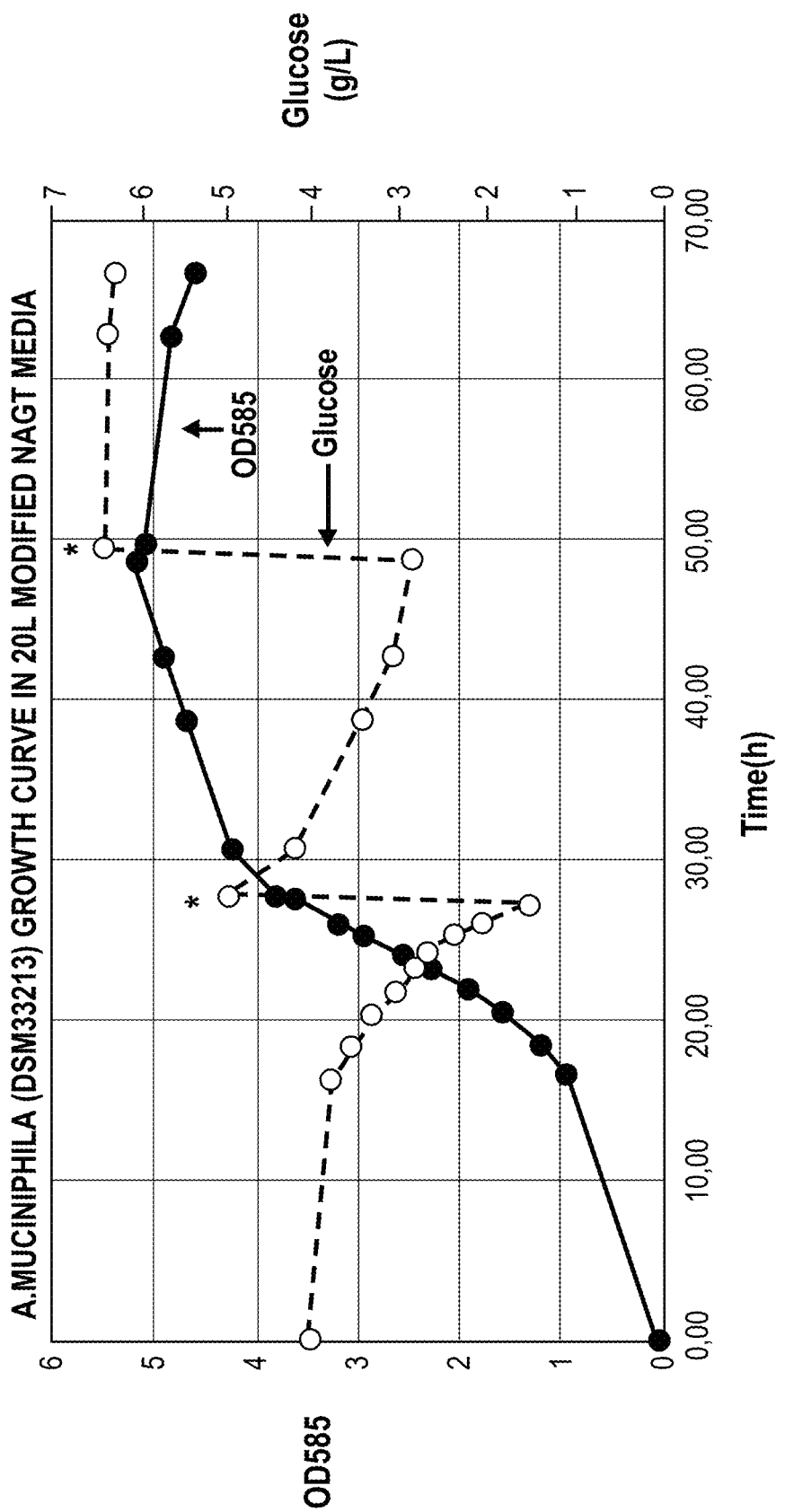
FIG. 10 shows a chart of light absorption at 585 nanometer wavelength (also referred to herein as "$OD_{585}$") (Y-axis on the left) and glucose concentration (g/L) (Y-axis on the right) versus time for the growth of *A. muciniphila* (DSM 33213) 20 liter culture in NAGT media. The chart shows the relationship between the growth of *A. muciniphila* and glucose level over time. The addition (*) of glucose (4.52 g/L) and N-acetylglucosamine (5.54 g/L) at $27^{th}$ and $48^{th}$ hour allowed the *A. muciniphila* culture to maintain in the exponential phase between $25^{th}$ to $50^{th}$ hour and enter the stationary phase after $50^{th}$ hour

20 L media was degassed by sparging using $N_2H_2CO_2$ (90:5:5). Degassing was performed at 6.5 L/min until the redox value dropped and stabilized. Primary culture was inoculated at 5% (eg. ~1 L of inoculum culture), and culture glucose consumption and optical density were monitored every 2 hours. The culture was stirred at 100 rpm and grew at 37° C. As shown in FIG. 10, a feed of 90.4 g of glucose and 110.8 g of N-acetylglucosamine was added at $24^{th}$ hour and $48^{th}$ hour to allow the bacterial culture to maintain in the exponential phase between $25^{th}$ to $50^{th}$ hour and enter the stationary phase after $50^{th}$ hour. The culture was stopped if a) a phase of growth deceleration was observed or b) the culture had grown for about 70 hours.

Large-Scale Growth of *Lactobacillus crispatus* (DSM 33187)

To prepare the Vegitone MRS medium for 1 L inoculum culture and 150 L primary culture, medium components are weighted as followings: pea peptone (20 g/L), yeast extract (10 g/L), dextrose (20 g/L), dibasic potassium phosphate ($K_2HPO_4$) (2.5 g/L), ammonium citrate (0.3 g/L), magnesium sulfate heptahydrate ($MgSO_4 \times 7\ H_2O$) (0.1 g/L), sodium acetate (NaOAc) (5.54 g/L), Tween 80 (4 g/L). The mixture was stirred until all components are fully dissolved, clear and free of solids and precipitates.

The pH of the Vegitone MRS medium was adjusted to 6.5±0.1 with $NH_4OH$ or acetic acid. The medium was then sterilized by autoclaving at 121° C. for 20 minutes. Glucose sugar solution was filter-sterilized. The media components were then mixed together.

Inoculum flask containing Vegitone MRS was moved to the anaerobic chamber and degassed with $N_2H_2CO_2$ by incubation under anaerobic atmosphere for 48 hours. Inoculum culture was inoculated from the RCB or MCB (0.4% for *L. crispatus* (DSM 33187) and incubated under anaerobic atmosphere at 37° C. with no agitation. Culture glucose consumption and optical density were monitored every 2 hours. The culture was stopped if a) a phase of deceleration is observed or b) the culture has been growing for 24 hours.

Figure 11:
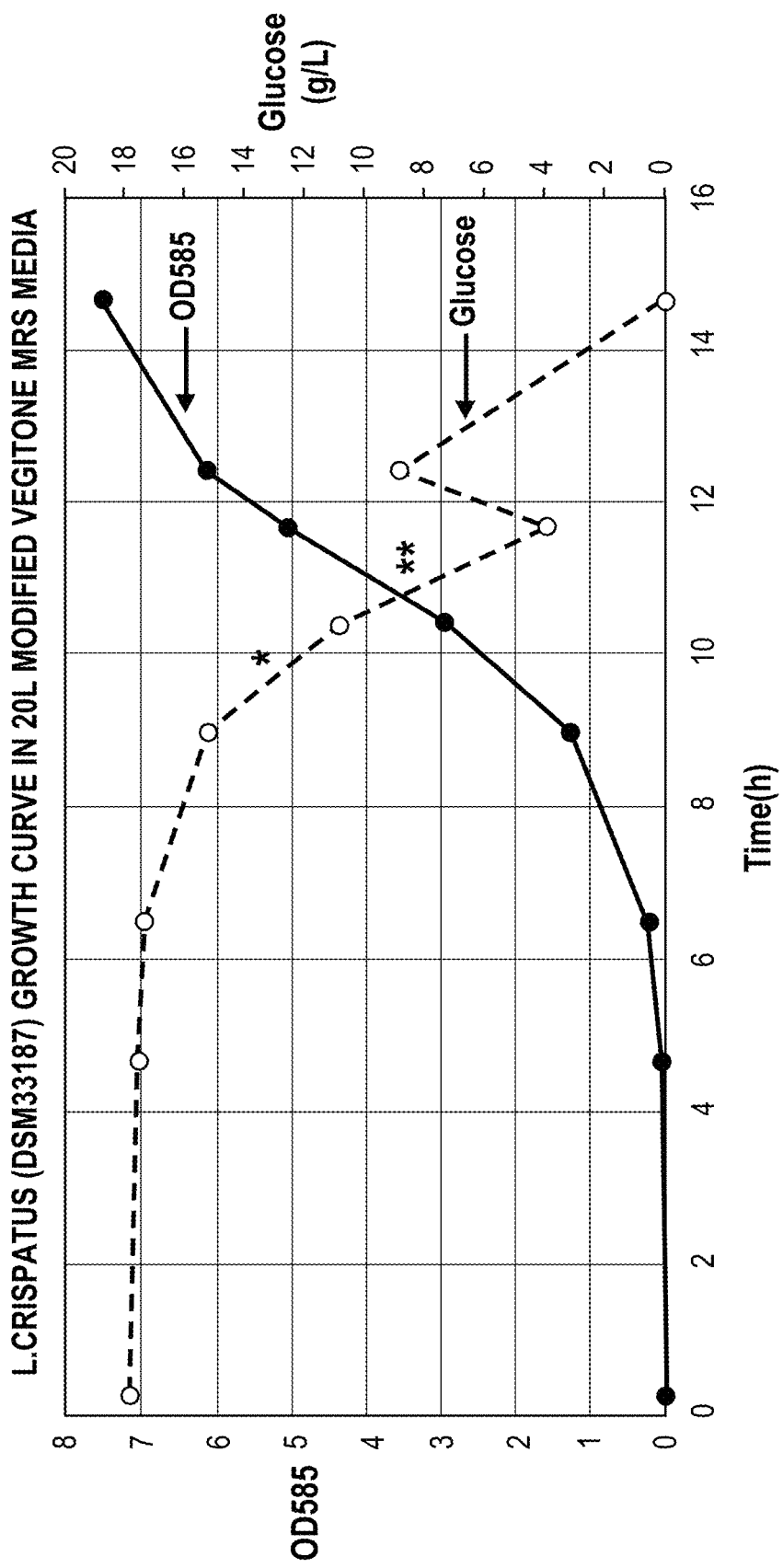
FIG. 11 shows a chart of light absorption at 585 nanometer wavelength (Y-axis on the left) and glucose concentration (g/L) (Y-axis on the right) versus time for the growth of *L. crispatus* (DSM 33187) 20 liter culture in Vegitone MRS media. The chart shows the relationship between the growth of *L. crispatus* (DSM 33187) and glucose level over time. The two additions ($1^{st}$ feed * and $2^{nd}$ feed **) of glucose (10 g/L) at $10^{th}$ and $11^{th}$ hour allowed the *L. crispatus* culture to maintain in the exponential phase between $11^{th}$ to $14^{th}$ hour and enter the stationary phase after $14^{th}$ hour.

20 L media was degassed by sparging using $N_2H_2CO_2$ (90:5:5). Degassing was performed at 6.5 L/min until the redox value dropped and stabilized. Primary culture was inoculated at 1% (eg. ~200 mL of inoculum culture), and culture glucose consumption and optical density were monitored every 2 hours. The culture was stirred at 100 rpm and grew at 37° C. As shown in FIG. 11, a feed of 200 g of glucose was added at the $10^{th}$ hour and $11^{th}$ hour to allow bacterial culture to maintain in the exponential phase between $11^{th}$ to $14^{th}$ hour and enter the stationary phase after $14^{th}$ hour. The culture was stopped if a) a phase of growth deceleration was observed or b) the culture had grown for 16 hours.

Large-Scale Growth of *Faecalibacterium* Prausnitzii (DSM 33185)

To prepare the YFAP medium for 1 L inoculum culture and 20 L primary culture, media components are weighted as followings: pea peptone (20 g/L), yeast extract (5 g/L), dextrose (10 g/L), dibasic potassium phosphate ($K_2HPO_4$) (2.5 g/L), sodium chloride (NaCl) (1 g/L), magnesium sulfate heptahydrate ($MgSO_4 \times 7\ H_2O$) (0.2 g/L), sodium bicarbonate ($NaHCO_3$) (1 g/L), sodium acetate NaOAc) (5 g/L), L-cysteine (1 g/L). YFAP Vitamin Mix Solution was prepared as described in Example 3. The mixture was stirred until all components are fully dissolved, clear and free of solids and precipitates.

The pH of the YFAP media was adjusted to 6.5±0.1 with NaOH. The medium was then sterilized by autoclaving at 121° C. for 20 minutes. Glucose and YFAP Vitamin Mix Solution were filter sterilized (0.2 μm filter). The medium components were then mixed together.

Inoculum flask containing YFAP was moved to the anaerobic chamber and degassed with $N_2H_2CO_2$ by incubation under anaerobic atmosphere for at least 16 hours. Inoculum culture was inoculated from the Research Cell Bank (RCB) or Master Cell Bank (MCB) (0.4% for *F. prausnitzii* (DSM 33185) and incubated under anaerobic atmosphere at 37° C. with no agitation. Culture glucose consumption and optical density were monitored every 2 hours. The culture was stopped after the culture has been grown for 10-16 hours.

Figure 12:
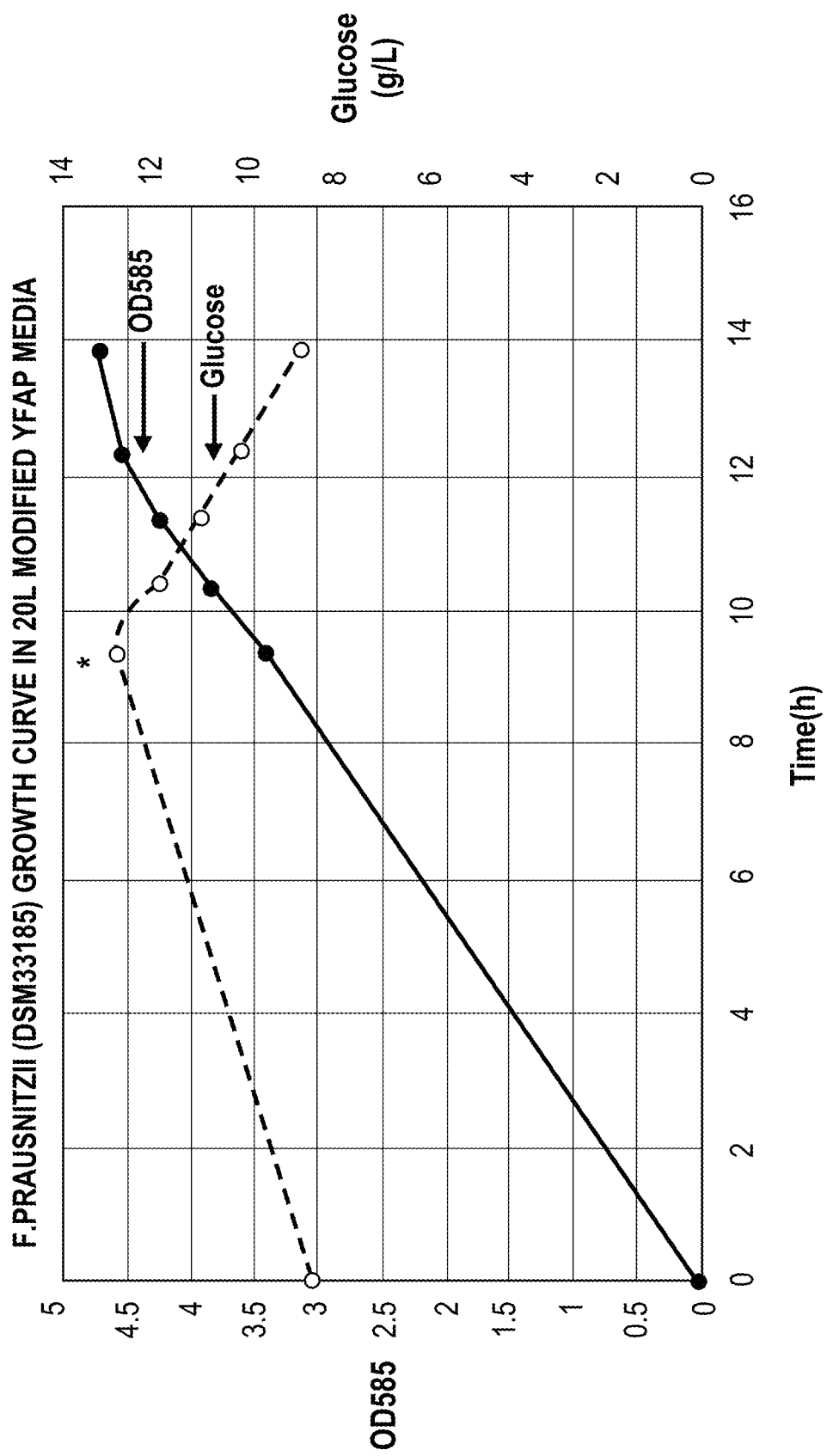
FIG. 12 shows a chart of light absorption at 585 nanometer wavelength (Y-axis on the left) and glucose concentration (g/L) (Y-axis on the right) versus time for the growth of *F. prausnitzii* (DSM 33185) 20 liter culture in FAP media. The chart shows the relationship between the growth of *F. prausnitzii* (DSM 33185) and glucose level over time. The addition (1$^{st}$ feed *) of glucose (10 g/L) at 9$^{th}$ hour allowed the *F. prausnitzii* culture allow the cell to maintain growth from 9$^{th}$ to 14$^{th}$ hour.

All open vessel operations were performed in either the Biological Safety Cabinet (BSC) or Anaerobic Chamber (AC) using good aseptic techniques. 20 L medium was degassed by sparging using $N_2H_2CO_2$ (90:5:5). Degassing was performed at 6.5 L/min until the redox value dropped and stabilized. Primary culture was inoculated at 1% (e.g., —200 mL of inoculum culture), and culture glucose consumption and optical density were monitored every 2 hours. The culture was stirred at 100 rpm and grew at 37° C. As shown in FIG. 12, a feed of 200 g of glucose was added at $9^{th}$ hour to allow the cell to maintain growth from $9^{th}$ to $14^{th}$ hour. The culture was stopped if a) a phase of growth deceleration was observed or b) the culture had grown for 16 hours Example 5: Large-Scale Growth of Bacteria (150 L)

Manufacturing conditions for growing bacteria in 150 L volume of culture were generated to increase yield and growth rate of bacterial strains described herein. In particular, manufacturing conditions for increased yield and growth rate were obtained for the bacterial strains *Akkermansia muciniphila* (DSM 33213), *Faecalibacterium prausnitzii* (DSM 33185), and *Lactobacillus crispatus* (DSM 33187).

Large-Scale Growth of *Akkermansia muciniphila* (DSM 33213)

To prepare the NAGT medium for 1 L inoculum culture and 150 L primary culture, medium components are weighted as followings: pea peptone (16.5 g/L), yeast extract (2.5 g/L), dextrose (4.52 g/L), dibasic potassium phosphate ($K_2HPO_4$) (2.5 g/L), sodium chloride (NaCl) (0.3 g/L), magnesium sulfate heptahydrate ($MgSO_4 \times 7H_2O$) (0.1 g/L), sodium bicarbonate ($NaHCO_3$) (1 g/L), calcium chloride (0.1 g/L), N-acetylglucosamine (5.54 g/L), L-threonine (4 g/L), L-cysteine (1 g/L). The mixture was stirred until all components are fully dissolved, clear and free of solids and precipitates.

The pH of the NAGT medium was adjusted to 6.5±0.1 with $NH_4OH$ or acetic acid. The medium was then sterilized by autoclaving at 121° C. for 20 minutes. Glucose was filter sterilized (0.2 μm). The media components were then mixed together.

Inoculum flask containing NAGT was moved to the anaerobic chamber and degassed with $N_2H_2CO_2$ by incubation under anaerobic atmosphere for 48 hours. Inoculum culture was inoculated from the RCB or MCB (0.4% for *A. muciniphila* (DSM 33213) and incubated under anaerobic atmosphere at 37° C. with no agitation. Culture glucose consumption and optical density were monitored every 2 hours. The culture was stopped if a) a phase of deceleration is observed or b) the culture had been growing for 48 hours.

Figure 13:
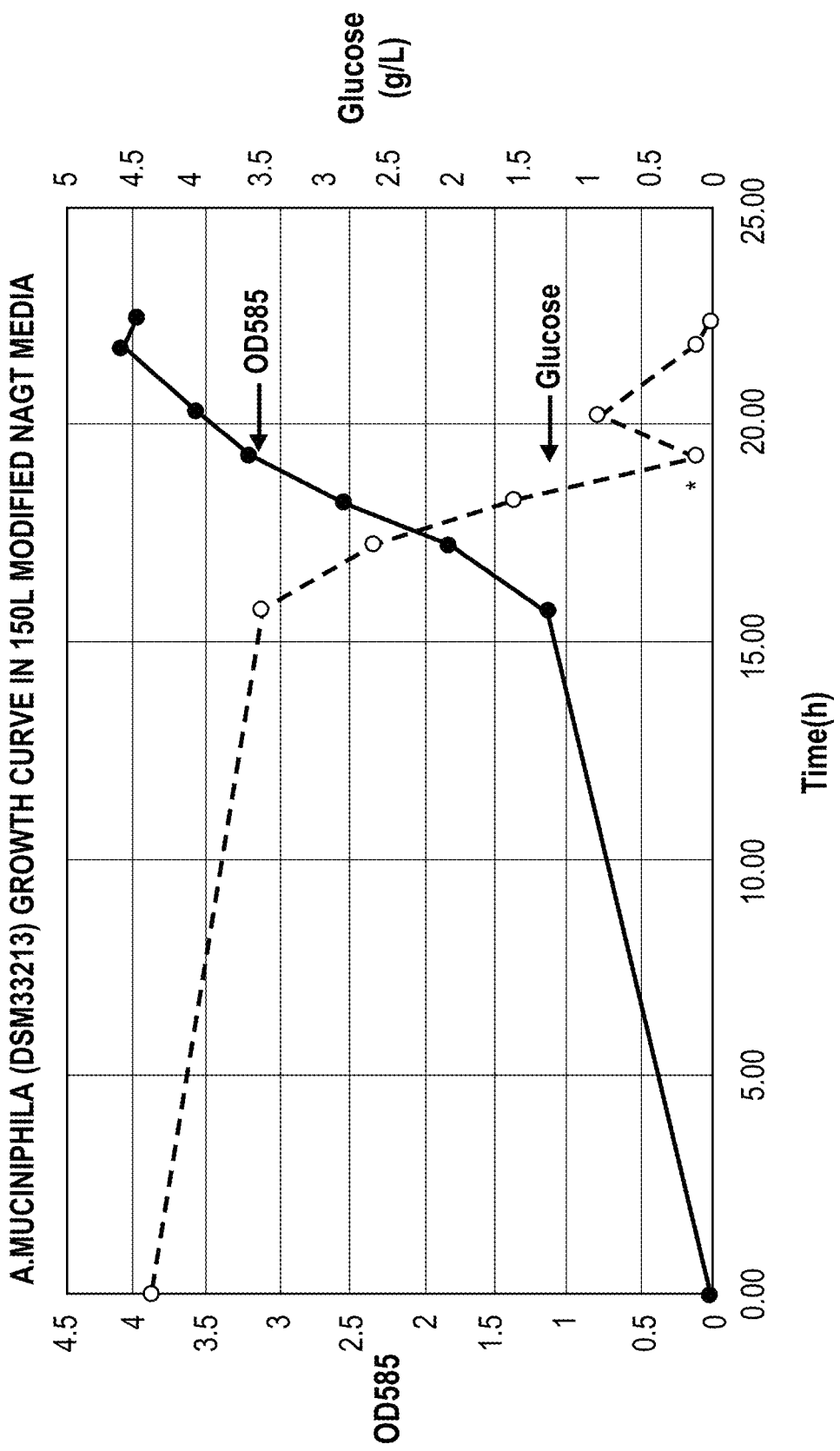
FIG. 13 shows a chart of light absorption at 585 nanometer wavelength (Y-axis on the left) and glucose concentration (g/L) (Y-axis on the right) versus time for the growth of *A. muciniphila* (DSM 33213) 150 liter culture in NAGT media. The chart shows the relationship between the growth of *A. muciniphila* and glucose level over time. The addition (*) of glucose (4.52 g/L) and N-acetylglucosamine (5.54 g/L) at 19$^{th}$ hour allowed the *A. muciniphila* culture to maintain in the exponential growth after 20$^{th}$ hour.

150 L media was degassed by sparging using $N_2H_2CO_2$ (90:5:5). Degassing was performed at 6.5 L/min until the redox value dropped and stabilized. Primary culture was inoculated at 0.4% (e.g., —600 mL of inoculum culture), and culture glucose consumption and optical density were monitored every 2 hours. The culture was stirred at 100 rpm and grew at 37° C. As shown in FIG. 13, a filter sterilized feed of 678 g of glucose and 831 g of N-acetylglucosamine was added at $19^{th}$ hour to allow the bacterial culture to maintain in the exponential growth after $20^{th}$ hour. The culture was stopped if a) a phase of growth deceleration was observed or b) the culture had grown for 24 hours.

Large-Scale Growth of *Lactobacillus crispatus* (DSM 33187)

To prepare the Vegitone MRS medium for 1 L inoculum culture and 150 L primary culture, medium components are weighted as followings: pea peptone (20 g/L), yeast extract (10 g/L), dextrose (20 g/L), dibasic potassium phosphate ($K_2HPO_4$) (2.5 g/L), ammonium citrate (0.3 g/L), magnesium sulfate heptahydrate ($MgSO_4 \times 7H_2O$) (0.1 g/L), sodium acetate (NaOAc) (5.54 g/L), Tween 80 (4 g/L). The mixture was stirred until all components are fully dissolved, clear and free of solids and precipitates.

The pH of the Vegitone MRS medium was adjusted to 6.5±0.1 with $NH_4OH$ or acetic acid. The medium was then sterilized by autoclaving at 121° C. for 20 minutes. Glucose was filter sterilized separately. The media components were then mixed together.

Inoculum flask containing Vegitone MRS was moved to the anaerobic chamber and degassed with $N_2H_2CO_2$ by incubation under anaerobic atmosphere for 48 hours. Inoculum culture was inoculated from the RCB or MCB (0.4% for *L. crispatus* (DSM 33187) and incubated under anaerobic atmosphere at 37° C. with no agitation. Culture glucose consumption and optical density were monitored every 2 hours. The culture was stopped if a) a phase of deceleration is observed or b) the culture has been growing for 24 hours.

Figure 14:
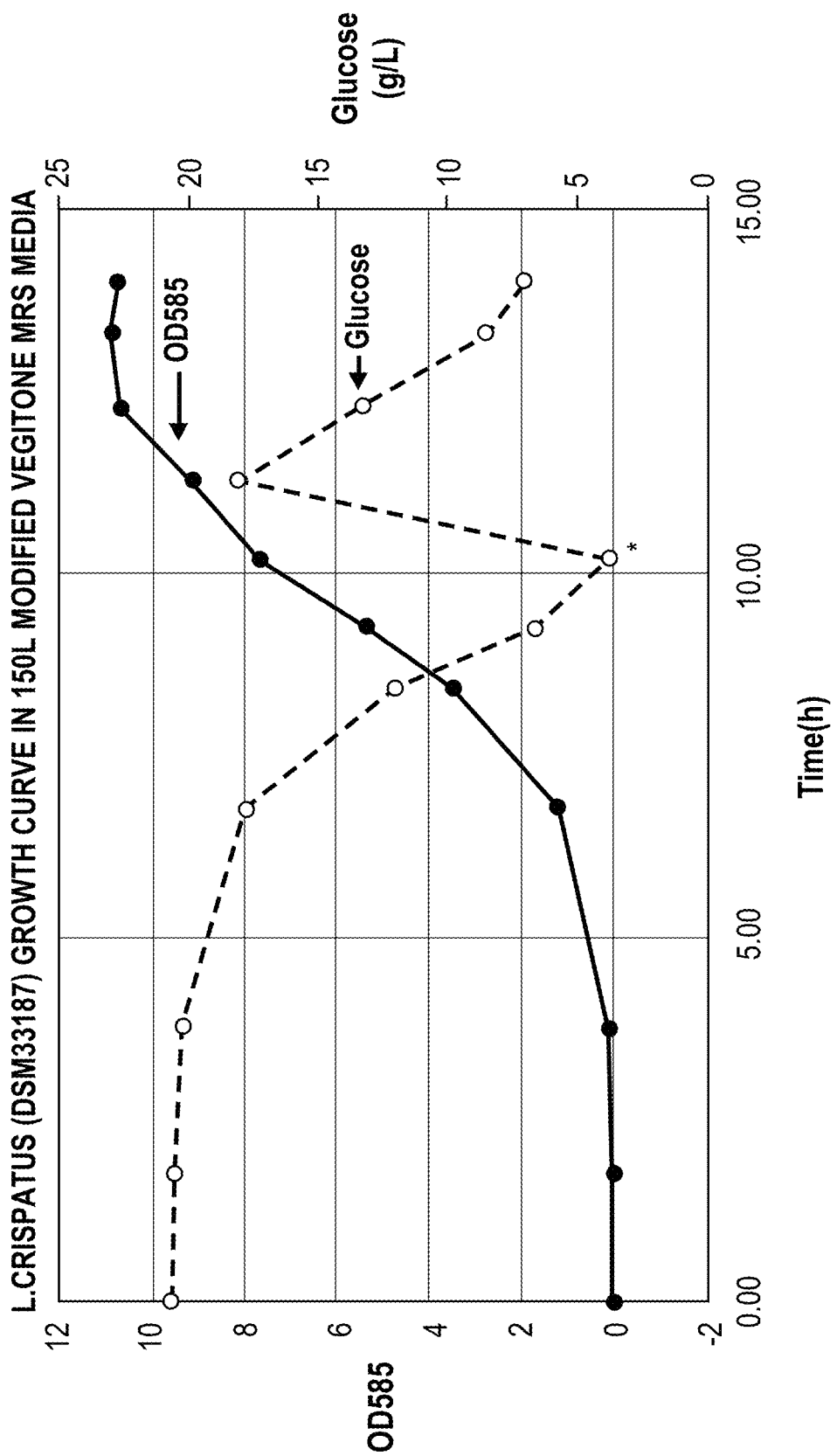
FIG. 14 shows a chart of light absorption at 585 nanometer wavelength (Y-axis on the left) and glucose concentration (g/L) (Y-axis on the right) versus time for the growth of *L. crispatus* (DSM 33187) 150 liter culture in Vegitone MRS media. The chart shows the relationship between the growth of *L. crispatus* (DSM 33187) and glucose level over time. The addition (*) of glucose (35 g/L) at 10$^{th}$ hour allowed the *L. crispatus* culture to maintain in the exponential growth from 10$^{th}$ to 12$^{th}$ hour and enter stationary growth after 12$^{th}$ hour.

150 L media was degassed by sparging using $N_2H_2CO_2$ (90:5:5). Degassing was performed at 6.5 L/min until the redox value dropped and stabilized. Primary culture was inoculated at 0.4% (e.g., —600 mL of inoculum culture), and culture glucose consumption and optical density were monitored every 2 hours. The culture was stirred at 100 rpm and grew at 37° C. As shown in FIG. 14, a feed of 5250 g of glucose was added at $10^{th}$ hour and allowed the bacterial culture to maintain in the exponential growth from $10^{th}$ to $12^{th}$ hour and enter stationary growth after $12^{th}$ hour. The culture was stopped if a) a phase of growth deceleration was observed or b) the culture had grown for 24 hours.

Large-Scale Growth of *Faecalibacterium Prausnitzii* (DSM 33185)

To prepare the YFAP medium for 1 L inoculum culture and 150 L primary culture, media components are weighted as followings: pea peptone (20 g/L), yeast extract (5 g/L), dextrose (10 g/L), dibasic potassium phosphate ($K_2HPO_4$) (2.5 g/L), sodium chloride (NaCl) (1 g/L), magnesium sulfate heptahydrate ($MgSO_4 \times 7H_2O$) (0.2 g/L), sodium bicarbonate ($NaHCO_3$) (1 g/L), sodium acetate NaOAc (5 g/L), L-cysteine (1 g/L). YFAP Vitamin Mix Solution was prepared as described in Example 3. The mixture was stirred until all components are fully dissolved, clear and free of solids and precipitates.

The pH of the YFAP medium was adjusted to 6.5±0.1 with NaOH and acetic acid. The medium was then sterilized by autoclaving at 121° C. for 20 minutes. Glucose and YFAP Vitamin Mix Solution were filter sterilized (0.2 μm filter). The media components were then mixed together.

Inoculum flask containing YFAP was moved to the anaerobic chamber and degassed with $N_2H_2CO_2$ by incubation under anaerobic atmosphere for at least 16 hours. Inoculum culture was inoculated from the RCB or MCB (0.4% for *F. prausnitzii* (DSM 33185) and incubated under anaerobic atmosphere at 37° C. with no agitation. Culture glucose consumption and optical density were monitored every 2 hours. The culture was stopped if a) a phase of deceleration is observed or b) the culture had been growing for 24 hours.

Figure 15:
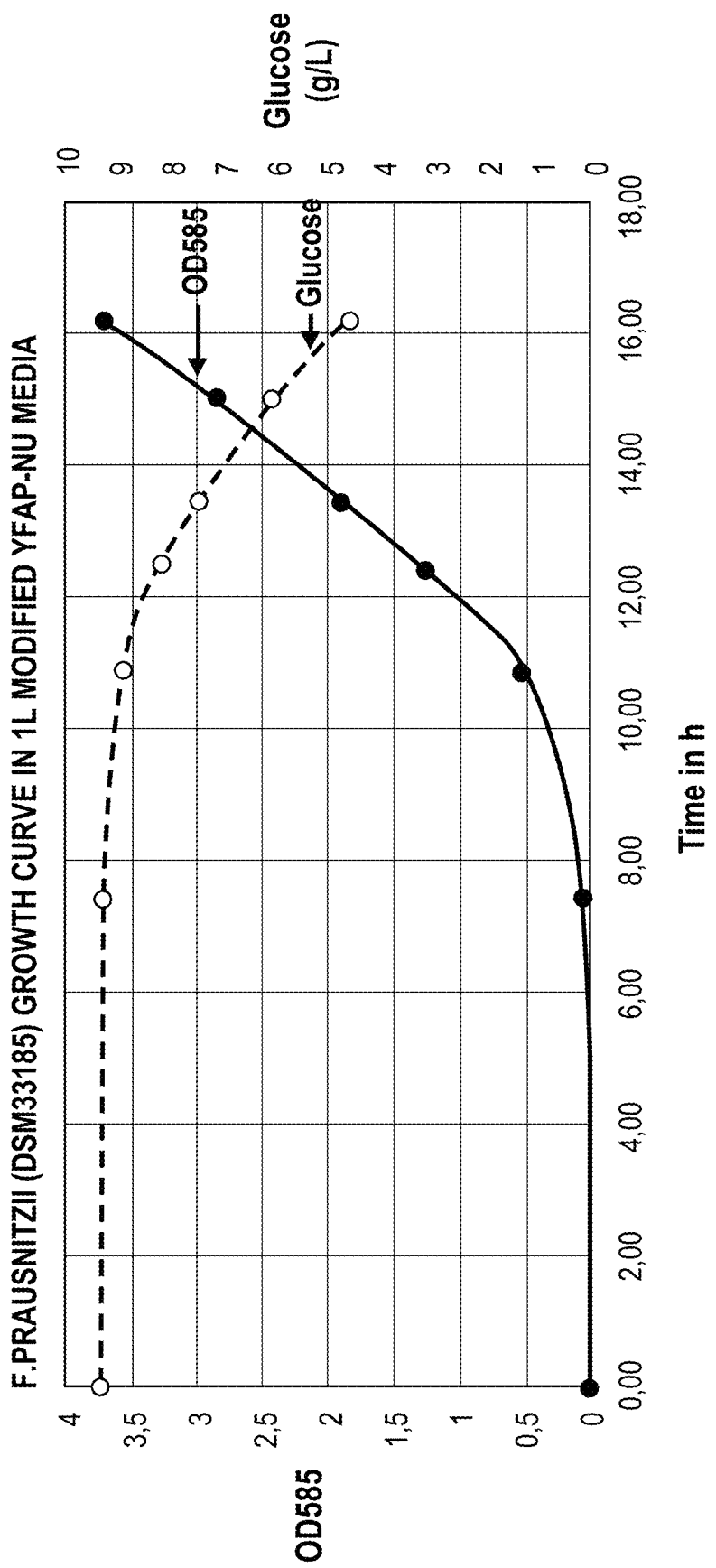
FIG. 15 shows a chart of light absorption at 600 nanometer wavelength versus time for the measurement of growth over time of the 1 L *F. prausnitzii* (DSM 33185) culture in YFAP-NU media.
Figure 16:
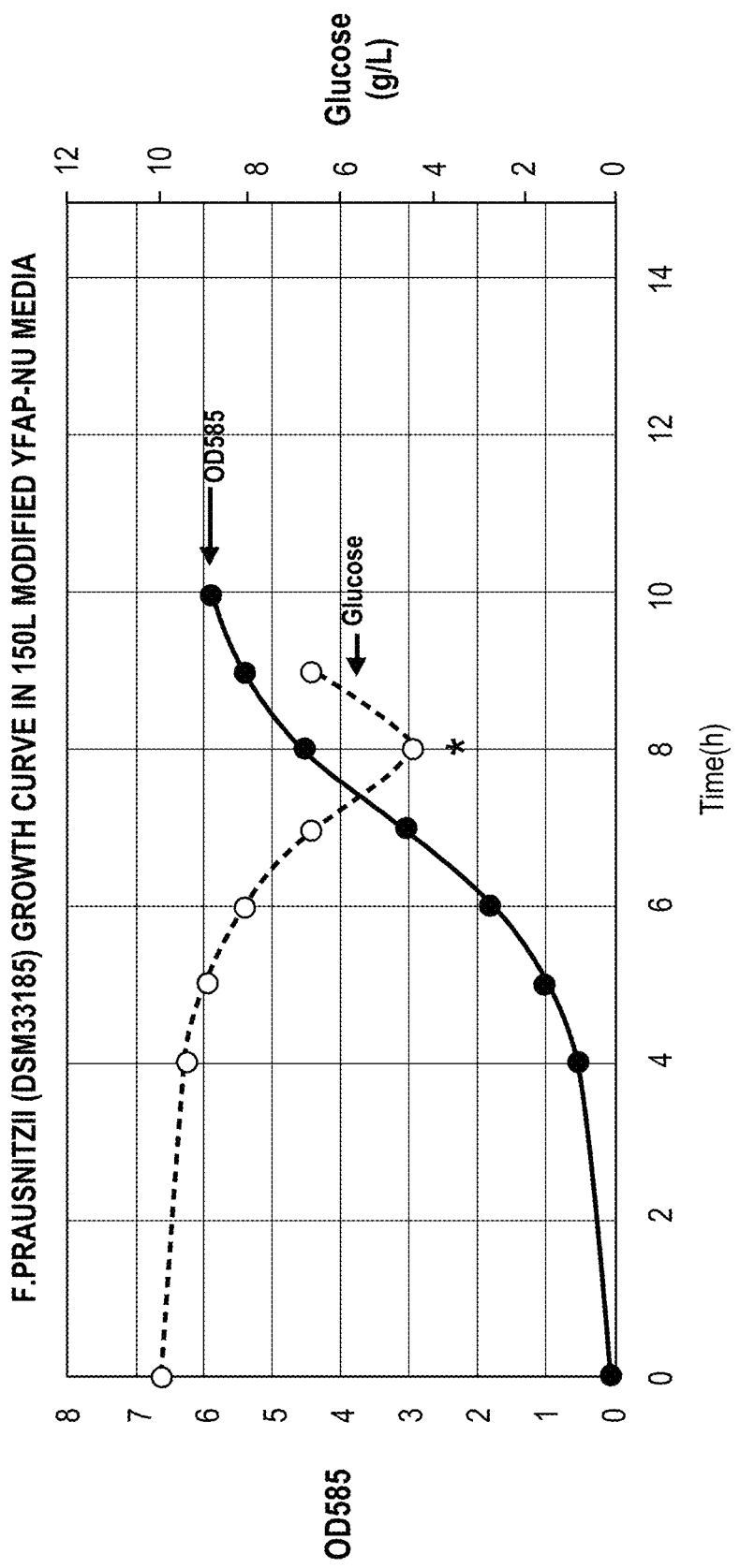
FIG. 16 shows a chart of light absorption at 600 nanometer wavelength versus time for the measurement of growth over time of the 150 L *F. prausnitzii* (DSM 33185) culture in YFAP-NU media. The addition (*) of glucose (10 g/L) at 8$^{th}$ hour allowed the *F. prausnitzii* culture to enter exponential phase and reach stationary phase.

150 L media was degassed by sparging using $N_2H_2CO_2$ (90:5:5). Degassing was performed at 6.5 L/min until the redox value dropped and stabilized. As shown in FIG. 15, primary culture was inoculated at 0.4% (e.g., —600 mL of inoculum culture) and maintained exponential growth from $11^{th}$ to $16^{th}$ hour, and culture glucose consumption and optical density were monitored every 2 hours. The culture was stirred at 100 rpm and grew at 37° C. As shown in FIG. 16, a feed of 150 g of glucose was added at $8^{th}$ hour allowed the bacterial culture to maintain exponential growth after $8^{th}$ hour. The culture was stopped if a) a phase of growth deceleration was observed or b) the culture had grown for 24 hours.

Example 6: Lyophilization of Bacteria

To prepare for the cryoprotectant solution for the bacteria grown in a large-scale growth condition, saccharose (80 g/L), trehalose (13.3 g/L), sodium glutamate (5.3 g/L), L-cysteine (1.3 g/L) were mixed with water, filter sterilized (0.2 μm filter), and degassed by sparging with a $N_2H_2CO_2$ (90:5:5) gas. The redox state was monitored with a standard calibrated redox probe. Degassing continued until the redox value dropped and stabilized, indicating full anaerobic state (about 60 min). The fully reduced cryoprotectant mix was sealed to protect from air intrusion until use. All Sharples Centrifuge and mixing tank components were sterilized in place by autoclaving at 121° C. for 20 min.

The bacteria were grown for 31 hours and harvested from the 20 L or 150 L culture using a cooled Sharples Centrifuge set at 10° C. The bacteria in the cylinder was immediately transferred to a sterile blender bag and the weight of the biomass is measured. An identical weight of the cryoprotectant solution, anaerobic and pre-reduced, was then added to the blender bag. The anaerobic gas line was inserted into the corner of the blender bag. The $N_2H_2CO_2$ (90:5:5) gas was used to sparge the bacteria and cryoprotectant mix for 5 mins at 6.5 L/min flow rate.

After sparging with anaerobic gas to ensure the concentrated bacteria and cryoprotectant mix was maintained in an anaerobic condition, the blender bag was sealed placed in a secondary blender bag. The double-walled blender bag was placed inside the JumboMix 3500 paddle mixer and blended for 5 mins on Speed #3 to generate a homogenous anaerobic mix.

After homogenization, the cryoprotectant solution with bacteria was pumped into singe use freeze-drying plates. Each plate is weighed. Plates were immediately transferred to a pre-cooled (−40° C.) lyophilizer for lyophilization using the steps listed in TABLE 8:

TABLE 8

Lyophilization Program Setting.

| Procedure | Step | Shelf temperature (° C.) | Ramp time (hour) | Hold time (hour) | Vacuum (μBar) |
|---|---|---|---|---|---|
| Freezing | 1 | −45 | 0 | 5 | None |
| Vacuum pull-down | 2 | −45 | 0 | 1 | 400 |
| Primary drying | 3 | −20 | 5 | Wait until the product temperature is > 25° C. | 400 |
| Secondary Drying | 4 | 20 | 4 | 24 | 27 |
| Hold | 5 | 22 | 0.2 | Hold | 27 |

The lyophilization procedure finished when the product temperature was stable for at least two hours. The lyophilized product was ground using a 1 mm grind setting and stored in vacuum sealed bags at −20° C. until use.

Example 7: Comparison of Agar Plating Vs Flow Cytometry for Determining the Number of Metabolically Active Cells in a Sample Two different techniques, conventional agar plating and flow cytometry, were compared for their ability to provide consistent and accurate readouts on the number of metabolically active cells of a strain (e.g., strain potency) in a sample, such as a cell suspension or a biological sample (e.g., a human fecal sample). Evaluated strains include *Akkermansia muciniphila* (DSM 33213), *Faecalibacterium prausnitzii* (DSM 33185), and/or *Lactobacillus crispatus* (DSM 33187) that can be used in a bacterial consortium herein.

In order to determine the number of metabolically active bacterial cells (defined as CFUs) of, e.g., *Akkermansia muciniphila* (DSM 33213), *Faecalibacterium prausnitzii* (DSM 33185), and/or *Lactobacillus crispatus* (DSM 33187) in a sample, the procedure of agar plating was compared to the use of flow cytometry.

Figure 17A:
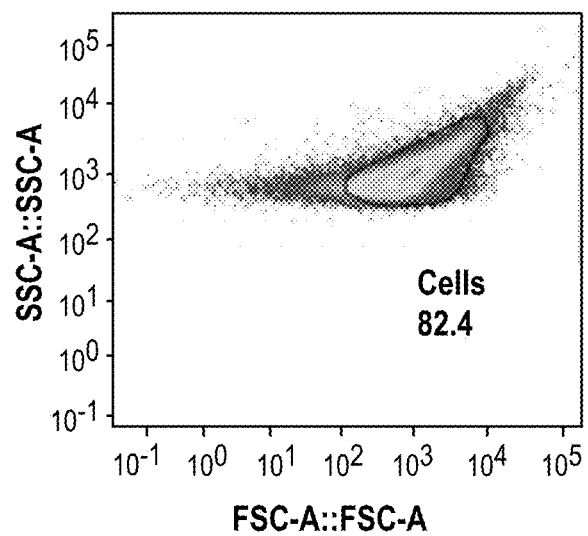
FIGS. 17A-17C show a flow cytometry gating experiment of heat-killed control *A. muciniphila* (DSM 33213) cells for quantification of metabolically active therapeutic strains in a bacterial cell population, e.g., a cell population that can be administered to a human subject. Used as an example strain, *A. muciniphila* (DSM 33213) cell stock solutions were diluted to 10^-4 M in 0.9% NaCl buffer solution and placed in a heating block at 95° C. for 20 minutes to ensure cell death prior to performing the experiment. Cells were stained with 2 µM of propidium iodide and 2 µM of SYTO9. A gate is applied to all cells (FIG. 17A) counted by Forward Scatter Area (FSC-A) and Side Scatter Area (SSC-A) to select for cell size and granularity, respectively. Those cells were then gated on linearity based on Forward Scatter Height (FSC-H) and Forward Scatter-Area (FSC-A) to identify single cells (FIG. 17B). The single cells were then used to set gates for dead cells (PIhighSYTO9 low) as well as live cells (PI-SYTO9 high), which gave the percentages of live and dead cells in 50 µl of solution (FIG. 17C).
Figure 17B:
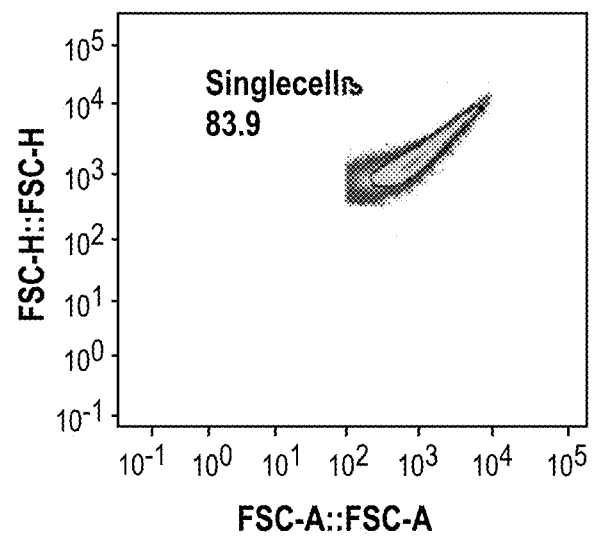
Figure 17C:
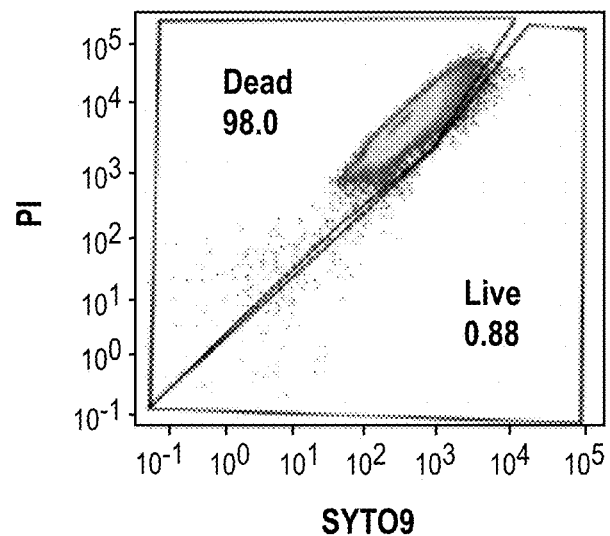

FIGS. 17A-17C show a flow cytometry gating experiment of heat-killed control *A. muciniphila* (DSM 33213) (*A. muciniphila* (DSM 33213)) cells for quantification of metabolically active therapeutic strains in a bacterial cell population, e.g., a cell population that can be administered to a human subject. Used as an example strain, *A. muciniphila* (DSM 33213) cell stock solutions were diluted to $10^{-4}$ M in 0.9% NaCl buffer solution and placed in a heating block at 95° C. for 20 minutes to ensure cell death prior to performing the experiment. Cells were stained with 2 μM of propidium iodide and 2 μM of SYTO9. A gate is applied to all cells (FIG. 17A) counted by Forward Scatter Area (FSC-A) and Side Scatter Area (SSC-A) to select for cell size and granularity, respectively. Those cells are then gated on linearity based on Forward Scatter Height (FSC-H) and Forward Scatter-Area (FSC-A) to identify single cells (FIG. 17B). The single cells were then used to set gates for dead cells (PIhighSYTO9 low) as well as live cells (PI-SYTO9 high), which gives the percentages of live and dead cells in 50 μl of solution (FIG. 17C). FIG. 17A shows flow cytometry results obtained when a gate was applied to all cells counted by Forward Scatter Area (FSC-A) and Side Scatter Area (SSC-A) to select for cell size and granularity, respectively. FIG. 17B shows flow cytometry results obtained when cells were then gated on linearity based on Forward Scatter Height (FSC-H) and Forward Scatter-Area (FSC-A) to identify single cells. FIG. 17C shows flow cytometry results obtained when single cells were used to set gates for dead cells (PIhighSYTO9 low) as well as live cells (PI-SYTO9 high), which gave the percentages of live and dead cells in 50 μL of cell suspension. This data show that the flow cytometry method allows to accurately determine the number of metabolically active/inactive cells as demonstrates in FIG. 17C showing metabolically inactive cells (cells had been inactivated with heat).

TABLE 9 below shows the sequence of calculations used to calculate the total live cells in each dilution. To calculate the "Total Cells Counted", diluted and unstained cells were counted by the machine and multiplied by the dilution factor (Dilution Factor×Cells=Total Cells Counted). The "Standard Deviation" and "Average Total Cells" were derived from the "Total Cells Counted". The "Percent Live Cells" were calculated by applying the control gates explained in FIGS. 17A-17C to stained cells in dilution. Applying the "Percent Live Cells" to the "Average Total Cells", the "Total Live Cells" in *A. muciniphila* (DSM 33213) MCB glycerol stock was calculated.

a sample (e.g., quantified as CFU/mL) compared to the plating method. The left y-axis shows the number of Total Live Cells measured by flow cytometry. The right y-axis shows the calculated Average CFU/mL values from nutrient agar plating for biological duplicates. A two tailed Mann Whitney t-test showed no significant difference between the mean values of the two quantification methods with a p-value of 0.0532. The results show variability of the agar plating technique and the relative consistency of FACS technique, validating the use of the flow cytometer as a method of quantifying bacterial strains in a biological sample. Samples that may be tested using this technique include human fecal samples and bacterial strain samples that may be analyzed for quality control purposes.

Together, these results demonstrate that the flow cytometry methods described herein can be used determine (i) the ratio of metabolically active to metabolically inactive cells in a sample, and (ii) absolute number of metabolically active bacterial cells in a sample.

TABLE 9

Calculation of the Number of Live Cells using Flow Cytometry.

| Dilution Factor | Total Cells Counted | Standard Deviation | Average Total Cells | Percent Live Cells | Total Live Cells | Standard Deviation |
|---|---|---|---|---|---|---|
| 0.001 | $2.21 \times 10^{10}$ | $3.67 \times 10^{9}$ | $1.47 \times 10^{10}$ | 85.2 | $1.25 \times 10^{10}$ | $1.17 \times 10^{8}$ |
| 2 | $1.29 \times 10^{10}$ | $3.67 \times 10^{9}$ | $1.47 \times 10^{10}$ | 84.4 | $1.24 \times 10^{10}$ | $1.17 \times 10^{8}$ |
| 4 | $1.40 \times 10^{10}$ | $3.67 \times 10^{9}$ | $1.47 \times 10^{10}$ | 83.8 | $1.23 \times 10^{10}$ | $1.17 \times 10^{8}$ |
| 8 | $1.42 \times 10^{10}$ | $3.67 \times 10^{9}$ | $1.47 \times 10^{10}$ | 84.1 | $1.24 \times 10^{10}$ | $1.17 \times 10^{8}$ |
| 16 | $1.26 \times 10^{10}$ | $3.67 \times 10^{9}$ | $1.47 \times 10^{10}$ | 82.8 | $1.22 \times 10^{10}$ | $1.17 \times 10^{8}$ |
| 32 | $1.26 \times 10^{10}$ | $3.67 \times 10^{9}$ | $1.47 \times 10^{10}$ | 84.9 | $1.25 \times 10^{10}$ | $1.17 \times 10^{8}$ |

Similar results were obtained for the strains *Faecalibacterium prausnitzii* (DSM 33185), and *Lactobacillus crispatus* (DSM 33187) demonstrating that flow cytometry can be used to accurately determine the number of metabolically active therapeutic strains in a sample. Comparing the number of total live cells determined using the plating method to those determined by flow cytometry indicates that flow cytometry may allow for a more precise measurement of total live cells in a sample (see, for example, FIGS. 17A-17C).

Figure 18:
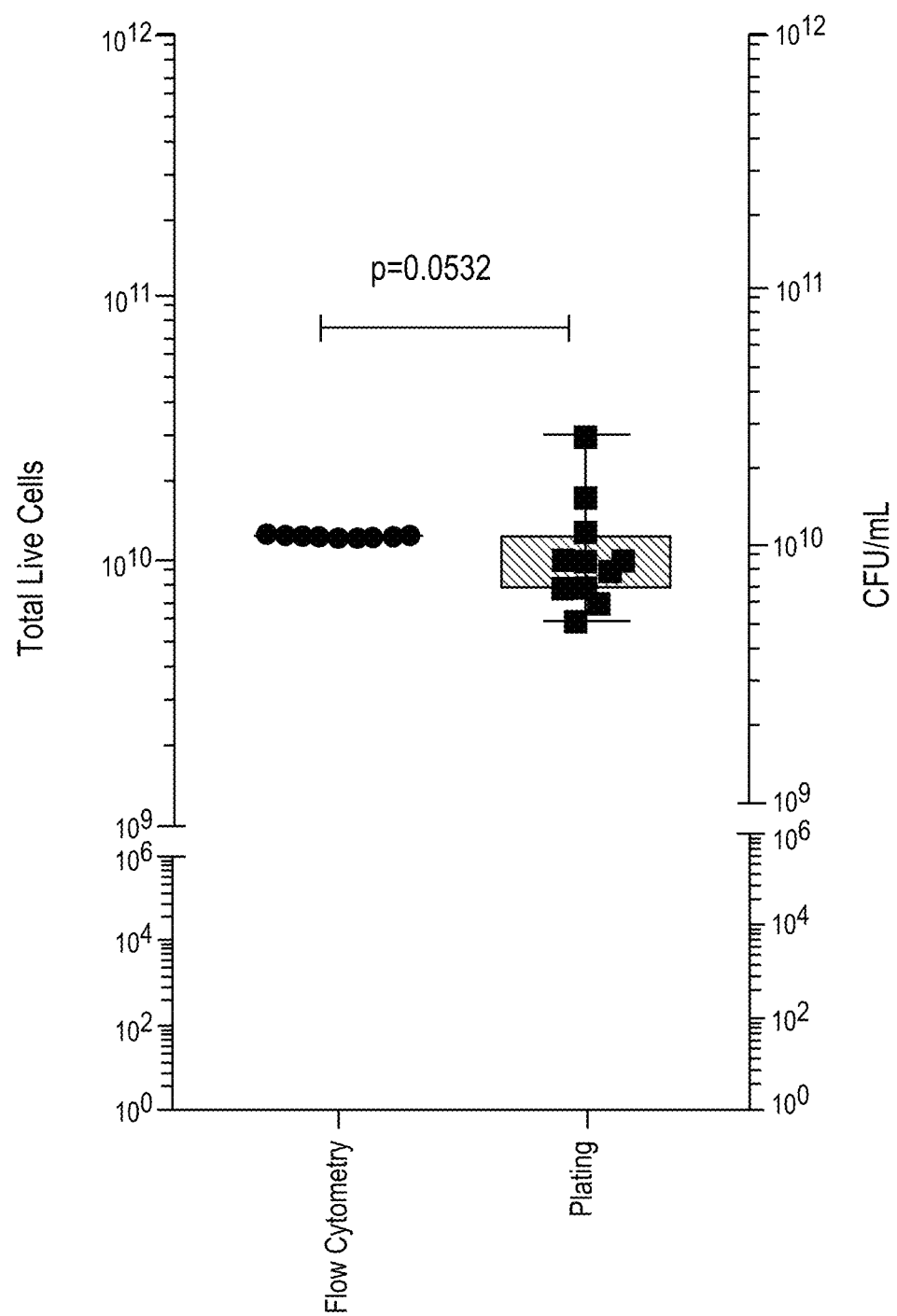
FIG. 18 shows a graph comparing flow cytometry quantification data of live cells with the number of total live cells determined using the (standard) agar plating method. The left y-axis shows the number of Total Live Cells measured by flow cytometry. The right y-axis shows the calculated Average CFU/mL values from nutrient agar plating for biological duplicates. A two tailed Mann Whitney t-test showed no significant difference between the mean values of the two quantification methods with a p-value of 0.0532.

In addition, FIG. 18 shows a graph comparing flow cytometry quantification data of live cells with the number of total live cells determined using the (standard) plating method. The data indicate that flow cytometry allowed a significantly more precise measurement of total live cells in Example 8: Quantification of Bacterial Cells in Fecal DNA Using qPCR The use of quantitative polymerase chain reaction (qPCR) is described for quantification of the bacterial strains *Akkermansia muciniphila* (DSM 33213), *Faecalibacterium prausnitzii* (DSM 33185), and *Lactobacillus crispatus* (DSM 33187) in a sample. This example describes strain quantification using specific primers, qPCR and fecal DNA as a template.

1. Materials

TABLE 10 below shows exemplary strain-specific primer sequences used for strain quantification:

TABLE 10

Strain-specific Primer Sequences.

| Primer Sequence (5' to 3') | SEQ ID NO | Strain | Tm | GC Content (%) |
|---|---|---|---|---|
| TATCCGGACTCCTCCATCTG | 1 | A. muciniphila (DSM 33213) | 55 | 62.4 |
| TGTTCGTGCGTTCTTACCTG | 2 | A. muciniphila (DSM 33213) | 50 | 60.4 |
| ATTCCTGAGAAGGCCAGGAT | 3 | A. muciniphila (DSM 33213) | 60.4 | 50 |
| CTGCCGACAAGCATTCCTAT | 4 | A. muciniphila (DSM 33213) | 60.4 | 50 |
| ACCAAGGTTAGCCGCTTTTT | 5 | A. muciniphila (DSM 33213) | 45 | 58.4 |
| CTTGCCCAACAAAATGACCT | 6 | A. muciniphila (DSM 33213) | 45 | 58.4 |

TABLE 10-continued

Strain-specific Primer Sequences.

| Primer Sequence (5' to 3') | SEQ ID NO | Strain | Tm | GC Content (%) |
|---|---|---|---|---|
| GTAAGCTCTGTTTCGGCAGCAC | 7 | *F. prausnitzii* (DSM 33185) | 62.3 | 54.5 |
| ACATTGCACGCTTTGCCGAC | 8 | *F. prausnitzii* (DSM 33185) | 62.7 | 55 |
| AATTCAGGTTCGGCTGCTGT | 9 | *F. prausnitzii* (DSM 33185) | 60.4 | 50 |
| CAGGCAGACGTTCTGCTACT | 10 | *F. prausnitzii* (DSM 33185) | 62.4 | 55 |
| ACGCGTCTCTTTTTGAGCAC | 11 | *L. crispatus* (DSM 33187) | 60.4 | 50 |
| CCAAATTCAAAGGACTTGGGCT | 12 | *L. crispatus* (DSM 33187) | 60.8 | 45.45 |
| CGTAGTCCACTTAAGAAGGCCG | 13 | *L. crispatus* (DSM 33187) | 60.73 | 54.55 |
| GGGCTTTCTTCAAACCTGGC | 14 | *L. crispatus* (DSM 33187) | 59.68 | 55 |

PacBio sequencing was performed on genomic DNA extracted from *L. crispatus* (DSM 33187), *F. prausnitzii* (DSM 33185), *A. muciniphila* (DSM 33213). Using these data, a comparative genomic analysis of all bacterial strains was performed to identify unique regions within the genomes of *L. crispatus* (DSM 33187), *F. prausnitzii* (DSM 33185), *A. muciniphila* (DSM 33213). After identification of unique regions, qPCR primer pairs (see TABLE 10 above) were designed to target the unique regions present within these strains.

Additional materials used for this experiment included: (i) *A. muciniphila* (DSM 33213), *F. prausnitzii* (DSM 33185), *L. crispatus* (DSM 33187) DNA; (ii) Human Fecal DNA Sample Control (did not contain strains); (iii) extracted DNA from Clinical Samples; (iv) metal 384 qPCR plate holder; (v) DNA/RNAse free, sterile Eppendorf tubes; and (vi) QuantStudio 6 qPCR Thermocycler.

2. Procedure

Clinical sample names and DNA concentrations were calculated electronically, and all samples were normalized to 10 ng/μL with a final volume of 100 μL. Each run utilized a positive control standard curve of 7 points generated with pure bacterial DNA diluted in a human fecal DNA background. These standards (abbreviated as "std") were pre-made and aliquoted for ease of use. For the standard curve, the following serial dilutions of target strain DNA were included in the run (TABLE 11):

TABLE 11

Standard Strain DNA Preparations.

| Standard | Final Amount of Strain-specific DNA per Reaction well | Final DNA Amount per Well (including Control Fecal DNA) |
|---|---|---|
| Std 1 | 10 ng | 50 ng |
| Std 2 | 1 ng | 50 ng |
| Std 3 | 0.1 ng | 50 ng |
| Std 4 | 0.01 ng | 50 ng |
| Std 5 | 0.001 ng | 50 ng |
| Std 6 | 0.0001 ng | 50 ng |
| Std 7 | 0.00001 ng | 50 ng |

The following items were used for strain DNA quantification experiments:

TABLE 12

Materials for DNA Quantification Experiments.

| Item | Quantity |
|---|---|
| Fecal DNA from Clinical Samples (store on ice) | 161 samples (max) |
| *A. muciniphila* (DSM 33213), *F. prausnitzii* (DSM 33185) or *L. crispatus* (DSM 33187) Standard DNA | ST Strain DNA (Plate Specific) |
| 384 well plate (sterile) | 1 |
| 96 well plate (sterile) | 2 |
| Eppendorf Tubes (sterile) | 3 |
| 15 mL Falcon Tube (sterile) | 1 |
| Pipette | 1000 μL, 200 μL, 10 μL, multichannel pipette |
| Pipette tips (sterile) | 1 box of 1000 μL, 200 μL, 10 μL, |
| USP WFI (sterile) | 50 mL |
| Tube Rack | 1 |
| 384 Metal Cooling Plate | 1 |
| Styrofoam cooler full of ice | 1 |
| Sealing Film | 2 |
| Primers (forward and reverse) | 1 stock of each strain |
| SYBR Select Master Mix (store on ice) | One (1) 5 mL bottle |

The calculated amount of water and DNA solution was added to the appropriate wells. The qPCR plate was sealed, vortexed (5-10 seconds) and centrifuged for 2 minutes at 1000 rpm.

3. Preparation of Primer Stocks and Master Mix

The forward and reverse strain specific primers were completely thawed, and primer stocks were maintained at 100 μM in 1×TE buffer (see, for example, TABLE 10). In two Eppendorf tubes (one for the forward primer and one for the reverse primer) 360 μL of sterile USP grade WFI was added. Then, 40 μL of forward primer solution was added and homogenized, and the same step was repeated for the reverse primer solution. The resulting 10 μM primers solutions were combined with SYBR Select Master Mix (2× Stock) and sterile water and homogenized.

Using the qPCR 384 Well Plate, 20 μL of qPCR Master Mix were aliquoted into wells A-N 1-24 and O 1-14. After master mix had been aliquoted into all 350 wells, using the DNA normalization plate, 5 μL of DNA of all wells in row A were taken up and inoculated the odd wells in row A in the reaction plate. Then, 5 μL of DNA from all wells in row A was transferred and inoculated the even wells in row A in the reaction plate. The last 2 steps were repeated for all wells until the DNA was added to the reaction plate. Subsequently, the standard curve stock DNA plate of the appropriate strain was transferred to the Biosafety Cabinet, followed by pipetting the standards into the correct wells of rows P per the reaction plate setup. Following mixing and centrifugation, the samples were placed in the Quantstudio qPCR machine.

The following cycling conditions were used as shown below in TABLE 13:

TABLE 13

Cycling Conditions.

| Step | Temp. ° C. | Time | |
|---|---|---|---|
| Activation | 50 | 2 min | |
| Initial Denaturation | 95 | 2 min | |
| Denaturation | 95 | 15 seconds | 40 Cycles |
| Anneal/Extend | 60 | 1 min | |

TABLE 14 below shows standard curve control cycle threshold (CT) and primer melting temperature (TM) values. TABLE 14 further shows, for each of the selected strains *F. prausnitzii* (DSM 33185), *L. crispatus* (DSM 33187), and *A. muciniphila* (DSM 33213), the estimated number of strain cells in human fecal DNA with standard amounts of strain cell DNA (e.g., 1 ng, 0.1 ng, 0.01 ng, and 0.001 ng) used for generating a standard curve that may be used to quantify the amount of strain cell DNA (using a human fecal DNA background), and the same of amounts of strain cell DNA (e.g., 1 ng, 0.1 ng, 0.01 ng, and 0.001 ng) in water (e.g., without fecal DNA

BACKGROUND

TABLE 14

Standard Curve Control Values and Primer TM Values.

| Sample Name | Estimated No. of Cells | Strain and Primers Name | Average CT | Average TM 1 |
|---|---|---|---|---|
| 50 ng Human Fecal DNA | NA | *F. prausnitzii* Primer 03 | 39.32 | 83.24 |
| 50 ng HF DNA + 1 ng Fp DNA | 290000 | *F. prausnitzii* Primer 03 | 21.51 | 83.44 |
| 50 ng HF DNA + 0.1 ng Fp DNA | 29000 | *F. prausnitzii* Primer 03 | 23.14 | 83.34 |
| 50 ng HF DNA + 0.01 ng Fp DNA | 2900 | *F. prausnitzii* Primer 03 | 26.04 | 83.39 |
| 50 ng HF DNA + 0.001 ng Fp DNA | 290 | *F. prausnitzii* Primer 03 | 29.67 | 83.34 |
| Water | 0 | *F. prausnitzii* Primer 03 | NA | 61.27 |
| 1 ng Fp DNA | 290000 | *F. prausnitzii* Primer 03 | 21.29 | 83.64 |
| 0.1 ng Fp DNA | 29000 | *F. prausnitzii* Primer 03 | 23.79 | 83.59 |
| 0.01 ng Fp DNA | 2900 | *F. prausnitzii* Primer 03 | 26.77 | 83.54 |
| 0.001 ng Fp DNA | 290 | *F. prausnitzii* Primer 03 | 30.63 | 88.32 |
| 50 ng Human Fecal DNA | NA | *L. crispatus* Primer 02 | 34.54 | 73.69 |
| 50 ng HF DNA + 1 ng Lc DNA | 279000 | *L. crispatus* Primer 02 | 19.63 | 73.98 |
| 50 ng HF DNA + 0.1 ng Lc DNA | 27900 | *L. crispatus* Primer 02 | 22.98 | 74.03 |
| 50 ng HF DNA + 0.01 ng Lc DNA | 2790 | *L. crispatus* Primer 02 | 26.15 | 73.93 |
| 50 ng HF DNA + 0.001 ng Lc DNA | 279 | *L. crispatus* Primer 02 | 30.43 | 73.98 |
| Water | 0 | *L. crispatus* Primer 02 | 36.00 | 73.93 |
| 1 ng Lc DNA | 279000 | *L. crispatus* Primer 02 | 20.47 | 74.28 |
| 0.1 ng Lc DNA | 27900 | *L. crispatus* Primer 02 | 24.01 | 74.28 |
| 0.01 ng Lc DNA | 2790 | *L. crispatus* Primer 02 | 26.95 | 74.23 |
| 0.001 ng Lc DNA | 279 | *L. crispatus* Primer 02 | 30.16 | 74.08 |
| 50 ng Human Fecal DNA | NA | *A. muciniphila* Primer 03 | 35.29 | 77.54 |
| 50 ng HF DNA + 1 ng Am DNA | 337000 | *A. muciniphila* Primer 03 | 18.63 | 77.59 |
| 50 ng HF DNA + 0.1 ng Am DNA | 33700 | *A. muciniphila* Primer 03 | 22.01 | 77.59 |
| 50 ng HF DNA + 0.01 ng Am DNA | 3370 | *A. muciniphila* Primer 03 | 25.07 | 77.59 |
| 50 ng HF DNA + 0.001 ng Am DNA | 337 | *A. muciniphila* Primer 03 | 27.82 | 77.49 |
| Water | 0 | *A. muciniphila* Primer 03 | 37.85 | 67.33 |
| 1 ng Am DNA | 337000 | *A. muciniphila* Primer 03 | 20.29 | 77.78 |
| 0.1 ng Am DNA | 33700 | *A. muciniphila* Primer 03 | 23.26 | 77.73 |
| 0.01 ng Am DNA | 3370 | *A. muciniphila* Primer 03 | 26.13 | 77.78 |

Figure 19A:
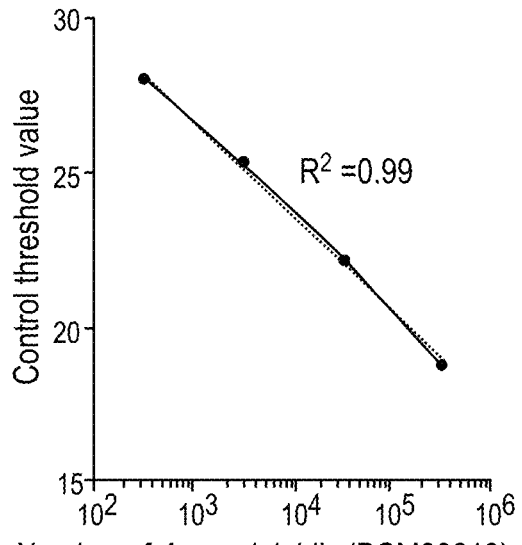
FIGS. 19A-19C show limit of detection curves (the control threshold value was plotted against the number of bacterial cells) for quantifying the bacterial strains *Akkermansia muciniphila* (DSM 33213) (FIG. 19A), and *Faecalibacterium prausnitzii* (DSM 33185) (FIG. 19B), and *Lactobacillus crispatus* (DSM 33187) (FIG. 19C), respectively, in a fecal sample. The dotted lines connect the measured data points, the straight lines represent the fitted regression lines, and "$R^2$" is the coefficient of determination. The data shown represent standard curves generated using pure bacterial DNA (10, 1, 0.1, 0.01, 0.001, 0.0001, and 0.00001 nanogram (ng) of 50 ng of total DNA (strain DNA+fecal DNA) of the three strains diluted in fecal DNA background. In instances where human samples are analyzed to determine the amount of strain (e.g., *A. muciniphila* (DSM 33213), *F. prausnitzii* (DSM 33185), and *L. crispatus* (DSM 33187)) DNA, the control samples can be run and analyzed in parallel to ensure the DNA primers used in the experiments are able to properly amplify the DNA of the bacterial strains.
Figure 19B:
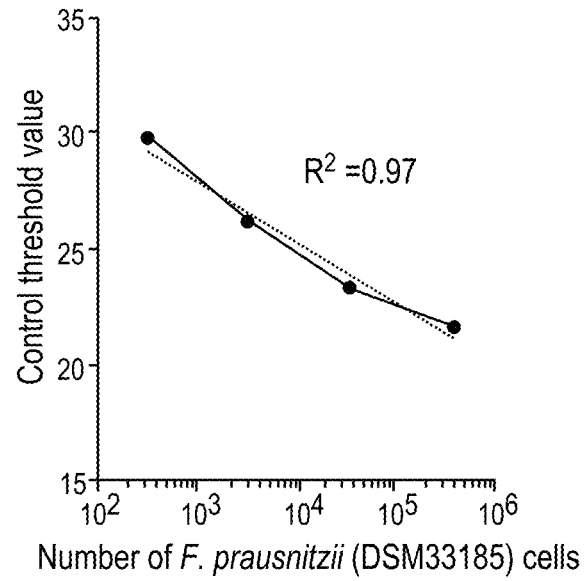
Figure 19C:
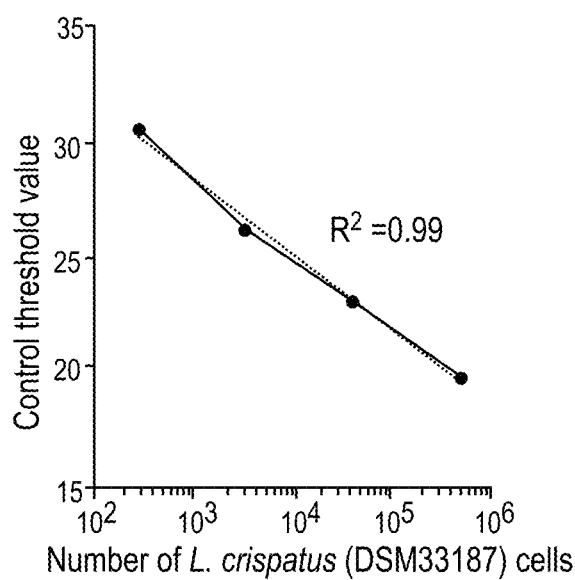

FIGS. 19A-19C shows limit of detection curves for the three selected strains *A. muciniphila* (DSM 33213), *F. prausnitzii* (DSM 33185), and *L. crispatus* (DSM 33187) cells, respectively, that were generated by plotting the measured CT values against the number of estimated strain cells as shown in TABLE 14 above.

Example 9: Mouse-Model System

Provided herein is a protocol for assessing the ability of a bacterial consortium comprising the three bacterial strains *L. crispatus* (DSM 33187), *A. muciniphila* (DSM 33213), and *F. prausnitzii* (DSM 33185) for the treatment of inflammatory diseases, such as allergic diseases, in in vivo mouse models.

In an allergic airway inflammation model using young adult mice sensitized intratracheally to airway allergen, oral administration of Composition A, as defined in Example 2, significantly inhibited elevation of circulating IgE immunoglobulin. In addition, oral administration of Composition A significantly reduced inflammatory Th2 cell expansion in the lung with concurrent reduction in Th2-associated gene expression and lung concentrations of inflammatory cytokines IL-4 and IL-13. Inversely, Composition A resulted in significant expansion of anti-inflammatory Treg cells in the lungs, which is associated with decreased allergic asthma-associated molecular and immunological responses. In addition, significant reductions in circulating IgE levels and airway eosinophilia were observed, while circulating histamine and airway neutrophils trended lower. Based on these studies, and without being bound to any theory, a proposed mechanism of allergic and asthmatic response mitigation was based on the expansion of Treg cells and subsequent inhibition of the Th2-driven generation of allergen specific IgE. It was assumed that expansion of Treg cells was key because Composition A administration was also associated with inhibition of allergic asthma-associated expansion of effector cells, including eosinophils and neutrophils. In contrast to the monoclonal anti-IgE antibody Xolair®

(Omalizumab), which neutralized the IgE effector antibodies responsible for initiating allergic responses, the mechanism of action using Composition A may have occurred upstream in the cascade of allergic sensitization highlighting the preventative potential of Composition A. Composition A was advantageous in that it prevented the generation of new IgE and inflammatory effector cells associated with allergic responses and was expected to have far fewer side effects as a result.

These results demonstrate that the bacterial consortium of Composition A was effective in treating allergic airway inflammation. It was further observed that the therapeutic efficacy of such consortium may be superior to that of the monoclonal anti-IgE antibody Xolair® (Omalizumab) while causing significantly fewer side effects. Together, these results can be used as a basis and rationale for a clinical study in human subjects.

Example 10: Optimized and Ultra-Large-Scale Growth and Manufacturing Process for *Akkermansia muciniphila* (DSM 33213) Drug Substance (3500 L)

Figure 20:
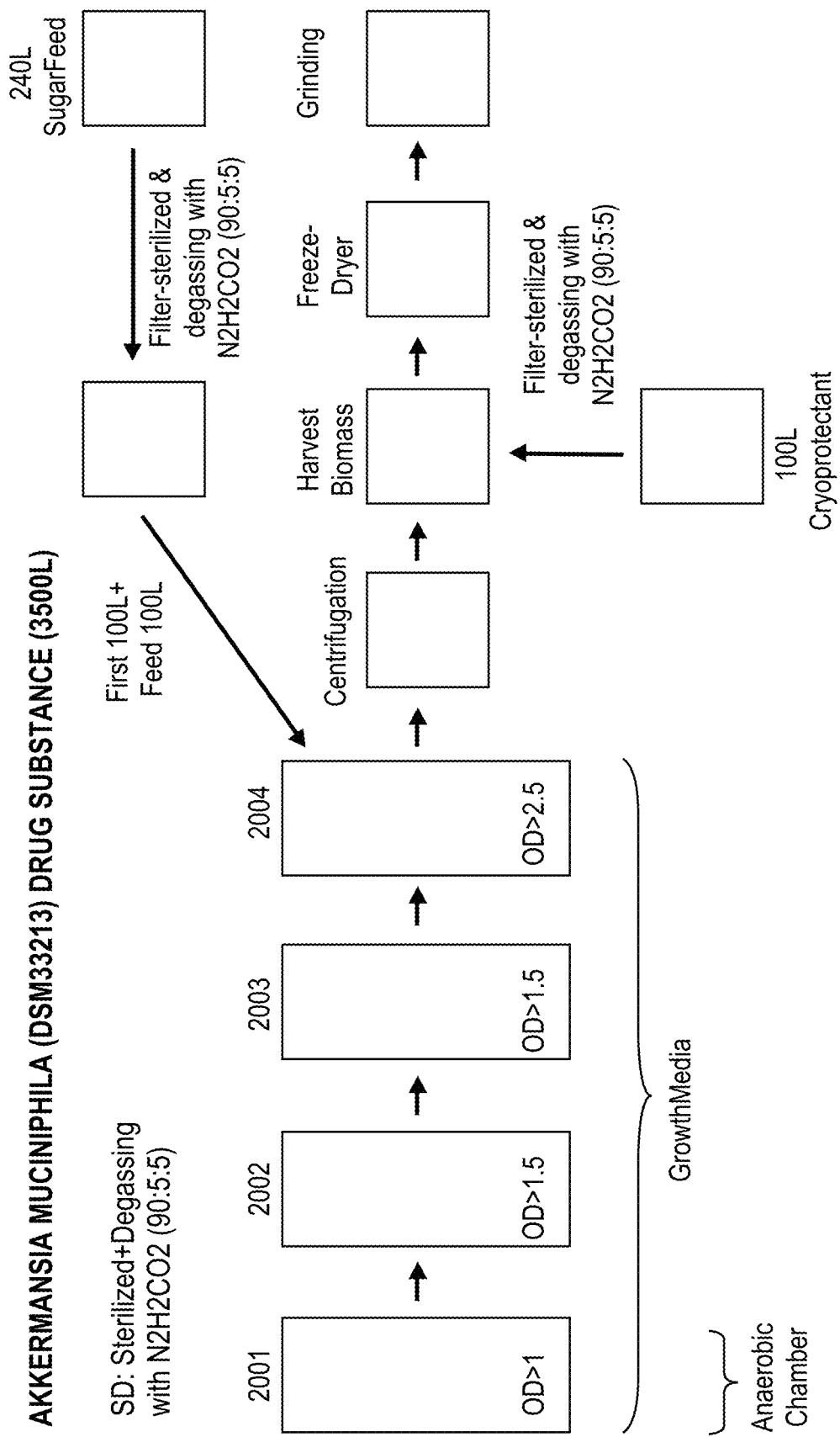
FIG. 20 shows a schematic flow chart for an optimized and ultra-large-scale growth and manufacturing process for *A. muciniphila* (DSM 33213) in 3500 L culture volume. 19.2 mL of Working Cell Bank (WCB) *A. muciniphila* (DSM 33213) was thawed in the anaerobic chamber and inoculated in 1 L of reduced NAGT media (2% v/v inoculation rate) in a 1 L bottle 2001 in an anaerobic chamber. The cultured was stopped when either $OD_{585}>1$ or the culture grew for 48 hours. The entire culture in 2001 was used to inoculate in 16 L media (5% v/v inoculation rate) in a 20 L fermenter 2002. The cultured was stopped when either $OD_{585}>1.5$ or the culture grew for 48 hours. 15 L culture in 2002 was used to inoculate in 300 L media (5% v/v inoculation rate) in a 300 L fermenter 2003. The cultured was stopped when either $OD_{585}>1.5$ or the culture grew for 48 hours. 240 L, defined in TABLE 15, was prepared. 100 L sugar feed was added to a 3500 L fermenter 2004. 300 L culture in 2002 was used to inoculate in 3500 L media (8-10% v/v inoculation rate) in 2004. Another 100 L of the sugar feed was added once glucose concentrations dropped below 2 g/L. The cultured was stopped when either $OD_{585}>2.5$ or the culture grew for 72 hours. The entire culture in 2004 was then centrifuged under anaerobic atmosphere and harvested as a biomass. 100 L filter-sterilized degassed cryoprotectant, defined in TABLE 17, was mixed with the biomass in a mixing tank purged with anaerobic gas. The biomass with cryoprotectant was lyophilized (frozen and dried) and ground. For each step, the media used for the bacterial culture were sterilized (autoclaving at 121° C.) and degassed with $N_2H_2CO_2$ (90:5:5) before use. Sugar components (N-acetylglucosamine and glucose) were prepared separately from the remaining NAGT media components. Sugar feed was filter sterilized, degassed, and added to the remaining NAGT media components to generate the complete culture media.

Manufacturing conditions and procedures for growing *Akkermansia muciniphila* (DSM 33213) in 3500 L volume of culture, as outlined in FIG. 20, were generated to increase yield and growth rate of bacterial strains described herein.

Media Preparation

The components for the 250 L sugar feed (TABLE 15), 3160 L of NAGT media (TABLE 16), 1.25 L glacial acetic acid, and cryoprotectant mix (TABLE 17) were weighted.

TABLE 15

Recipe for the 250 L sugar feed for *A. muciniphila* (DSM 33213).

| Components | Weight (kg) for 250 L feed |
|---|---|
| N-acetyl glucosamine | 48.8 |
| Dextrose | 39.8 |

TABLE 16

Recipe for the 3160 L NAGT Media.

| Components | Weight (kg) for 3160 L NAGT media |
|---|---|
| Pea peptone | 63.3 |
| Yeast extract | 15.8 |
| Sodium chloride | 0.949 |
| Sodium bicarbonate | 3.16 |
| Dibasic potassium phosphate | 7.91 |
| Magnesium sulfate heptahydrate | 0.316 |
| Calcium chloride | 0.316 |
| L-cysteine HCl | 3.16 |
| L-threonine | 12.7 |

TABLE 17

Recipe for 100L Cryoprotectant Mix.

| Components | Weight (kg) for 100 L cryoprotectant mix |
|---|---|
| Saccharose | 8 |
| Trehalose | 1.33 |
| Sodium Glutamate | 0.55 |
| L-Cysteine HCl | 0.13 |

Sugar Fraction & Feed Preparation and Decontamination

A 300 L container and mixing tank clean in place (CIP) was completed. 120 L of hot softened water was added to the sterile mixing tank using a 0.22 μm filter. One third of the sugar feed components, by weight, was added to the mixing tank and stirred at 150 rpm for 10 minutes until they were completely dissolved. Subsequently, the additional two thirds of sugar feed components and 120 L of hot softened water were added to the mixing tank and completely dissolved. The sugar feed was filtered sterilized using a 0.2 μm filter and stored in the sterile 300 L container.

3500 L Culture Media Preparation and Decontamination

To generate the NAGT media, a 3,500 L stirred fermenter is sterilized by CIP and fitted with calibrated pH and redox sensing probes. A total of 400 L of 0.22 μm filtered water was added to a presterilized mixing tank and combined with NAGT culture media components. The mixture was homogenized for 10 min at 150 rpm. The concentrated media was transferred to the 3500 L bioreactor and 3070 L of 0.22 μm filtered softened water is added to the fermenter. The pH of the culture media was adjusted to pH=6.5. The media was sterilized in place at 121° C. for 20 mins. Using a steam sterilized connection, 100 L of the sugar feed was added to the sterilized NAGT culture medium. The completed NAGT culture medium was then degassed using a sparger adding a $N_2H_2CO_2$ (90:5:5) gas mix at a rate of 0.1 vvm while stirring at 100 rpm and maintaining a headspace pressure of 0.2 bar. The redox value of the NAGT media was monitored from the start of degassing. The degassing continued until the redox value dropped and maintained at a steady value for 1 hour. The NAGT was then stored at 10° C.±2° C. with 90 RPM stirring and sparging 0.01 vvm of gas mix until use.

20 L and 300 L Fermenter Preparation and Decontamination and Media Transfer

A 20 L and 300 L fermenter clean in place (CIP) was completed. 17 L and 300 L of sterile culture media was transferred to the 20 L fermenter and 300 L fermenter, respectively, using a sterile connector from the 3500 L fermenter.

Initial Inoculation Preparation

Figure 21:
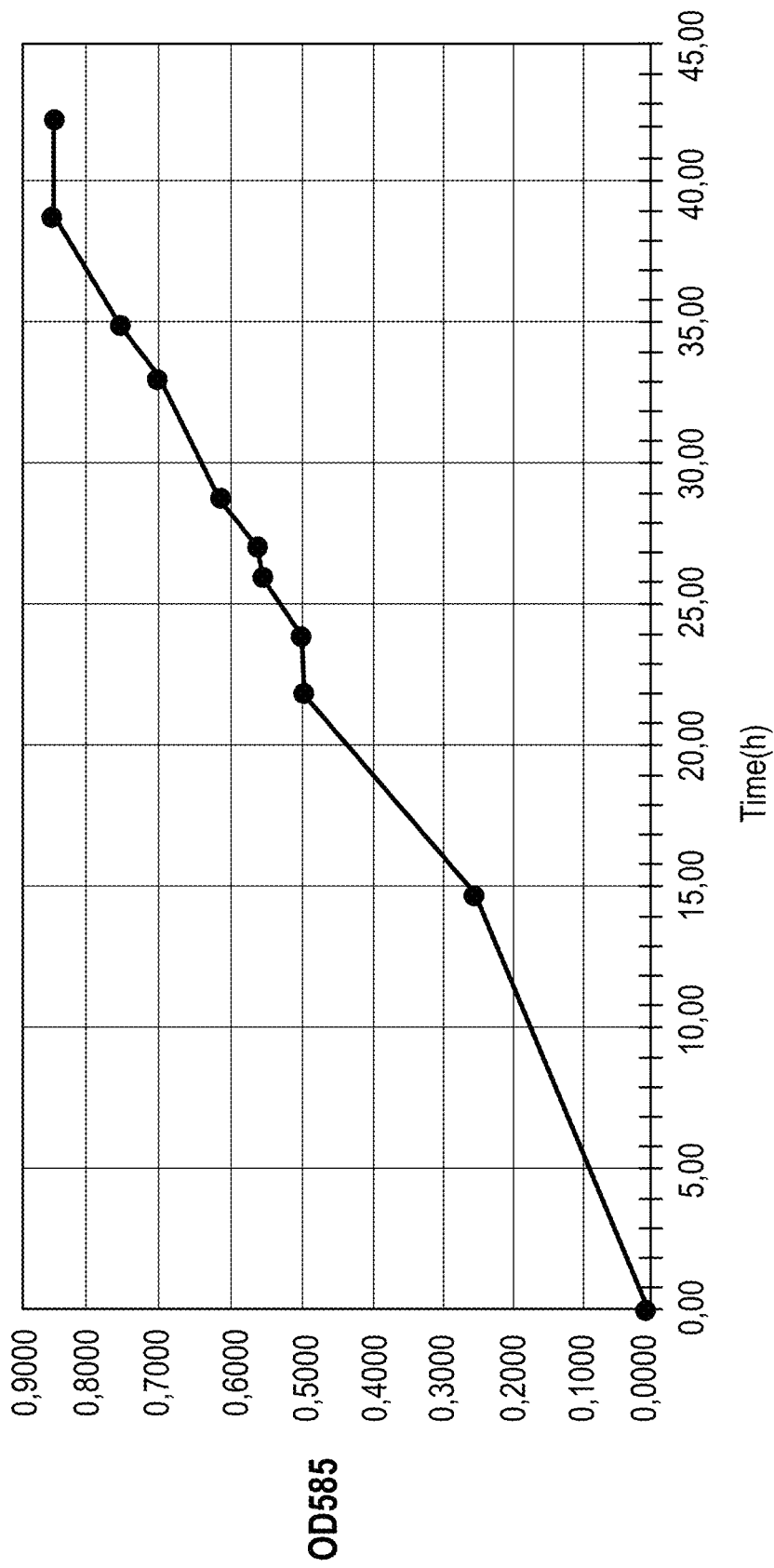
FIG. 21 shows a chart of light absorption at 585 nanometer wavelength (Y-axis) versus time for the growth of a 1 L *A. muciniphila* (DSM 33213) culture in NAGT media in a 1 L bottle in a 3500 L manufacturing process.

1 L of sterile NAGT media was transferred from the 20 L fermenter to a sterile 1 bottle. The sterile bottle was then transferred to an anaerobic chamber. 19.2 mL of WCB *A. muciniphila* (DSM 33213) was thawed in the anaerobic chamber and inoculated in the 1 L of reduced NAGT media (2% v/v inoculation rate) using a sterile pipette inoculate. The cell and media mixture were homogenized by gently swirling and incubated at 37° C. with periodic optical density measurements at 585 nm ($OD_{600}$). FIG. 21 shows that the $OD_{585}$ of the culture rose steadily during this period. The culture was stopped when a) $OD_{600}$>1, or b) if the culture grew for 48 hours.

20 L Inoculation

20 L culture media was warmed to 37° C. The media was degassed using the parameters listed in TABLE 18.

TABLE 18

Parameters for degassing inoculation.

| Parameter | Setting |
|---|---|
| Stirring | 100 rpm |
| Temperature | 37 ± 2° C. |
| pH | 6.5 |
| Gas | $N_2H_2CO_2$ (90:5:5) |
| Gas flow rate | 0.01 vvm |
| Overlay | 0.2 Bar |

Figure 22:
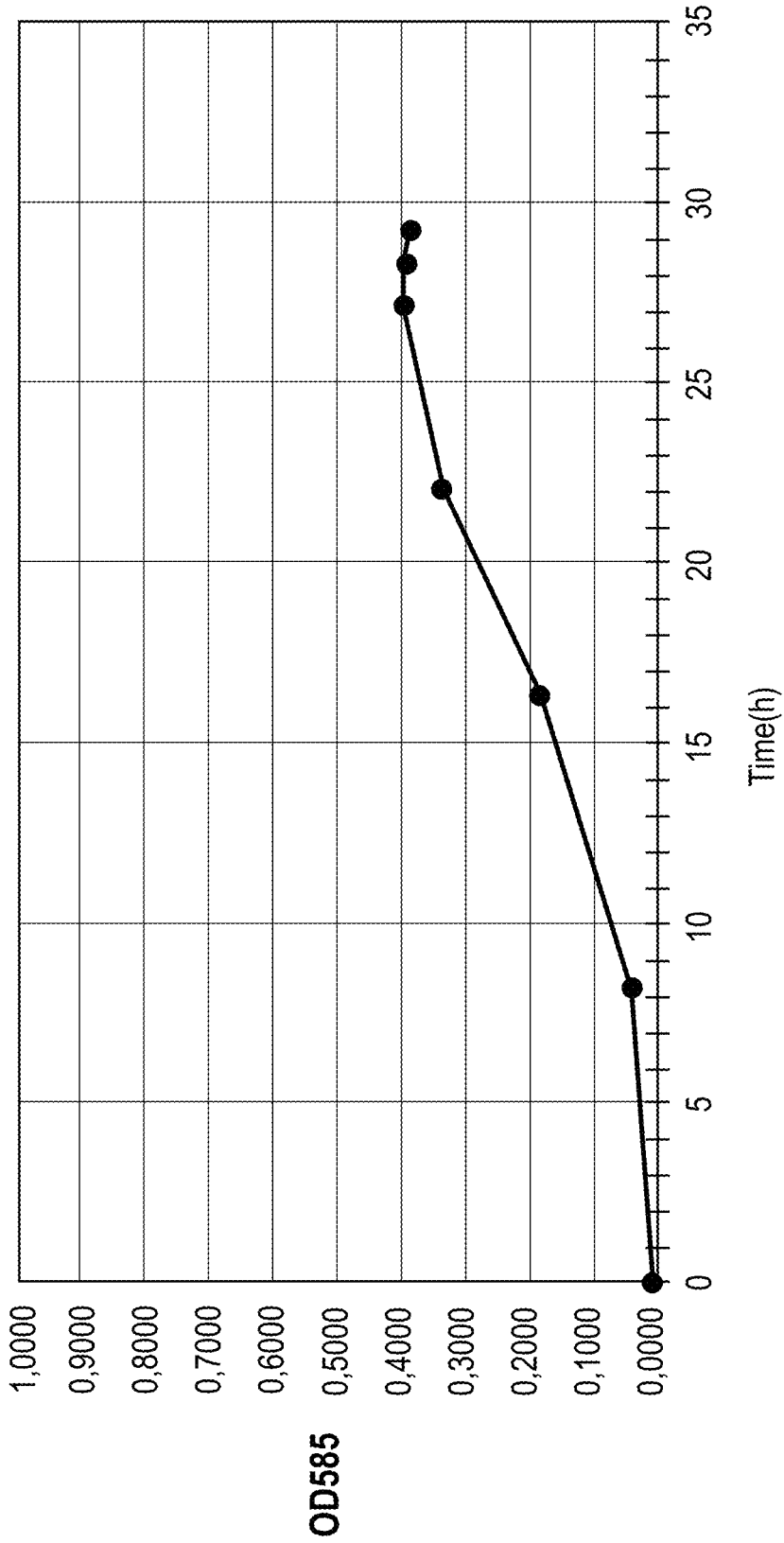
FIG. 22 shows a chart of light absorption at 585 nanometer wavelength (Y-axis) versus time for the growth of a 20 L *A. muciniphila* (DSM 33213) culture in NAGT media in a 20 L fermenter in a 3500 L manufacturing process.

The degassing continued until the redox value stabilized for 1 hour, as measured by the standard redox sensor. A sterilized 3-way valve was connected to the 20 L fermenter. The entire 1 L inoculum culture of *A. muciniphila* (DSM 33213) (5% v/v inoculum) was added to the 20 L fermenter via the 3-way valve. The optical density of the 20 L culture was monitored using $OD_{585}$. FIG. 22 shows that the $OD_{585}$ of the culture rose steadily during this period. The culture was stopped when any one of the following criteria was reached: a) $OD_{585}>1.5$, b) total culture time reached 48 hours, or c) a slowing of the growth rate was detected after three subsequent $OD_{585}$ readings.

300 L Inoculation

Figure 23:
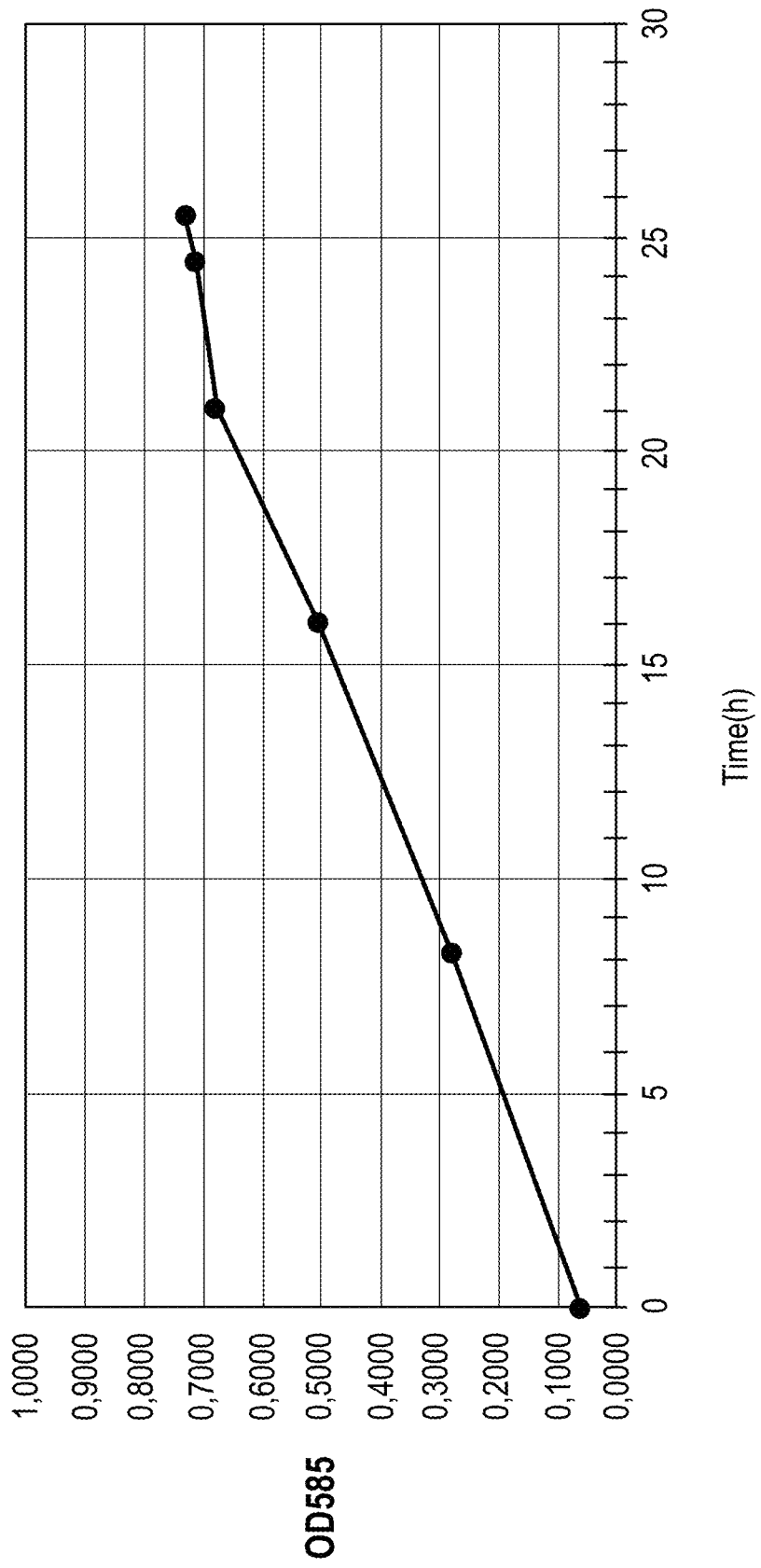
FIG. 23 shows a chart of light absorption at 585 nanometer wavelength (Y-axis) versus time for the growth of a 300 L *A. muciniphila* (DSM 33213) culture in NAGT media in a 300 L fermenter in a 3500 L manufacturing process.

300 L culture media was warmed to 37° C. The media was degassed using the parameters listed in TABLE 18. The degassing continued until the redox value stabilized for 1 hour, as measured by the standard redox sensor. A sterilized 3-way valve was connected to the 300 L fermenter. 15 L inoculum culture of *A. muciniphila* (DSM 33213) (5% v/v inoculum) from the 20 L fermenter was added to the 300 L fermenter via the 3-way valve. The optical density of the 20 L culture was monitored using $OD_{585}$. FIG. 23 shows that the $OD_{600}$ of the culture rose steadily during this period. The culture was stopped when any one of the following criteria was reached: a) $OD_{585}>1.5$, b) total culture time reached 48 hours, or c) a slowing of the growth rate was detected after three subsequent $OD_{585}$ readings.

3500 L Inoculation

Figure 24:
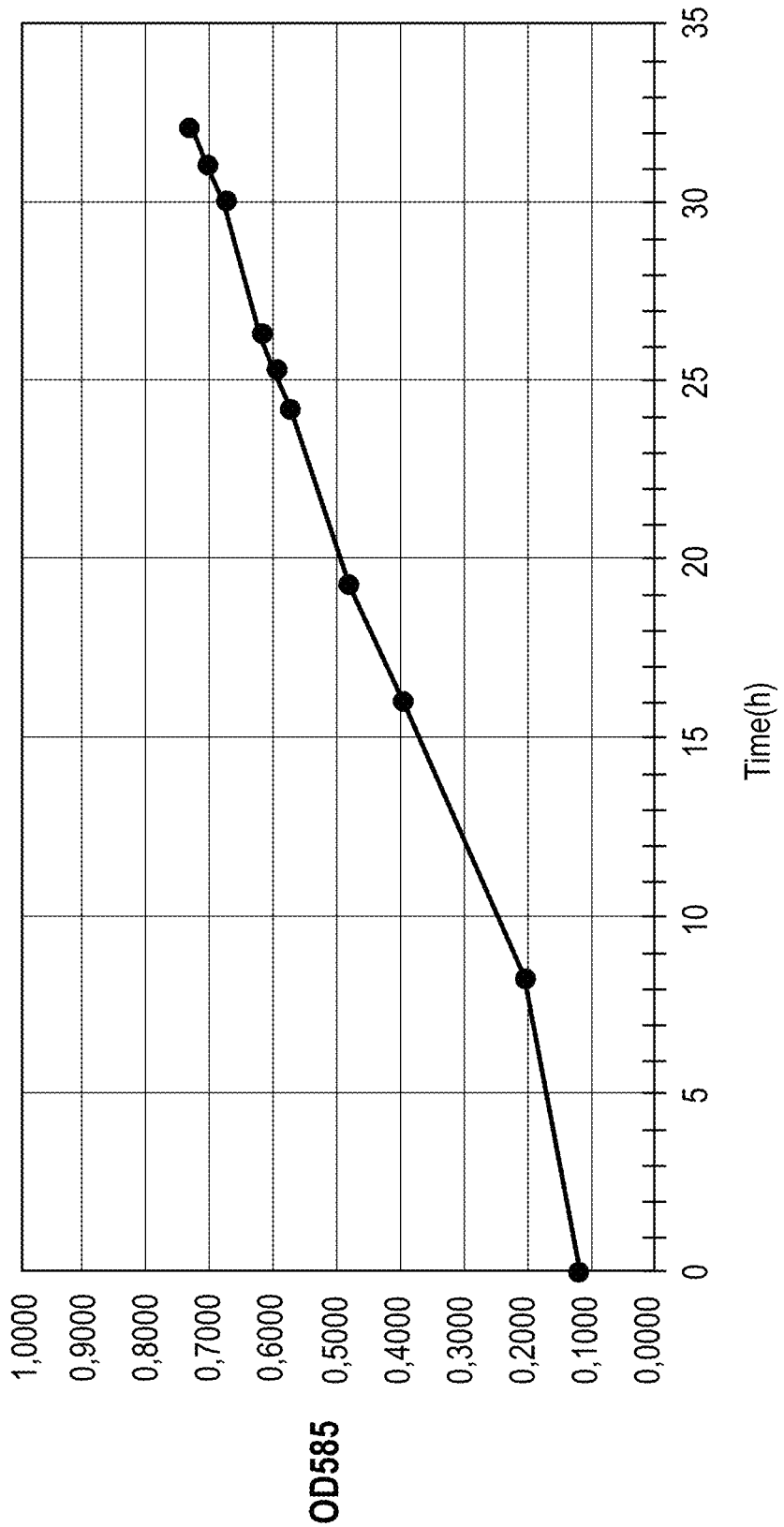
FIG. 24 shows a chart of light absorption at 585 nanometer wavelength (Y-axis) versus time for the growth of a 3500 L *A. muciniphila* (DSM 33213) culture in NAGT media in a 3500 L fermenter in a 3500 L manufacturing process.

3500 L culture media was warmed to 37° C. The media was degassed using the parameters listed in TABLE 18. The degassing continued until the redox value stabilized for 1 hour, as measured by the standard redox sensor. The 300 L fermenter was connected to the 3500 L fermenter. 300 L inoculum culture of *A. muciniphila* (DSM 33213) (8-10% v/v inoculum) from the 300 L fermenter was added to the 3500 L fermenter via the. Another 90 L of the sugar feed was added once glucose concentrations dropped below 2 g/L. The optical density of the 20 L culture was monitored using $OD_{585}$. FIG. 24 shows that the $OD_{585}$ of the culture rose steadily during this period. The culture was stopped when any one of the following criteria was reached: a) $OD_{585}>2.5$, b) total culture time reached 72 hours, or c) a slowing of the growth rate was detected after three subsequent $OD_{585}$ readings. When one of these parameters was met, the fermenter was set to 4° C.+/−3° C. to start cooling the culture.

Centrifugation

The GEA centrifuge and mixing tank clean in place (CIP) was completed. The mix gas line ($N_2H_2CO_2$, 90:5:5) was connected to and degas the GEA centrifuge and mix tank for 30 mins. The 3500 L culture was centrifuged using the Sharples parameter listed in TABLE 19.

TABLE 19

Sharples Parameter for the Centrifugation of the 3500 L culture.

| Parameter | Setting |
| --- | --- |
| Feed flow rate | 600 L/h |
| Counter Pressure | 1.5 bar |

The concentrated bacteria fraction (biomass) was collected in the degassed mix tank. The weight of the concentrated biomass collected was weighted.

Cryoprotectant Solution Preparation and Addition to Concentrated Biomass

The mixing tank clean in place (CIP) was completed. 75 L of 0.22 μm filtered hot softened water was added to the mix tank. One third of the cryoprotectant mix components was added to the mixing tank until they were completely dissolved. An additional 20 L of softened, filtered water was added. The mixture was homogenized for 10 min at 150 rpm. The cryoprotectant solution was transferred to a sterile bioreactor. The baseline redox value of the solution was recorded. The cryoprotectant solution was degassed using the parameters listed in TABLE 20.

TABLE 20

Parameters for degassing the cryoprotectant solution.

| Parameter | Setting |
| --- | --- |
| Stirring | 100 rpm |
| Gas | $N_2H_2CO_2$ (90:5:5) |
| Gas flow rate | 0.1 vvm |
| Overlay | 0.3 Bar |

The degassed cryoprotectant solution was added to the anaerobic concentrated biomass in the mix tank in a 1:1 (w/w) ratio. The total mass and volume of biomass and cryoprotectant available for lyophilzation were recorded.

Lyophilization & Grinding

The sterile plastic freeze dry trays were loaded so that the total thickness does not exceed 1 cm, corresponding to 1.5 L of cell and cryoprotectant mix per tray. The trays were moved into the pre-frozen lyophilizer shelves as they were filled to expedite the freezing process. The lyophilization cycle was initiated according to the parameters listed in TABLE 21.

TABLE 21

Parameters for the lyophilization cycle of the concentrated biomass.

| Procedure | Step | Shelf temperature (° C.) | Ramp time (hour) | Hold time (hour) | Vacuum (μBar) |
| --- | --- | --- | --- | --- | --- |
| Freezing | 1 | −45 | 0 | 3 | None |
| Vacuum pull-down | 2 | −45 | 0 | 1 | 400 |
| Primary drying | 3 | −5 | 26 | Wait until the cell mixture temperature was > −8° C. | 400 |
| Secondary Drying | 4 | 25 | 4 | ≥11.5 | 27 |

The lyophilized material was ground on speed 1, using the spacer 1 and a 1 mm grid. After grinding, the lyophilized cell material was immediately sealed in polyethylene (PE) bags, each containing 1.5 kg or less material. The lyophilized cell material was stored at <−18° C. and be used to manufacture Composition A, as defined in Example 2.

Example 11: Optimized and Ultra-Large-Scale Growth and Manufacturing Process for *Faecalibacterium prausnitzii* (DSM 33185) Drug Substance (3500 L)

Figure 25:
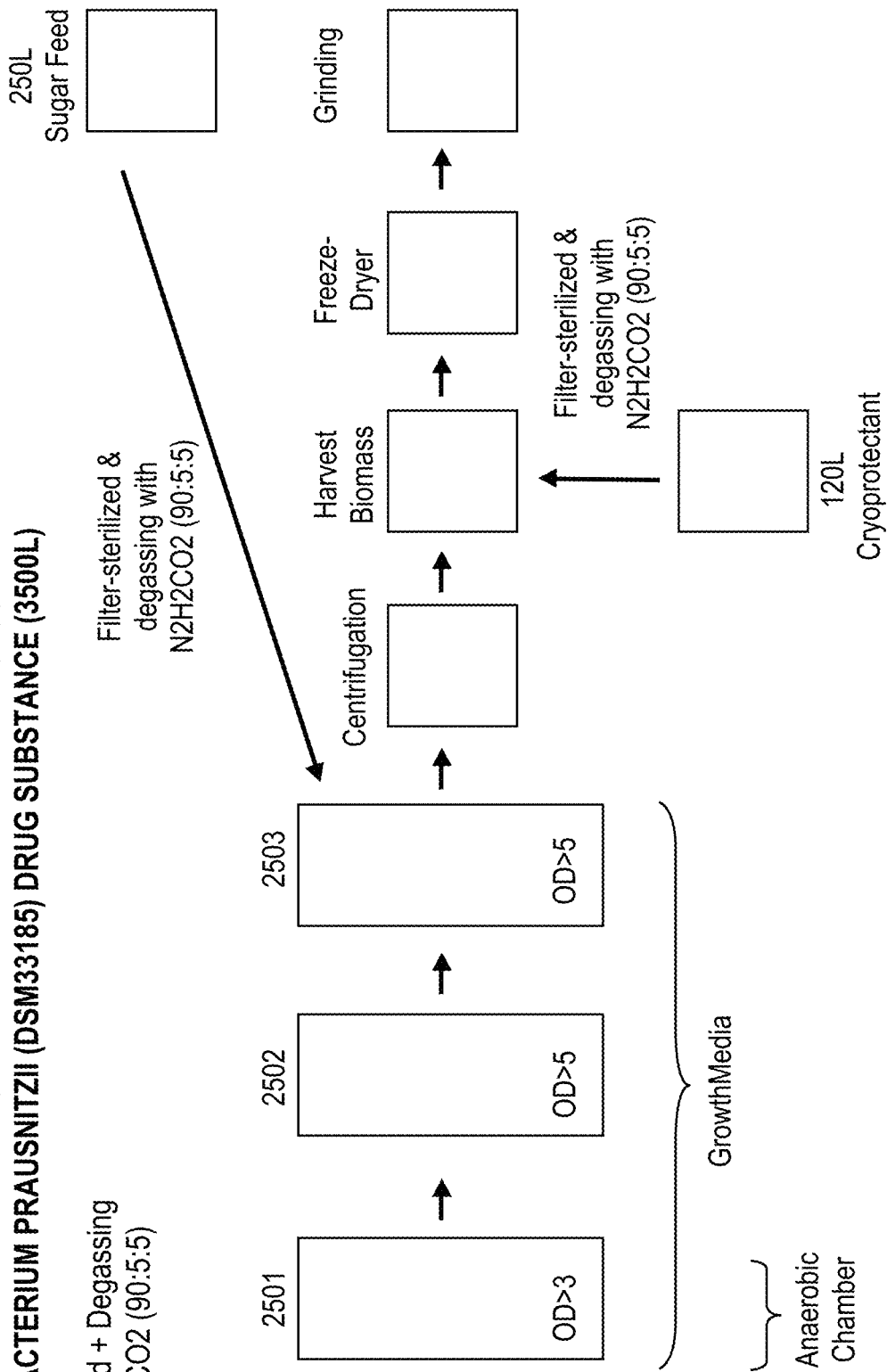
FIG. 25 shows a schematic flow chart for an optimized and ultra-large-scale growth and manufacturing process for *F. prausnitzii* (DSM 33185) in 3500 L culture volume. 6.4 mL of Working Cell Bank (WCB) *F. prausnitzii* (DSM 33185) was thawed in the anaerobic chamber and inoculated in 1 L of reduced NAGT media (2% v/v inoculation rate) in a 2 L flask 2501 in an anaerobic chamber. The cultured was stopped when either $OD_{600}$>3 or the culture grew for 48 hours. 1.5 L culture in 2501 was used to inoculate in 150 L media (1% v/v inoculation rate) in a 300 L fermenter 2502. The cultured was stopped when either $OD_{585}$>5 or the culture grew for 48 hours. 250 L, defined in TABLE 22, was prepared. 100 L sugar feed was added to a 3500 L fermenter 2503. 35 L culture in 2502 was used to inoculate in 300 L media (5% v/v inoculation rate) in a 3500 L fermenter 2503. The cultured was stopped when either $OD_{585}$>5 or the culture grew for 72 hours. The entire culture in 2503 was then centrifuged under anaerobic atmosphere and harvested as a biomass. 120 L filter-sterilized degassed cryoprotectant, defined in TABLE 24, was mixed with the biomass in a mixing tank purged with anaerobic gas. The biomass with cryoprotectant was lyophilized (frozen and dried) and ground. For each step, the media used for the bacterial culture were sterilized (autoclaving at 121° C.) and degassed with $N_2H_2CO_2$ (90:5:5) before use. Sugar components (glucose) was prepared separately from the remaining YFAP media components. Sugar feed was filter sterilized, degassed, and added to the remaining YFAP media components to generate the complete culture media.

Manufacturing conditions and procedures for growing *Faecalibacterium prausnitzii* (DSM 33185) in 3500 L volume of culture, as outlined in FIG. 25, were generated to increase yield and growth rate of bacterial strains described herein.

Media Preparation

The components for the 250 L sugar feed (TABLE 22), 3160 L of YFAP media (TABLE 23), and cryoprotectant mix (TABLE 24) were weighted.

TABLE 22

Recipe for the 250 L sugar feed for
F. prausnitzii (DSM 33185).

| Components | Weight (kg) for 250 L feed |
|---|---|
| Dextrose | 85 |

TABLE 23

Recipe for the 3160 L YFAP Media.

| Components | Weight (kg, unless specified otherwise) for 3160 L YFAP media |
|---|---|
| Pea peptone | 63.3 |
| Yeast extract | 15.8 |
| Sodium chloride | 3.16 |
| Sodium bicarbonate | 3.16 |
| Dibasic potassium phosphate | 7.9 |
| Magnesium sulfate heptahydrate | 0.632 |
| Sodium acetate | 15.8 |
| L-cysteine HCl | 3.16 |
| Vitamin Mix solution | 632 ml |

TABLE 24

Recipe for 120L Cryoprotectant Mix.

| Components | Weight (kg) for 120 L cryoprotectant mix |
|---|---|
| Saccharose | 9.6 |
| Trehalose | 1.596 |
| Sodium Glutamate | 0.66 |
| L-Cysteine HCl | 0.156 |

Sugar Fraction & Feed Preparation and Decontamination

A 300 L container and mixing tank clean in place (CIP) was completed. 120 L of hot softened water was added to the sterile mixing tank using a 0.22 μm filter. One third of the sugar feed components, by weight, was added to the mixing tank and stirred at 150 rpm for 10 minutes until they were completely dissolved. Subsequently, the additional two thirds of sugar feed components and 130 L of hot softened water were added to the mixing tank and completely dissolved. The sugar feed was filtered sterilized using a 0.2 μm filter and stored in the sterile 300 L container.

3500 L Culture Media Preparation and Decontamination

The To generate the YFAP media, a 3,500 L stirred tank bioreactor is sterilized by CIP and fitted with calibrated pH and redox sensing probes. A total of 400 L of 0.22 μm filtered water is added to a pre-sterilized mixing tank and combined with YFAP culture media components and homogenized for 10 min at 150 rpm. The concentrated media is transferred to the 3500 L bioreactor and 3070 L of 0.22 μm filtered softened water is added to the bioreactor. Using a steam sterilized connection, 100 L of the sugar feed is added to the sterilized YFAP culture medium. 632 ml Vitamin Mix solution was added. The completed YFAP culture medium is then degassed using a sparger adding a $N_2H_2CO_2$ (90:5:5) gas mix at a rate of 0.1 vvm while stirring at 100 rpm and maintaining a headspace pressure of 0.2 bar.

Figure 26:
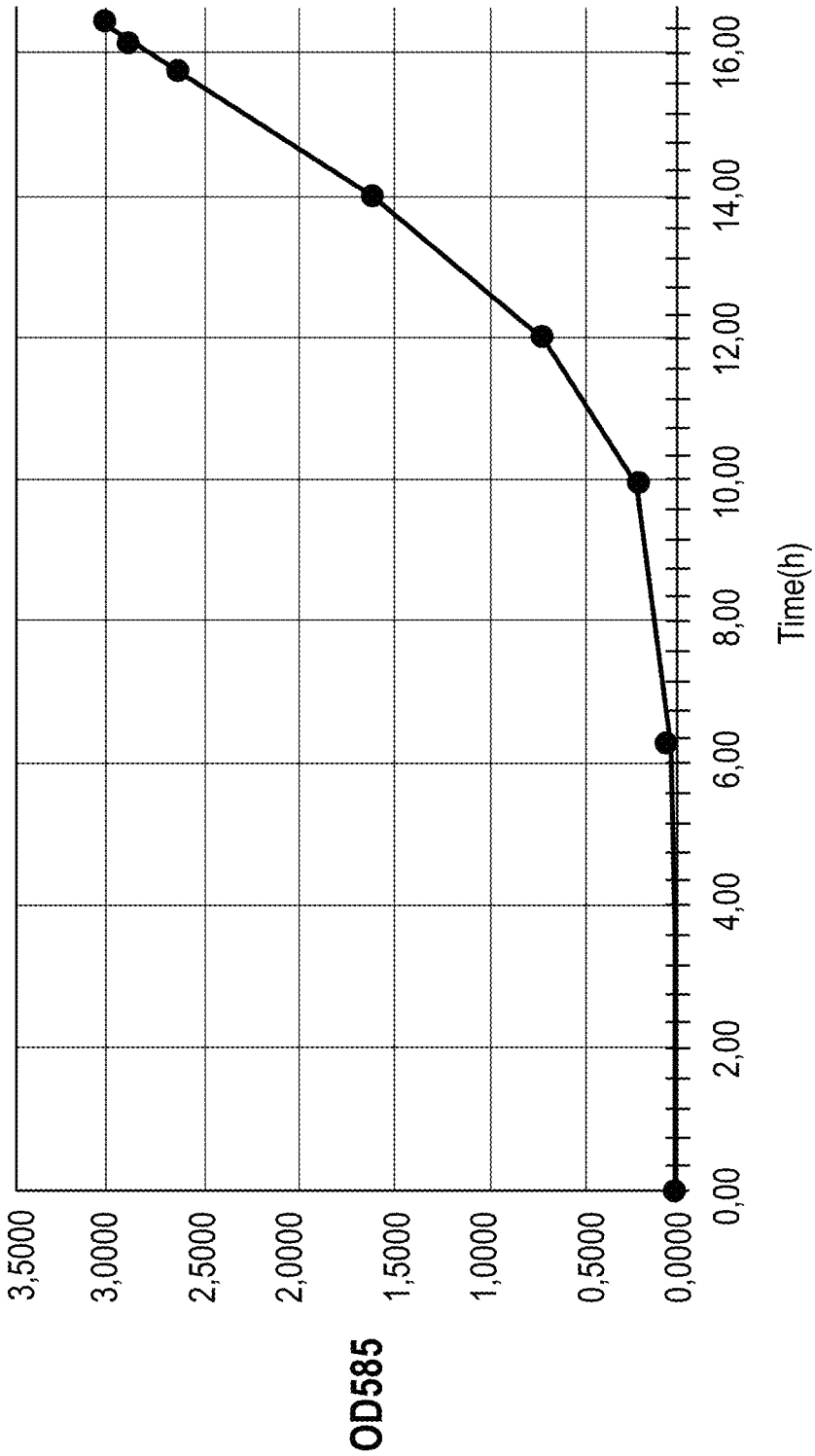
FIG. 26 shows a chart of light absorption at 585 nanometer wavelength (Y-axis) versus time for the growth of a 2 L *F. prausnitzii* (DSM 33185) culture in YFAP media in a 2 L flask in a 3500 L manufacturing process.

Initial Inoculation Preparation 1.6 L of sterile YFAP media was transferred from the 300 L fermenter to a sterile 2 L flask. The sterile bottle was then transferred to an anaerobic chamber. 6.4 mL of WCB F. prausnitzii (DSM 33185) was thawed in the anaerobic chamber and inoculated in the 1 L of reduced YFAP media (0.4% v/v inoculation rate) using a sterile pipette inoculate. The cell and media mixture were homogenized by gently swirling and incubated at 37° C. with periodic optical density measurements at 585 nm ($OD_{585}$). FIG. 26 shows that the $OD_{585}$ of the culture rose steadily during this period. The culture was stopped when a) $OD_{585}$>3, or b) if the culture grew for 48 hours.

300 L Inoculation

150 L of sterile culture media was transferred to a sterile 300 L fermenter The YFAP culture media in the 300 L fermenters was degassed with a $N_2H_2CO_2$ (90:5:5) using the sparger for 2 hours at 0.1 vvm 300 L culture media was warmed to 37° C. The media was degassed using the parameters listed in TABLE 18.

Figure 27:
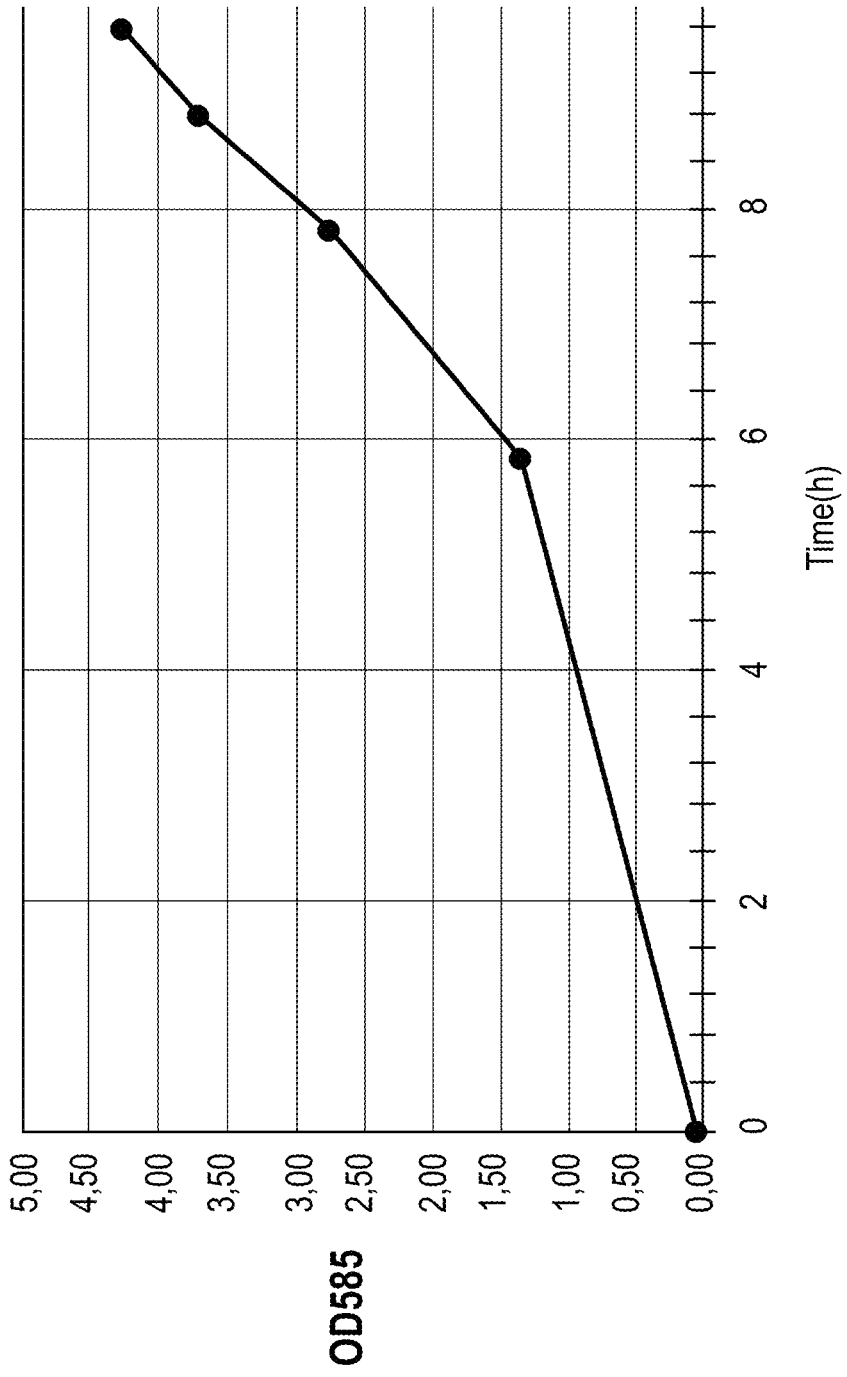
FIG. 27 shows a chart of light absorption at 585 nanometer wavelength (Y-axis) versus time for the growth of a 150 L *F. prausnitzii* (DSM 33185) culture in YFAP media in a 300 L fermenter in a 3500 L manufacturing process.

The degassing continued until the redox value stabilized for 1 hour, as measured by the standard redox sensor. A sterilized 3-way valve was connected to the 300 L fermenter. The entire 1 L inoculum culture of F. prausnitzii (DSM 33185) (2% v/v inoculum) was added to the 20 L fermenter via the 3-way valve. The optical density of the 20 L culture was monitored using $OD_{585}$. FIG. 27 shows that the $OD_{585}$ of the culture rose steadily during this period. The culture was stopped when any one of the following criteria was reached: a) $OD_{585}$>5, b) total culture time reached 48 hours, or c) a slowing of the growth rate was detected after three subsequent $OD_{585}$ readings.

3500 L Inoculation

Figure 28:
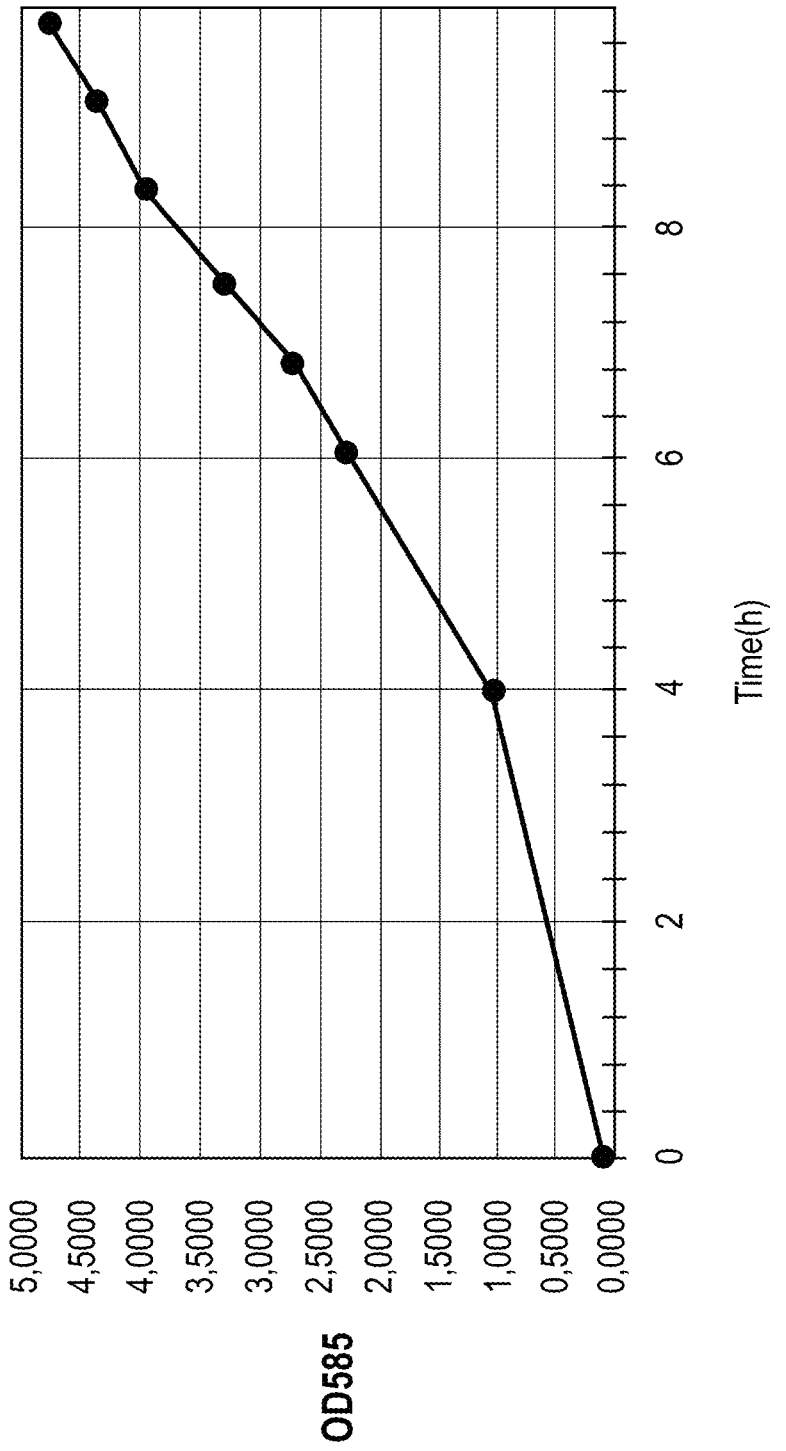
FIG. 28 shows a chart of light absorption at 585 nanometer wavelength (Y-axis) versus time for the growth of a 3500 L *F. prausnitzii* (DSM 33185) culture in YFAP media in a 3500 L fermenter in a 3500 L manufacturing process.

About 3500 L culture media was warmed to 37° C. The media was degassed using the parameters listed in TABLE 18. The degassing continued until the redox value stabilized for 1 hour, as measured by the standard redox sensor. The 300 L fermenter was connected to the 3500 L fermenter. 30 L inoculum culture of F. prausnitzii (DSM 33185) (8-10% v/v inoculum) from the 300 L fermenter was added to the 3500 L fermenter via the. The optical density of the 20 L culture was monitored using $OD_{585}$. FIG. 28 shows that the $OD_{585}$ of the culture rose steadily during this period. The culture was stopped when any one of the following criteria was reached: a) $OD_{585}$>5, b) total culture time reached 72 hours, or c) a slowing of the growth rate was detected after three subsequent $OD_{585}$ readings. When one of these parameters was met, the fermenter was set to 4° C.+/−3° C. to start cooling the culture.

Centrifugation

The GEA centrifuge and mixing tank clean in place (CIP) was completed. The mix gas line ($N_2H_2CO_2$, 90:5:5) was connected to and degas the GEA centrifuge and mix tank for 30 mins. The 3500 L culture was centrifuged using the Sharples parameter listed in TABLE 19.

The concentrated bacteria fraction (biomass) was collected in the degassed mix tank. The weight of the concentrated biomass collected was weighted.

Cryoprotectant Solution Preparation and Addition to Concentrated Biomass

The mixing tank clean in place (CIP) was completed. 75 L of 0.22 μm filtered hot softened water was added to the mix tank. One third of the cryoprotectant mix components was added to the mixing tank until they were completely dissolved. An additional 20 L of softened, filtered water was added. Subsequently, the additional two thirds of cryoprotectant components were added to the mixing tank and dissolved. The mixture was homogenized for 10 min at 150 rpm. The cryoprotectant solution was transferred to a sterile bioreactor. The baseline redox value of the solution was recorded. The cryoprotectant solution was degassed using the parameters listed in TABLE 18.

The degassed cryoprotectant solution was added to the anaerobic concentrated biomass in the mix tank in a 1:1 (w/w) ratio. The total mass and volume of biomass and cryoprotectant available for lyophilzation were recorded.

Lyophilization & Grinding

The sterile plastic freeze dry trays were loaded so that the total thickness does not exceed 1 cm, corresponding to 1.5 L of cell and cryoprotectant mix per tray. The trays were moved into the pre-frozen lyophilizer shelves as they were filled to expedite the freezing process. The lyophilization cycle was initiated according to the parameters listed in TABLE 21.

The lyophilized material was ground on speed 1, using the spacer 1 and a 1 mm grid. After grinding, the lyophilized cell material was immediately sealed in polyethylene (PE) bags, each containing 1.5 kg or less material. The lyophilized cell material was stored at <−18° C. and be used to manufacture Composition A, as defined in Example 2.

Example 12: Clinical Study Design

The design of a first in human study is used to evaluate an orally administrable pharmaceutical composition comprising a bacterial consortium consisting of the bacterial strains *Akkermansia muciniphila* (DSM 33213), *Faecalibacterium prausnitzii* (DSM 33185), and *Lactobacillus crispatus* (DSM 33187) is provided for prevention and treatment of allergic disease.

The study of this example is designed as a Phase 1b, multi-centered, randomized, double-blind, placebo-controlled, parallel group, three sequential part study of the bacterial consortium consisting of the bacterial strains *Akkermansia muciniphila* (DSM 33213), *Faecalibacterium prausnitzii* (DSM 33185), and *Lactobacillus crispatus* (DSM 33187) in multi-sensitized (to two or more allergens) human subjects who are otherwise healthy.

Therapeutic function of bacterial Composition A is evaluated by determining change in circulating IgE (both total and specific) levels, immune cell counts, stool microbiome composition, stool and plasma metabolic profile, stool and plasma immune stimulatory capacity (in-vitro analysis), and symptom scores from Baseline to End of the Treatment.

Figure 29:
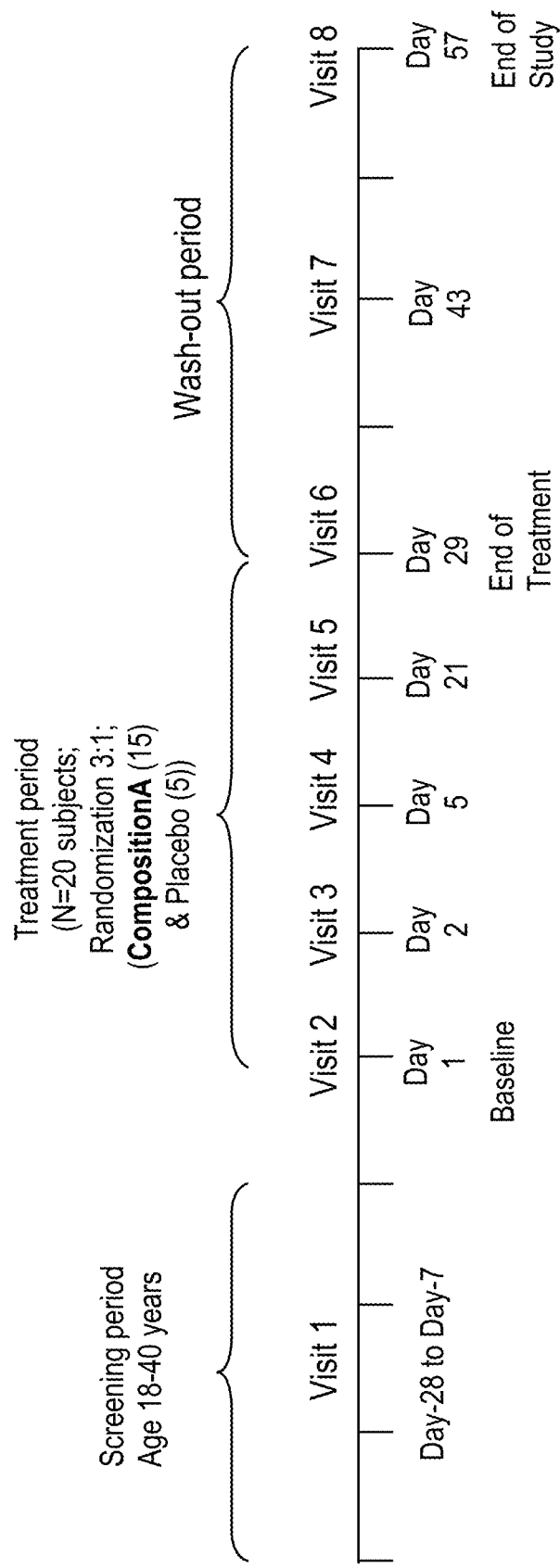
FIG. 29 shows the three stages (screening period, treatment period, and washout period) of a human clinical study as described herein, as well as its ability to treat allergy in subjects of varying age compared to placebo, by orally administering the pharmaceutical compositions to the subjects.

Subjects are separated into 3 categories (see e.g., FIG. 29). The first category contains approximately 20 subjects, 18-40 years of age, multi-sensitized to two or more allergens, who are otherwise healthy (male:female; approximately 1:1) (randomized 3:1 test:Placebo); the second category contains approximately 20 subjects, 12-17 years of age, multi-sensitized to two or more allergens, who are otherwise healthy (male:female; approximately 1:1) (randomized 3:1 test:Placebo); and the third category contains approximately 20 subjects 2-11 years of age, multi-sensitized to two or more allergens, who are otherwise healthy (male:female; approximately 1:1). Subjects are randomized 3:1 with regards to Composition A vs. placebo.

Treatment of human subjects consists of twice daily oral administration (approximately every 12 hours+/−4 hours by mixing with food or milk) of Composition A for 28 days. Each 1 mL dose of Composition A contains 5×10^8 CFU/bacterial species of each *Lactobacillus* crispatus (DSM 33187), *Akkermansia muciniphila* (DSM 33213), and *Faecalibacterium prausnitzii* (DSM 33185).

Composition A is a live biotherapeutic product containing three live bacterial strains, each present at 5×10^8 CFU per dose: *Lactobacillus crispatus* (DSM 33187), *Faecalibacterium prausnitzii* (DSM 33185), and *Akkermansia muciniphila* (DSM 33213). Composition A is supplied as a single frozen glycerol stock containing all three bacterial species. Each dose of Composition A is provided in a 2 mL polypropylene screw cap vial with a silicone washer seal. The vial contains all three live bacterial strains suspended in a buffered glycerol solution. The buffered glycerol solution is composed of standard phosphate buffered saline (PBS, 137 mM NaCl, 2.7 mM KCl, 10 mM $Na_2HPO_4$, and 1.8 mM $KH_2PO_4$), 20% v/v glycerol, and 0.1% w/w cysteine as an antioxidant. The volume of the Composition A dose is approximately 1 mL.

For the purpose of this example, Composition A is stored at −70° C., and a temperature log is maintained. Once provided to the human subjects, Composition A is stored in a freezer at or below −18° C. Composition A doses are maintained sealed in its cryovial (e.g., 2 mL cryovial) containers prior to thawing for consumption to maintain the potency and purity of the product. The frozen stocks of Composition A are thawed at room temperature for 5-10 minutes and immediately consumed as mentioned in dosing instructions.

The placebo treatment in this example consists of twice daily oral administration (approximately every 12±4 hours by mixing with food or milk) of excipients (Placebo: phosphate buffered saline (PBS) as described for product formulation with 20% v/v glycerol and 0.1% w/w cysteine) for 28 days. Each 1 mL dose will be identical in volume to the test product. The frozen stock is thawed at room temperature for 5-10 minutes. After which the contents of the vial are immediately mixed in adequate quantity (1-2 ounces) of cold or room temperature milk (including breast milk, liquid infant formulas, cow's milk, almond milk, and soy milk) or foods such as applesauce and yogurt.

As illustrated in FIG. 29, screening visits are conducted from 28 days up to 7 days prior to day 1 (baseline visit). Dosing begins on Day 1. Subjects are treated for 28 days with subsequent visits on days 8, 15, 22, and 29. Follow-up visits are conducted on days 43 and 57. Each visit after baseline has a window of ±1 day.

Assessments are performed during the 28 days treatment period and up to 28 days (Day 57) of washout thereafter by (i) reporting adverse events; (ii) reporting concomitant medications; (iii) performing physical examinations and vital signs; and (iv) laboratory tests including serum chemistry, liver and renal function panels, hematology, complete blood count with differential, and urinalysis. In the third part of this study, blood and urine samples are not collected for safety assessments. All other assessments, except those requiring blood and urine sampling, are performed.

Additional assessments are performed by evaluating change from Baseline to End of the Treatment in the following parameters: (i) stool microbiome analysis (bacterial composition); (ii) stool and plasma metabolic profiling; (iii) stool and plasma immune stimulatory capacity (in-vitro analysis); (iv) total IgE and specific IgE levels; (v) circulating immune cell profiling; (vi) questionnaire(s) and adverse effect (AE) and medication use reporting in diary.

Various laboratory variables are determined in this study. Hematological variables include hematocrit, hemoglobin, mean corpuscular hemoglobin, mean corpuscular hemoglobin concentration, mean corpuscular volume, platelet count, red blood cell distribution width, red blood cell count, and white blood cell count with differential. Urinalysis parameters include appearance (e.g., color and character), bilirubin, urobilinogen, protein content, glucose levels, ketones, leukocyte esterase, urine blood, nitrite, pH, and specific gravity. Biochemical parameters include glucose levels, uric acid, BUN (blood urea nitrogen), creatinine, BUN/creatinine ratio, eGFR (estimated glomerular filtration rate), sodium, potassium, chloride, bicarbonate, calcium, albumin, total bilirubin, alkaline phosphatase levels, AST (aspartate aminotransferase) levels, ALT (alanine transaminase), gamma-glutamyltransferase (GGT), total cholesterol levels, and triglyceride levels.

Example 13: Viability of Frozen Bacterial Cells

The viability of frozen *Akkermansia muciniphila* (DSM 33213), *Faecalibacterium prausnitzii* (DSM 33185), and *Lactobacillus crispatus* (DSM 33187) in glycerol was examined. About $5\times10^8$ CFUs of *A. muciniphila* (DSM 33213), about $5\times10^8$ CFUs of *F. prausnitzii* (DSM 33185), and about $5\times10^8$ CFUs of *L. crispatus* (DSM 33187) were mixed and frozen in glycerol. The frozen bacterial cells were stored in $-70°$ C. The viability of bacterial cells was scored at 1 month, 2 months, 3 months, 6 months, 9 months, and 12 months after storage. The score is listed in TABLE 22:

TABLE 22

| Viability of Frozen Bacterial Cells in Glycerol | | | | | | | |
|---|---|---|---|---|---|---|---|
| Bacteria Strain | Colony Forming Unit (CFU) at: | | | | | | |
| | 0 month | 1 month | 2 months | 3 months | 6 months | 9 months | 12 months |
| *A. muciniphila* (DSM 33213) | $4.98 \times 10^8$ | $3.19 \times 10^8$ | $7.22 \times 10^8$ | $1.01 \times 10^9$ | $6.78 \times 10^8$ | $1.45 \times 10^9$ | $2.19 \times 10^8$ |
| *F. prausnitzii* (DSM 33185) | $5.12 \times 10^8$ | $5.6 \times 10^8$ | $5.22 \times 10^8$ | $8.06 \times 10^8$ | $6.55 \times 10^8$ | $1.65 \times 10^9$ | $5.27 \times 10^8$ |
| *L. crispatus* (DSM 33187) | $5.3 \times 10^8$ | $7 \times 10^8$ | $6.84 \times 10^8$ | $4.59 \times 10^8$ | $7.7 \times 10^8$ | $6.78 \times 10^8$ | $1.75 \times 10^9$ |

Example 14: Lyophilized Drug Product Capsule and Liquid Composition Container

Figure 30:
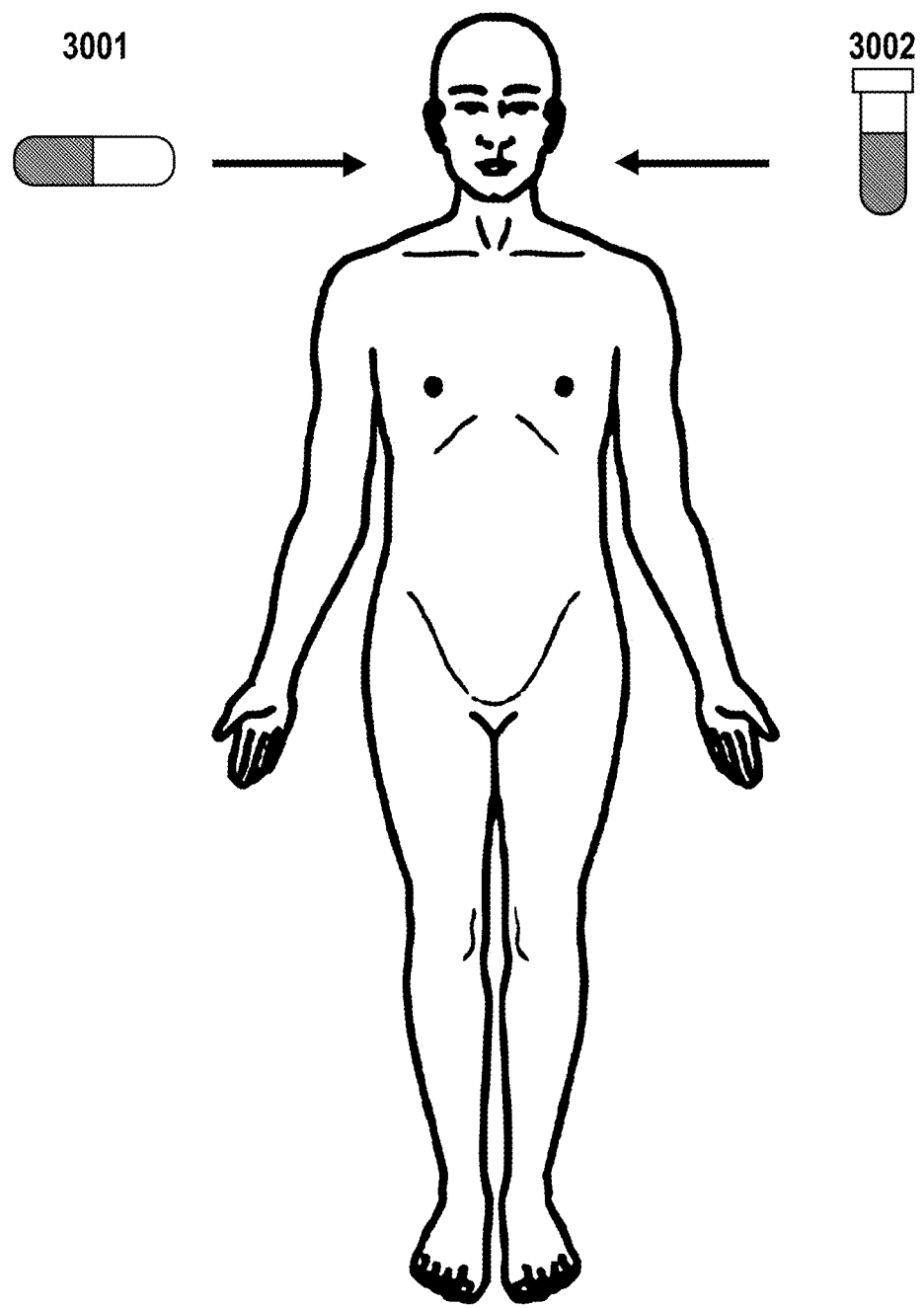
FIG. 30 shows the drug product in a solid dosage form (3001) or liquid dosage form (3002). The compositions in either form can be administered orally.

Composition A, as defined in Example 2, is encompassed in a capsule with a pharmaceutically acceptable excipient. The capsule is in standard size 0 or size 1. The capsule is made of plant-derived materials, such as tapioca pullulan. It is starch-free, gluten-free, and preservative-free. The capsule is disintegrated at $37°$ C.>90% of the capsule dissolves in water, pH=1.2 solution, sodium acetate buffer USP (pH=4.5), or sodium phosphate buffer (pH=7.2) within 60 minutes. The capsule has a disintegration endpoint of 1.6 minutes, as measured at $37°$ C. with de-ionized water. The capsule has an oxygen permeability ($cm^3/m^2$/day) of $\leq 0.5$, as measured by a gas composition in the capsule. The capsule is administered orally, as shown in FIG. 30. Composition A is also present in a 2 mL polypropylene screw cap vial and administered orally, as shown in FIG. 30.

Example 15: Clinical Study Design for Preventing Allergic Conditions in Infants and Newborns Further studies of Composition A: Each dose contains a total of $1.5\times10^9$ CFU, each in equal amounts ($5\times10^8$ CFU/*Akkermansia muciniphila* (DSM 33213), *Faecalibacterium prausnitzii* (DSM 33185), and *Lactobacillus crispatus* (DSM 33187)) and carbohydrate-based excipient, compared to placebo (identical-appearing solution of excipients) in neonate and infant subjects at high risk for development of allergic diseases. Composition A or placebo is administered 1 mL once daily for 28 days (Part A) and for 336 days (Part B), orally (by mouth), mixed into breast milk, formula, or food.

Figure 31:
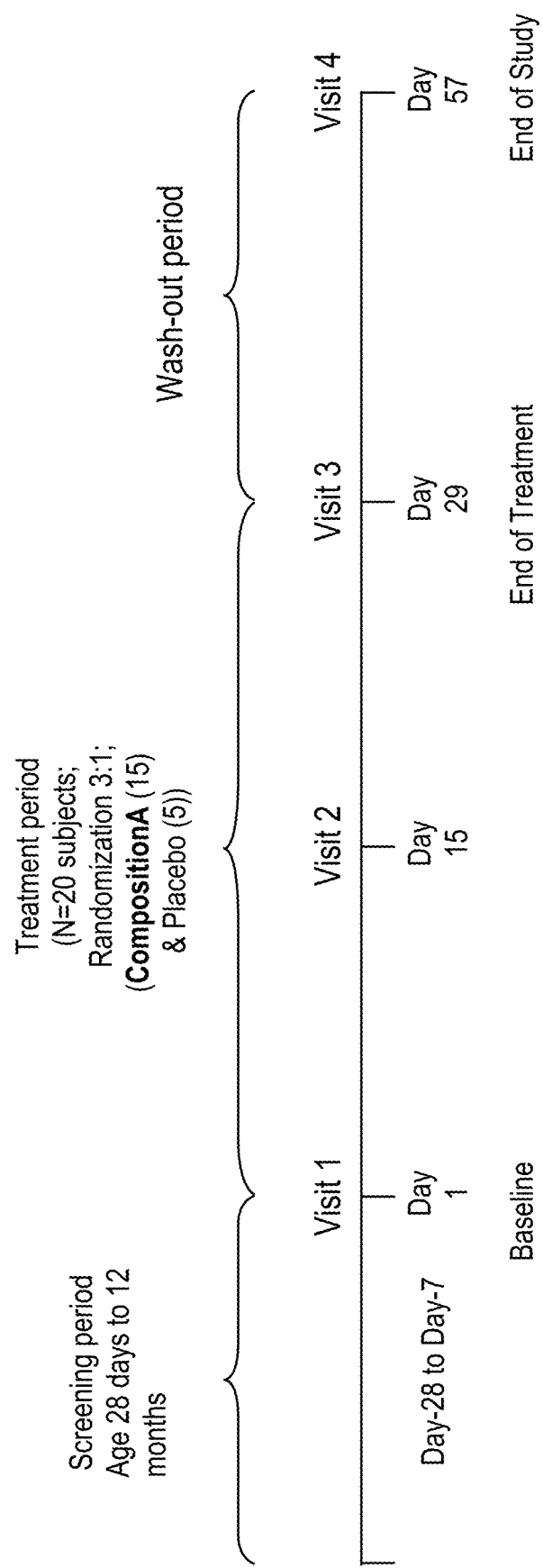
FIG. 31 shows the three stages (screening period, treatment period, and washout period) of a human clinical study as described herein, as well as its ability to treat allergy in subjects of varying age compared to placebo, by orally administering the pharmaceutical compositions to the subjects.

In Part A: As illustrated in FIG. 31, Infants aged 28 days to less than 12 months are enrolled initially for 28 days of treatment and followed for 1 additional month observation (off treatment) for evaluation of safety/tolerability prior to enrolling neonates (Part B). In Part A, eligible subjects are randomized to either: Composition A, consisting of once daily oral administration of Composition A (mixed with breast milk, formula, or food) for 28 days, or placebo, consisting of once daily oral administration of placebo (mixed with breast milk, formula, or food) for 28 days. A total of 20 eligible infants are enrolled in a 3:1 (15:5) randomization.

Figure 32:
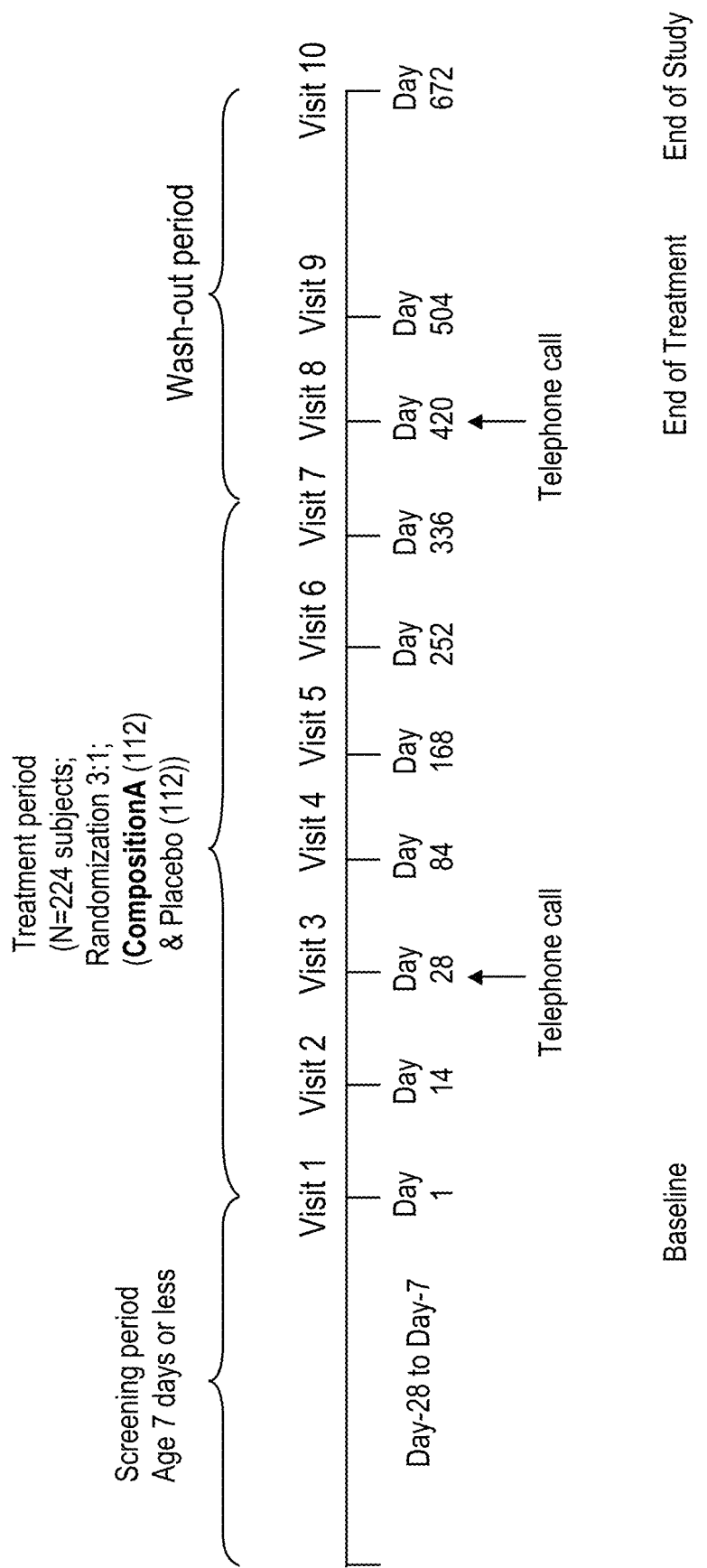
FIG. 32 shows the three stages (screening period, treatment period, and washout period) of a human clinical study as described herein, as well as its ability to treat allergy in subjects of varying age compared to placebo, by orally administering the pharmaceutical compositions to the subjects.

In Part B: As illustrated in FIG. 32, Neonates of less than or equal to 7 days of life are randomized to either Composition A, consisting of once daily oral administration of Composition A (mixed with breast milk, formula, or food) for 336 days, or Placebo, a treatment consisting of once daily oral administration of placebo (mixed with breast milk, formula, or food) for 336 days.

Eligible neonates are enrolled in a 1:1 (112:112) randomization stratified by mode of delivery (vaginal or Cesarean section) and by method of feeding at enrollment (breast feeding or no breast feeding). Potentially eligible neonates are identified during pregnancy or during the first week after birth. Administration of Composition A or placebo begins within 7 days of birth and continue for one year followed by a one-year observation period (off treatment), followed by measurements during 10 visits (8 in-clinic visits and 2 telephone calls) over 672 days from enrollment.

Immunologic biomarkers, additional stool metabolic profiling, and stool microbiome analysis in Composition A in comparison to placebo in neonate and infant subjects are measured. Therapeutic function of bacterial Composition A is evaluated (secondary endpoints) by determining change in circulating IgE (both total and specific) levels, immune cell counts, stool microbiome composition, stool and plasma metabolic profile, stool and plasma immune stimulatory capacity (in-vitro analysis), and symptom scores from Baseline to End of the Treatment.

The primary endpoint is considered a sensitive PD marker that may be associated with reduction of development of allergic disease, based on prior studies of the role of live bacterial therapeutics to potentially modify the development of allergic disease.

Additional endpoints include: incidence of physician-diagnosed Atopic Dermatitis at 168 and 672 days; incidence of physician-diagnosed Food Allergy, Chronic Rhinitis/Allergic Rhinitis, Urticaria and Wheezing Illnesses/Asthma at 168, 336, and 672 days (each diagnosis is assessed independently); incidence of sensitization to food and aeroallergen at 168, 336, and 672 days (as assessed by serum allergen specific IgE testing to egg white, peanut, cow's milk, cat, house dust mites, dog, *Alternaria* (mold) and mixed grass pollen); severity of Atopic Dermatitis (as assessed by investigator global assessment (IGA), SCORing Atopic Dermatitis (SCORAD) and IGA×BSA at 168, 336, and 672 days); severity of Wheezing Illness/Asthma (assessed by exacerbation history) at 168, 336, and 672 days; concomitant medications prescribed/used for allergic symptoms or diagnosis and use of rescue medications for atopic dermatitis and wheezing/asthma Total serum IgE levels at 168, 336, and 672 days; peripheral eosinophil counts at 168, 336, and 672 days; pharmacogenetics sample (optional); stool microbiome analysis (microbial composition); stool and plasma metabolic profiling (selected sites only); subcutaneous biomarkers and RNA seq profiling assessed by tape strips; circulating immune cell profiling (selected sites only); cord blood (biomarker/immune cell profiling) (optional; selected sites only); stool and plasma immune stimulatory capacity (ex-vivo analysis) (selected sites only); titers to tetanus/diphtheria vaccination; severity of Wheezing Illness/Asthma (assessed by Asthma Control Questionnaire (ACQ)) at 168, 336, and 672 days.

As a primary study endpoint, safety assessments are performed during the 28 days treatment period and up to 28 days (Day 57) of washout thereafter by (i) reporting adverse events; (ii) reporting concomitant medications; (iii) performing physical examinations and vital signs; and (iv) laboratory tests including serum chemistry, liver and renal function panels, hematology, complete blood count with differential, and urinalysis. In the third part of this study, blood and urine samples are not collected for safety assessments. All other assessments, except those requiring blood and urine sampling, are performed.

Secondary study assessments are performed by evaluating change from Baseline to End of the Treatment in the following parameters: (i) stool microbiome analysis (bacterial composition); (ii) stool and plasma metabolic profiling; (iii) stool and plasma immune stimulatory capacity (in-vitro analysis); (iv) total IgE and specific IgE levels; (v) circulating immune cell profiling; (vi) questionnaire(s) and adverse effect (AE) and medication use reporting in diary.

The strains listed in TABLE 1 herein were deposited at the Leibniz-Institut DSMZ-Deutsche Sammlung von Mikroorganismen and Zellkulturen GmbH located at Inhoffenstr. 7B, D-38124 Braunschweig, on Jun. 27, 2019 in accordance with and under the provisions of the Budapest Treaty for the International Recognition of the Deposit of Microorganisms for the Purpose of Patent Procedure. The strains were tested by the DSMZ and determined to be viable. The DSMZ has assigned the following DSMZ deposit accession numbers to the respective strains: DSM 33213 (*A. muciniphila* (DSM 33213)), DSM 33179 (*B. longum* (DSM 33179)), DSM 33180 (*B. producta* (DSM 33180)), DSM 33178 (*B. thetaiotaomicron* (DSM 33178)), DSM 33176 (*C. comes* (DSM 33176)), DSM 33185 (*F. prausnitzii* (DSM 33185)), DSM 33191 (*F. prausnitzii* (DSM 33191)), DSM 33186 (*F. prausnitzii* (DSM 33213)), DSM 33190 (*F. prausnitzii* (DSM 33190)), DSM 33187 (*L. crispatus* (DSM 33187)), DSM 33177 (*B. faecis* (DSM 33177)), and DSM 33188 (*D. longicatena* (DSM 33188)).

Additional Embodiments

1. A pharmaceutical composition, wherein the pharmaceutical composition comprises: a bacterial consortium, wherein the bacterial consortium comprises at least one strain listed in Table 1; and at least one antioxidant.

2. The pharmaceutical composition of embodiment 1, wherein the bacterial consortium comprises at least two strains listed in Table 1.

3. The pharmaceutical composition of embodiment 1, wherein the at least one strain listed in Table 1 comprises *A. muciniphila* (DSM 33213), *F. prausnitzii* (DSM 33185), or *L. crispatus* (DSM 33187).

4. The pharmaceutical composition of embodiment 1, wherein the at least one strain listed in Table 1 comprises *A. muciniphila* (DSM 33213), *F. prausnitzii* (DSM 33185), and *L. crispatus* (DSM 33187).

5. The pharmaceutical composition of embodiment 1, wherein each strain of the at least one strain listed in Table 1 is present in an amount from about $10^7$ CFU to about $10^9$ CFU.

6. The pharmaceutical composition of embodiment 5, wherein the at least one strain listed in Table 1 is present in an amount of about $5 \times 10^8$ CFU.

7. The pharmaceutical composition of embodiment 1, wherein the at least one strain listed in Table 1 is present in a total amount from about $10^7$ CFU to about $10^{10}$ CFU.

8. The pharmaceutical composition of embodiment 7, wherein the at least one strain listed in Table 1 is present in an amount of about $5 \times 10^9$ CFU.

9. The pharmaceutical composition of embodiment 1, wherein the at least one antioxidant is L-cysteine.

10. The pharmaceutical composition of embodiment 9, wherein the L-cysteine is present in an amount from about 0.05% w/w to about 0.5% w/w.

11. The pharmaceutical composition of embodiment 1, further comprising a cryoprotectant.

12. The pharmaceutical composition of embodiment 11, wherein the cryoprotectant is glycerol.

13. The pharmaceutical composition of embodiment 12, wherein the glycerol is present in an amount from about 10% v/v to about 30% v/v.

14. The pharmaceutical composition of embodiment 1, further comprising a buffer.

15. The pharmaceutical composition of embodiment 14, wherein the buffer is PBS.

16. The pharmaceutical composition of embodiment 1, wherein the pharmaceutical composition is formulated in an oral dosage form.

17. The pharmaceutical composition of embodiment 16, wherein the oral dosage form is a capsule, tablet, emulsion, suspension, syrup, gel, gum, paste, herbal tea, drops, dissolving granules, powders, tablets, lyophilizate, a popsicle, or ice cream.

18. The pharmaceutical composition of embodiment 16, wherein the oral dosage form is a suspension.

19. The pharmaceutical composition of embodiment 16, wherein the oral dosage form is a popsicle, or an ice cream.

20. A pharmaceutical composition, wherein the pharmaceutical composition comprises: a bacterial mixture, wherein the mixture comprises: *A. muciniphila* (DSM 33213), *F. prausnitzii* (DSM 33185), and *L. crispatus* (DSM 33187); L-cysteine; and a cryoprotectant.

21. The pharmaceutical composition of embodiment 20, wherein each strain of the bacterial mixture is present in amount of about $5 \times 10^8$ CFU.

22. The pharmaceutical composition of embodiment 20, wherein the L-cysteine is present in an amount of about 0.1% w/w.

23. The pharmaceutical composition of embodiment 20, wherein the cryoprotectant is glycerol.

24. The pharmaceutical composition of embodiment 23, wherein the glycerol is present in an amount of about 20% v/v.

25. The pharmaceutical composition of embodiment 22, further comprising a buffer.

26. The pharmaceutical composition of embodiment 25, wherein the buffer is phosphate buffered saline (PBS) and has a pH of about 7.4.

27. The pharmaceutical composition of embodiment 20, wherein the pharmaceutical composition has a total volume of about 1 mL.

28. The pharmaceutical composition of embodiment 20, wherein the pharmaceutical composition is formulated into a suspension for oral administration.

29. A container comprising a pharmaceutical composition of any one of embodiments 1-28.

30. The container of embodiment 29, wherein the container is a 2 mL polypropylene screw cap vial.

31. The container of embodiment 29, wherein the container preserves the viability of at least 95% of bacterial cells in the pharmaceutical composition for about 12 weeks.

32. A kit comprising a container of any one of embodiments 29-31.

33. The kit of embodiment 32, further comprising instructions that direct a human user how to use the pharmaceutical composition in the container.

34. A method of manufacturing a pharmaceutical composition of any one of embodiments 1-28, the method comprising culturing at least two strains of the pharmaceutical composition, wherein culturing is performed in non-animal media; and combining the products of the culturing step thereby forming a bacterial consortium.

35. The method of embodiment 34, wherein the non-animal culture medium is a vegetal culture medium.

36. The method of embodiment 35, wherein vegetal culture medium comprises vegetal peptone, vegetal extracts, yeast extract, N-acetyl glucosamine (NAG), threonine, or a combination thereof.

37. A method for producing a batch of bacterial cells of a strain of Table 1, the process comprising growing the bacterial cells in a non-animal culture medium.

38. The method of embodiment 37, wherein the non-animal culture medium is a vegetal culture medium.

39. The method of embodiment 38, wherein vegetal culture medium comprises vegetal peptone, vegetal extracts, yeast extract, N-acetyl glucosamine (NAG), threonine, or a combination thereof.

40. The method of embodiment 39, wherein the strain of Table 1 is *A. muciniphila* (DSM 33213).

41. The method of embodiment 39, wherein the strain of Table 1 is *F. prausnitzii* (DSM 33185).

42. The method of embodiment 39, wherein the strain of Table 1 is *L. crispatus* (DSM 33187).

43. A method of manufacturing a pharmaceutical composition comprising a bacterial consortium comprising an *A. muciniphila* strain of Table 1, the method comprising culturing the *Akkermansia* sp. cells in a modified NAGT growth medium to produce an *A. muciniphila* cell batch.

44. The method of embodiment 43, wherein the modified NAGT growth medium comprises soytone, N-acetyl glucosamine (NAG), or a combination thereof.

45. The method of embodiment 43, wherein the modified NAGT growth medium does not comprise any one or more of magnesium, calcium, or glucose.

46. The method of embodiment 43, wherein the modified NAGT growth medium provides a 30-50% increased growth rate of the *A. muciniphila* cells compared to unmodified NAGT growth medium.

47. The method of embodiment 46, wherein the increase in growth rate is determined by measuring a difference in absorption at 600 nm of the growth media after 50 hours of cell culture.

48. The method of embodiment 43, wherein the *A. muciniphila* strain is *A. muciniphila* (DSM 33213).

49. The method of embodiment 43, wherein the *A. muciniphila* cell batch comprises about $5 \times 10^8$ CFU/mL.

50. A method of manufacturing a pharmaceutical composition comprising a bacterial consortium comprising *Faecalibacterium* sp., the method comprising culturing the *Faecalibacterium* sp. cells in a non-animal-based growth medium to produce a *Faecalibacterium* sp. cell batch.

51. The method of embodiment 50, wherein the non-animal-based growth medium is a yeast-based growth medium.

52. The method of embodiment 51, wherein the yeast-based growth medium comprises an YFAP vitamin mix.

53. The method of embodiment 51, wherein the yeast-based growth medium comprises sodium acetate, soytone, yeast extract, cysteine, or a combination thereof.

54. The method of embodiment 51, wherein the yeast-based growth medium comprises sodium acetate, soytone, yeast extract and cysteine.

55. The method of embodiment 50, wherein the *Faecalibacterium* sp. is *F. prausnitzii* (DSM 33185).

56. The method of embodiment 50, wherein the *Faecalibacterium* sp. cell batch comprises about $5 \times 10^8$ CFU/mL.

57. A method of manufacturing a pharmaceutical composition comprising a bacterial consortium comprising *L. crispatus* (DSM 33187), the method comprising culturing the *L. crispatus* (DSM 33187) cells in a yeast-based growth medium to produce a *L. crispatus* (DSM 33187) cell batch.

58. The method of embodiment 57, wherein the *Lactobacillus* sp. cell batch comprises $5 \times 10^8$ CFU/mL.

59. A method of treating a disease in a subject, the method comprising administering to the subject a pharmaceutical composition of any one of embodiments 1-27.

60. The method of embodiment 59, wherein the subject is a human.

61. The method of embodiment 60, wherein the human subject is from about 18 to about 40 years old.

62. The method of embodiment 60, wherein the human subject is an infant or a neonate.

63. The method of embodiment 62, wherein the infant is from about 0.5 years to about 3 years old.

64. The method of embodiment 62, wherein the neonate is no more than 6 months old.

65. The method of embodiment 62, wherein the neonate is no more than 3 months old.

66. The method of embodiment 57, wherein the pharmaceutical composition is orally administered to the subject.

67. The method of embodiment 59, wherein the bacterial consortium consists of *A. muciniphila* (DSM 33213), *F. prausnitzii* (DSM 33185), and *L. crispatus* (DSM 33187).

68. The method of embodiment 59, wherein the disease is an inflammatory disease.

69. The method of embodiment 59, wherein the inflammatory disease is an allergy or dermatitis.

70. The method of embodiment 69, wherein the allergy is allergic asthma, allergic pediatric asthma or food allergy.

71. The method of embodiment 59, wherein the disease is a metabolic disease.

72. The method of embodiment 71, wherein the metabolic disease is obesity, diabetes, or a metabolic syndrome.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for a growth of *Akkermansia* sp. comprising performing a plurality of inoculation rounds with an increasing amount of growth media,
    wherein an inoculation round of the plurality of inoculation rounds comprises use of at least about 5% by volume of a total batch material of a preceding inoculation round of the inoculation round of the plurality of inoculation rounds, and
    wherein a growth media of at least one inoculation round of the plurality of inoculation rounds is at least about 20 liters (L).

2. The method of claim 1, wherein the *Akkermansia* sp. comprises *Akkermansia muciniphila* or *Akkermansia glycaniphila*.

3. The method of claim 1, wherein the growth media of the at least one inoculation round of the plurality of inoculation rounds is at least about 150 L.

4. The method of claim 1, wherein the plurality of inoculation rounds further comprises a second inoculation round, and wherein a growth media of the second inoculation round of the plurality of inoculation rounds is from about 1 L to about 4,000 L.

5. The method of claim 1, wherein the plurality of inoculation rounds further comprises an initial inoculation round, wherein the initial inoculation round of the plurality of inoculation rounds comprises use of a frozen stock of the *Akkermansia* sp. comprising about 2% by volume of a growth media of the initial inoculation round of the plurality of inoculation rounds.

6. The method of claim 1, wherein the plurality of inoculation rounds further comprises an initial inoculation round, wherein the initial inoculation round of the plurality of inoculation rounds comprises growing the *Akkermansia* sp. in an anaerobic condition.

7. The method of claim 1, wherein the plurality of inoculation rounds further comprises a final inoculation round, and wherein a growth media of the final inoculation round of the plurality of inoculation rounds is about 3,000 L.

8. The method of claim 7, wherein the final inoculation round of the plurality of inoculation rounds comprises use of about 10% by volume of a total batch material of a preceding inoculation round of the final inoculation round of the plurality of inoculation rounds.

9. The method of claim 1, wherein the at least one inoculation round of the plurality of inoculation rounds comprises the *Akkermansia* sp. present in an amount of $OD_{585}$ of at least 2.5.

10. The method of claim 1, wherein the preceding inoculation round of the inoculation round is an immediately preceding inoculation round of the inoculation round.

11. The method of claim 1, further comprising performing a plurality of sterilization rounds and a plurality of degassing rounds for the growth media of the at least one inoculation round of the plurality of inoculation rounds, wherein a sterilization round of the plurality of sterilization rounds comprises autoclaving the growth media of the at least one inoculation round of the plurality of inoculation rounds at 121° C. for 20 minutes, and wherein a degassing round of the plurality of degassing rounds comprises degassing the growth media of the at least one inoculation round of the plurality of inoculation rounds with $N_2H_2CO_2$ (90:5:5).

12. The method of claim 1, further comprising lyophilizing a total batch material of the at least one inoculation round of the plurality of inoculation rounds.

13. The method of claim 12, further comprising centrifuging the total batch material of the at least one inoculation round of the plurality of inoculation rounds before the lyophilizing.

14. The method of claim 12, further comprising grinding the total batch material of at the least one inoculation round of the plurality of inoculation rounds after the lyophilizing.

15. The method of claim 1, wherein during a period of growth of a given inoculation round of the plurality of inoculation rounds, a growth media of the given inoculation round of the plurality of inoculation rounds has a pH value of less than about 7.

16. The method of claim 1, wherein during a period of growth of a given inoculation round of the plurality of inoculation rounds, a growth media of the given inoculation round of the plurality of inoculation rounds has a pH value of less than about 6.5.

17. A method of forming a bacterial composition, comprising:
(a) performing a plurality of inoculation rounds of at least one strain of *Akkermansia* sp. with an increasing amount of growth media, wherein an inoculation round of the plurality of inoculation rounds comprises use of at least about 5% by volume of a total batch material of a preceding inoculation round of the inoculation round of the plurality of inoculation rounds;
(b) mixing the at least one strain of *Akkermansia* sp. with at least one strain of *Faecalibacterium* sp.

18. The method of claim 17, further comprising (c) mixing the at least one strain of *Akkermansia* sp. with at least one strain of *Lactobacillus* sp.

19. A method of forming a bacterial composition, comprising:
(a) performing a plurality of inoculation rounds of at least one strain of *Akkermansia* sp. with an increasing amount of growth media, wherein an inoculation round of the plurality of inoculation rounds comprises use of at least about 5% by volume of a total batch material of a preceding inoculation round of the inoculation round of the plurality of inoculation rounds;
(b) mixing the at least one strain of *Akkermansia* sp. with at least one strain of *Lactobacillus* sp.

20. The method of claim 19, further comprising (c) mixing the at least one strain of *Akkermansia* sp. with at least one strain of *Faecalibacterium* sp.

* * * * *